(12) United States Patent
Truwit

(10) Patent No.: US 6,206,890 B1
(45) Date of Patent: Mar. 27, 2001

(54) REMOTE ACTUATION OF TRAJECTORY GUIDE

(75) Inventor: Charles L. Truwit, Wayzata, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/378,868

(22) Filed: Aug. 23, 1999

Related U.S. Application Data

(60) Division of application No. 09/078,913, filed on May 14, 1998, now Pat. No. 5,993,463, which is a continuation-in-part of application No. 09/058,092, filed on Apr. 9, 1998, which is a continuation-in-part of application No. 08/919,649, filed on Aug. 28, 1997, now abandoned, which is a continuation-in-part of application No. 08/856,664, filed on May 15, 1997, now abandoned.

(51) Int. Cl.$^7$ .................................................. A61B 19/00
(52) U.S. Cl. ........................... 606/130; 606/129; 600/417
(58) Field of Search ................................ 606/53, 56, 59, 606/72, 79, 80, 87, 96, 102, 129, 130; 600/407, 417, 429, 473, 476

(56) References Cited

U.S. PATENT DOCUMENTS

| | | |
|---|---|---|
| 3,017,887 | 1/1962 | Heyer . |
| 3,055,370 | 9/1962 | McKinney et al. . |
| 3,460,537 | 8/1969 | Zeis . |
| 4,312,337 | 1/1982 | Donohue . |
| 4,805,615 | 2/1989 | Carol . |
| 4,827,940 | 5/1989 | Mayer et al. . |
| 4,955,891 | 9/1990 | Carol .................................... 606/130 |
| 4,998,938 | 3/1991 | Ghajar et al. ......................... 606/130 |
| 5,030,223 | 7/1991 | Anderson et al. .................... 606/130 |
| 5,263,956 | 11/1993 | Nobles .................................. 606/130 |
| 5,280,427 | 1/1994 | Magnusson et al. ............ 374/413.01 |
| 5,569,266 | 10/1996 | Siczek .................................. 606/130 |
| 5,643,286 | 7/1997 | Warner et al. ....................... 606/130 |
| 5,662,111 | 9/1997 | Cosman ............................ 128/653.1 |
| 5,695,501 | 12/1997 | Carol et al. .......................... 606/130 |
| 5,776,143 | 7/1998 | Adams .................................. 606/130 |
| 5,776,144 | 7/1998 | Leysieffer et al. ................... 606/130 |
| 5,782,842 | 7/1998 | Kloess et al. ........................ 606/130 |
| 5,810,841 | 9/1998 | McNeirney et al. ................. 606/130 |
| 5,902,239 | 5/1999 | Buurman .............................. 600/427 |
| 5,920,395 | 7/1999 | Schulz ................................. 356/375 |
| 5,957,933 | 9/1999 | Yanof et al. ......................... 606/130 |

FOREIGN PATENT DOCUMENTS

| | | |
|---|---|---|
| 3937052 | 5/1990 | (DE) . |
| 0386936 | 9/1990 | (EP) . |
| 0486269 | 5/1992 | (EP) . |
| 0832611 | 4/1998 | (EP) . |
| 2237993 | 5/1991 | (GB) . |
| 97/21380 | 6/1997 | (WO) . |
| 98/17191 | 4/1998 | (WO) . |

Primary Examiner—Michael Buiz
Assistant Examiner—David O. Reip
(74) Attorney, Agent, or Firm—Schwegman, Lundberg, Woessner & Kluth, P.A.

(57) ABSTRACT

A surgical method and apparatus for accurately aligning the trajectory of, guiding of, and introducing or withdrawal of an instrument is disclosed. The apparatus includes a base which has a movable member movably attached to the base. The movable member has a passage therein which forms a portion of the trajectory path. A positioning stem further includes a first locator and a second locator. The first and second locators are associated with two different portions of the positioning stem so that they are essentially two points on a line. The first and second locators are also locatable by a scanning or imaging system. The positioning stem is removably attached to said movable member and used to position the movable member. Moving the movable member also moves the passage therein to different trajectories. Once the passage within the movable member more or less is aligned with a target within the body, a locking member locks the movable member into a fixed position. The movable member can be moved to different trajectories using a first hydraulic system. A second hydraulic system can be used to introduce or withdraw an instrument to or from the patient. A mechanical advancement tool can be substituted for the second hydraulic system. The surgical instrument may also be provided with a remote portion for controlling the instrument from a remote location. The instrument can also be computer controlled.

43 Claims, 43 Drawing Sheets

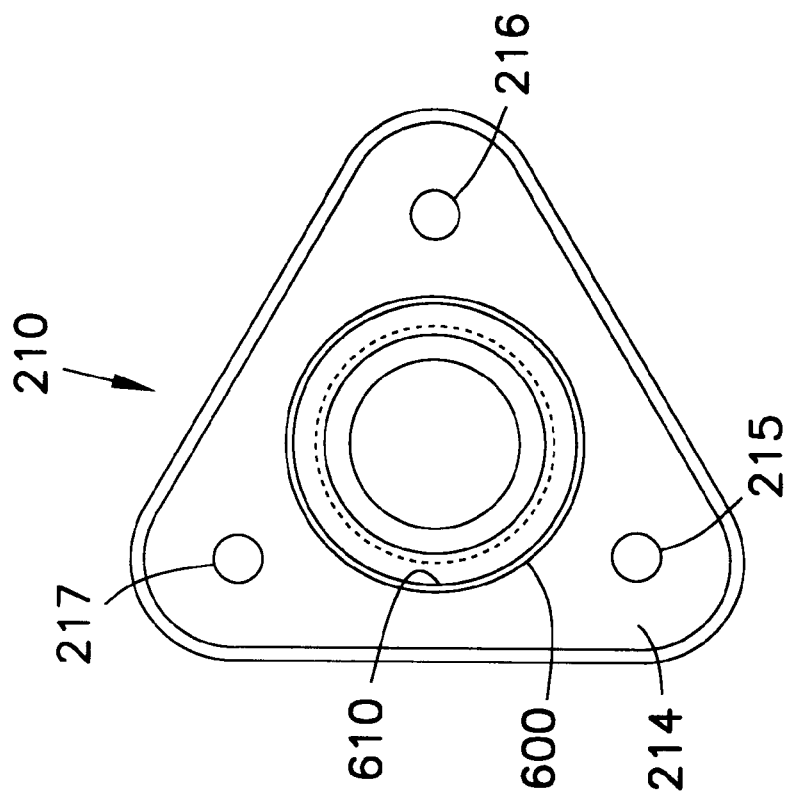
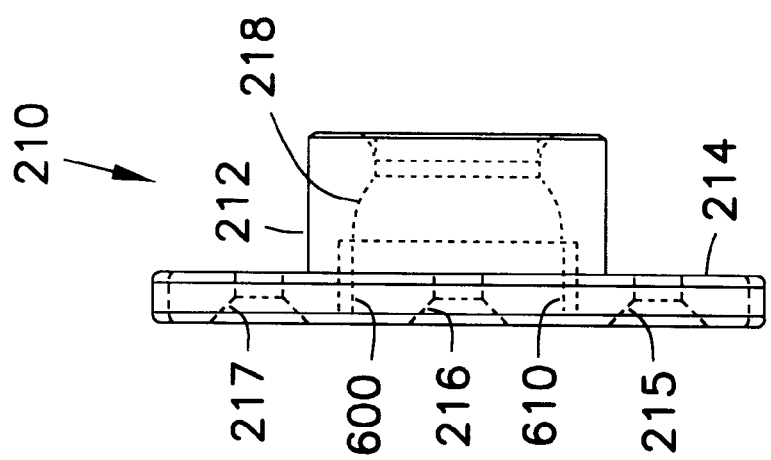

REMOTE ACTUATION OF TRAJECTORY GUIDE

CROSS-REFERENCE TO RELATED APPLICATIONS

This application is a divisional of U.S. patent application Ser. No. 09/078,913, filed on May 14, 1998, now U.S. Pat. No. 5,993,463, which in turn is a continuation-in-part of U.S. patent application Ser. No. 09/058,092, filed on Apr. 9, 1998, pending, which in turn is a continuation-in-part of U.S. patent application Ser. No. 08/919,649, filed on Aug. 28, 1997, now abandoned, which in turn is a continuation-in-part of U.S. patent application Ser. No. 08/856,664, filed on May 15, 1997 now abandoned.

FIELD OF THE INVENTION

The present invention is related to surgical working platforms. More specifically, the present invention relates to a working platform and method for using the same which facilitates the alignment of surgical and observational instruments into a patient.

BACKGROUND OF THE INVENTION

In the treatment of some diseases or defects associated with a patient, it has been found necessary to access specific targets within a patient. In the treatment of some diseases of or defects of human beings, it has been found necessary to access specific portions of the brain. Currently there are several methods for inserting surgical and observational instruments into a patient's brain.

U.S. Pat. No. 3,055,370 issued to McKinney et al. shows one currently used method for placing a surgical instrument to access a specific portion of the brain. The surgical instrument of the '370 patent includes a ball which has a bore. The direction of the bore can be changed. The instrument has an elongated tube of a specific length. A stylet is inserted within the tube to access the globus pallidus and perform a pallidotomy. An opening or burr hole is made in the skull at a specific landmark on the skull. Next, X-rays are taken in the fore-and-aft (AP) and lateral positions, and the line of the bar is projected downwardly by a ruler both in the fore-and-aft (AP) and lateral positions, so that the direction of the needle can be determined before it is inserted. When the direction of the longitudinal axis of the tubular member is determined to be satisfactory, a holder is threaded further into a tap to force a surface against a ball and lock a tubular member into place. Alignment of the trajectory is not measurable along a specific line occurring at the intersection of two planes. Alignment is dependent on placement of the burr hole at a specific location to determine one plane. X-rays are used to determine another plane-based use of common landmarks on the skull. The end result is that an educated guess is being used to position the stylet at the globus pallidus for the pallidotomy. One shortcoming with the method of using X-ray imaging to direct a surgical or observational instrument, is that many of the destinations within a patient are not viewable via X-ray. Another shortcoming relates to the slight shifting of intracranial contents, once a burr hole is placed and the dura and arachnoid are penetrated. Once cerebrospinal fluid is released via the burr hole, the intracranial contents (i.e. brain) may shift one or more millimeters. In such a case, the calculated trajectory is no longer accurate. Hence, there is an inherent inaccuracy with the described scheme.

Several other methods are also used to place instruments, catheters, or observational tools into patients. Currently, surgical procedures are performed through craniotomy flaps or craniotomy burr holes. A burr hole of about 14 mm is made in the skull. Needles or probes are typically passed through the burr hole into the brain using framed stereotaxy, frameless stereotaxy or freehand without stereotaxy.

The freehand method depends very heavily on the knowledge and judgment of the surgeon. In the freehand method, the surgeon determines the insertion point with a couple of measurements from a known landmark. The surgeon then looks at the measured point, makes adjustments, determines the angle of insertion and then inserts the surgical instrument or tool.

In framed stereotaxy, a ring frame is mounted to the patient's skull by multiple (typically three or four) pins or screws. This ring frame is used to determine a three dimensional data set. From this data set, Cartesian coordinates are calculated for both the lesion, the location of the pins or screws, and the fiducial marks on the frame. The ring frame fits into a large frame. A large frame is then attached to the patient in the operating suite. The large frame provides known positions and guides the surgical or observational instruments. The large frame is used to position the instrument to be introduced into the patient through a burr hole so that it intersects the target. In frameless stereotaxy, the ring frame is replaced with several markings on the patient's skull which can be used to determine several known positions. The large frame is replaced by a camera. The camera is usually infrared or some such device. Multiple sensors readable by the camera are placed on the instrument. For example, the surgical instrument or tool is provided with one or more light emitting diodes ("LEDs") which are tracked by the camera. The position of the surgical instrument can be calculated from the information from the LEDs on the surgical instrument or observational tool.

U.S. Pat. No. 4,955,891 and U.S. Pat. No. 4,805,615, both issued to Carol, each discuss the use of stereotaxy surgery with computerized tomographic ("CT") scanning. CT scanning is used to determine the exact position of a lesion or specific portion of the brain. After the exact position of the lesion or specific portion of the brain is determined, a phantom fixture is set up. The phantom fixture replicates the position of the ring frame on the patient. A phantom target is set up. The instrument can then be positioned on the phantom such that it intersects the target. The information from the phantom can then be used in actually positioning the instrument in the operating suite.

U.S. Pat. No. 4,998,938 issued to Ghajar et al. shows another surgical device for facilitating the insertion of an instrument into a patient's cranial cavity through a burr hole. The device includes a guide having an end configured to pass into the burr hole. There is a separate locking member. A body member includes alignment markings to help with insertion of a catheter or stylet. Unlike the '370 patent, there is no movable member for adjusting the path of the guide.

The methods currently in use all have a number of shortcomings. Most of the techniques currently used to place a surgical instrument or observational tool within a patient employ a limited amount of accuracy. In particular, current framed, frameless, and freehand methods compute or predict trajectories on the basis of imaging data or anatomic landmarks that do not account for the slight, but real shifting of the brain upon opening the cranium and meninges to the level of the subarachnoid space. This inherent inaccuracy inherently limits the success of these various methodologies. In other words, these systems do not use any means of updating the data files to include data obtained following the placement of a surgical burr hole and opening of the meninges. In addition, all the methods require large amounts of judgment on the part of the surgeon placing the surgical instrument or tool, and in particular, offer no direct feedback on the success or failure of the trajectory to reach the target. Very few of the techniques use an imaging or scanning apparatus to aid in the placement of the surgical instrument or observational tool. The only one that does requires a phantom frame and target to be set up to simulate the real geometry. In short, none of the apparatuses appear to use an imaging or scanning apparatus as extensively as they could be used to minimize the time and effort needed to accurately place a surgical instrument into a patient, and to offer immediate data on the success or failure of the trajectory to reach the target.

Still another disadvantage is that the apparatuses used today are not remotely controlled or actuated. In some operating environments, the patient is not accessible to the surgeon. Therefore, it is advantageous to have remote control of the tool. One such environment is within an MR magnet associated with an MR operating suite. When the patient is in an open magnet, the surgeon may have direct access to the patient. When in a closed magnet, the surgeon probably will not have such direct access to the patient.

SUMMARY OF THE INVENTION

A surgical method and apparatus for accurately aligning the trajectory of, guiding of, and introducing or withdrawal of an instrument is disclosed. The apparatus includes a base which has a movable member movably attached to the base. The movable member has a passage therein which forms a portion of the trajectory path. The movable member also includes a guide stem which has an opening therein. The guide stem is attached to said movable member such that the opening in the guide stem substantially aligns with the passage in the movable member. The movable member can include either an integral guide stem for holding the positioning stem or a removably attached guide stem. In the case of the former, a positioning stem is inserted into the opening of the guide stem for purposes of trajectory alignment. In the case of the latter, the removably attached guide stem can be removed and replaced with a positioning stem.

A positioning stem further includes a first locator and a second locator. The first and second locators are associated with two different portions of the positioning stem so that they are essentially two points on a line. The first and second locators are also locatable by a scanning or imaging system. The positioning stem is either inserted into the guide stem that is integral to the movable member, or is removably attached to said movable member and used to position the movable member. Moving the positioning stem while either within the guide stem or removably attached to the movable member also moves the passage therein to different trajectories. Once the passage within the movable member more or less is aligned with a target within the body, a locking member locks the movable member into a fixed position.

In one embodiment the first locator and the second locator are readable by a magnetic resonance imaging apparatus. The locator can include a fluid readable by a magnetic resonance imaging apparatus or a source of radio frequency, such as a coil, which is readable by a magnetic resonance imaging apparatus. In the latter embodiment, the first and second locators may be small radio frequency (RF) coils that detect an electromagnetic signal in a magnetic resonance imaging environment. The electromagnetic signal detected can be used to locate the first and second locators. The line formed by the first locator and the second locator may be substantially aligned with the centerline of the passage in the movable member or may be offset from the centerline of passage in the movable member. In other embodiments, the first and second locators may be light emitting diodes which are readable by an infrared camera.

The first and second locators may be located within an essentially solid plastic positioning stem, or in another embodiment, the first and second locators may be located within an MR-visible chamber within the positioning stem. In the latter embodiment, the chamber may be filled with an MR-visible fluid (paramagnetic, for example), which can be used to afford a first approximation of alignment. The first and second locators may be either MR-visible (different than the MR-visible chamber) or may be MR-invisible, in which case they would exhibit a negative image against the background of the MR-visible fluid within the larger chamber of the positioning stern. Advantageously, the fluid in the chamber produces an image which can be easily located and can be used to roughly align the positioning stem. The MR-visible or MR-invisible fluid of the first and second locators can then be used for fine or precise alignment.

In the embodiment where the guide stem and positioning stems are removably attached to the movable member, the movable member can include a threaded opening which receives either the guide stem or the positioning stem. In this embodiment where the guide stem is interchangeable with the positioning stem, one end of both the guide stem and positioning stem is threaded. A portion of the passage in the movable member has internal threads for receiving the threaded end of either the guide stem or the positioning stem. In the embodiment where the guide stem is formed as part of the movable member, the positioning stem fits within the opening in the guide stem. The movable member is a ball capable of swiveling with respect to the base.

In another embodiment, the movable member may also include a stage which allows for planar movement in a direction intersecting the trajectory. A surgical instrument, such as a needle, probe (cryotherapy probe, laser probe, RF ablation probe, microwave interstitial therapy probe, or focussed ultrasound therapy probe), catheter, endoscope, or electrode, can then be inserted through the movable member and the opening in said guide stem to guide the instrument toward the target position within the patient. In this embodiment, it is possible to reposition the surgical instrument without altering the trajectory itself, by first withdrawing it from the targeted tissue and then adjusting the stage in a direction intersecting the trajectory.

It is advantageous to have the trajectory guide operable from a remote location. Among the advantages is that the patient will not have to be moved in and out of an environment in order to make adjustments to the trajectory guide. Adjustments or use of the trajectory guide does not have to be interrupted when used in an environment where a surgeon or technician does not have access to the trajectory guide on the patient. This shortens the time spent for the surgical procedure which is appreciated by both the surgeon or technician as well as the patient. It should also be noted that the trajectory guide is also adaptable to other environments such as for use in a CT scan environment. In CT scanning, x-radiation is used in order to form the images. Overexposure to x-rays is harmful to patients who are undergoing procedures. Overexposure to x-rays is a concern to surgeons or technicians who perform these procedures. Therefore, it is advantageous to have the capability to maneuver the trajectory guide from a remote location so that the procedure can be done in a shorter amount of time and so that the physicians and technicians that may be using the trajectory guide can keep exposure to various imaging environments to a minimum.

In a first preferred embodiment of a remotely controlled trajectory guide, there is the actual trajectory guide and a remote trajectory guide. The remote trajectory guide is a duplicate of the actual trajectory guide. The remote trajectory guide has the same look and feel as the actual trajectory guide so that the surgeon or technician used to using the actual guide can move the remote guide as if it was the actual guide attached to the patient. The objective is to make the movement of the remote feel as though it was the actual guide. In this way, once the physician surgeon or the technician learns to use the actual guide they do not have to learn how to use the remote device. In the first embodiment, the tilt or trajectory defined by the trajectory guide and the advancement and of the surgical instrument is provided for by using a mechanical device using a cable or filament.

In a second preferred embodiment of a remotely controlled trajectory guide, a first hydraulic cylinder and a second hydraulic cylinder control actuators which may be used to position the positioning member. Once so positioned and after the movable member lock is locked, thereby also locking in the trajectory, the first and second hydraulic cylinder control actuators may be removed. A third hydraulic cylinder and actuator may then be used to control the insertion or withdrawal of an instrument. The hydraulic cylinders are especially useful for positioning the movable member and inserting or withdrawing the instrument when the patient is positioned remotely from the surgeon. Although many scanning devices allow access to a patient, there are many styles of scanning devices that do not allow access to the patient during a scanning operation. For example, in an MRI type scanning device, the magnet producing the magnetic field can be of several shapes. Some of the magnets are shaped such that a patient must be positioned out of reach of the surgeon in order to be within the homogeneous imaging volume of the magnetic field during a scanning operation.

In operation, a target within a patient is initially selected. A surgical opening into the body is made and the base is inserted into and surgically secured to the opening. The movable member and outer locking ring are also removably attached to the base. The positioning stem is then used to move the movable member and the passage therein to form a trajectory toward the target. The first locator portion and the second locator portion are read by the scanning device to determine the trajectory represented by the line of the positioning stem. The positioning stem is moved until the line represented by the positioning stem intersects the selected target. The positioning stem can be moved manually or by using the first hydraulic cylinder and actuator, and the second hydraulic cylinder and actuator. The line of the positioning stem may also be offset from the target in an alternate embodiment. Of course, the determination of the position of the first and second portions of the positioning stem is performed at least in part by the central processing unit and the memory of the scanning device. Once alignment is indicated, the movable member is locked into position which locks the trajectory represented by the positioning stem. The positioning stem is then removed either from the guide stem that is integral to the movable member, or, when the guide stem is not integral with the movable member, from the movable member itself. In the latter case, a guide stem is then attached to the movable member. The opening in the guide stem and the substantially aligned passage in the movable member form a trajectory in line with the selected target. The instrument is passed therethrough.

The third hydraulic cylinder and associated actuator can be used to control insertion or withdrawal of the instrument, if remote operation is desirable. Insertion or withdrawal can also be done manually. In situations where the target may be quite small, if the surgical instrument, upon successfully reaching the quite small target, reveals that the target selected, due to anatomic variance, is indeed not the true target, repositioning of the surgical instrument can be made by means of a slight offset. In such a situation, a stage can be moved so that a parallel trajectory can be followed. In such a situation, it may be advantageous and safer to employ a stage in order to minimize surgical trauma to the tissues.

The opening within the movable member and guide stem (whether integral to the movable member or removably attached) are designed to accommodate surgical instruments and observational tools. As there is a wide variety of different surgical instruments and observational tools, it is anticipated that multiple movable members and guide stems with openings of different diameter for such a wide array of surgical instruments and observational tools will be employed. In addition, in the case of a guide stem that is integral to the movable member, additional positioning stems of similar diameters to fit appropriately into the guide stems will be employed.

Advantageously, the scanning device used for diagnostic purposes can be employed to place an instrument within the body of a patient. There is no need for framed stereotaxy or unframed stereotaxy, two procedures which require large amounts of time to perform. Procedures that formerly required many hours can now be performed in substantially less amounts of time with the trajectory guide. Time is saved over framed or unframed stereotaxy since there is no need to spend time placing a frame onto the patient or calculating the location of several selected points before the actual introduction of a surgical instrument. The procedure is not only quicker, but provides for real time feedback as the surgical instrument progresses into the body. The computer associated with the scanning device also calculates the trajectory to determine if the line defined by the first locator and the second locator is collinear with the trajectory.

The surgical instrument can also be used in other applications without a first and second locator. For example, the movable member with a passage can be held by a clamp to guide catheters and other surgical instruments into the human body. The clamp includes a pair of cups for holding the movable member. The clamp is spring loaded so that it engages the movable member when the clamp is not held open. Several of the clamps can be held above a patient by individual snake devices or by a support bar that holds a plurality of clamps. A plate that holds several movable members can also be held above the patient or even attached to a patient to provide a platform from which to pass one or more surgical instruments through corresponding movable members. Such arrangements can be used for any type of surgery where it is advantageous to use rigid or flexible type surgical instruments, particularly as might be used in minimally-invasive surgical procedures. The trajectory defined by the trajectory guide and the advancement of the surgical instrument can be controlled from outside the scanning environment.

BRIEF DESCRIPTION OF THE DRAWINGS

For a better understanding of the present invention, reference may be made to the accompanying drawings in which:

FIG. 6a is a side view of the base of the trajectory guide.

FIG. 6b is a top view of the base of the trajectory guide.

DESCRIPTION OF THE EMBODIMENT

In the following detailed description of the embodiment, reference is made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the present invention. The following detailed description is, therefore, not to be taken in a limiting sense, and the scope of the present invention is defined only by the appended claims.

This application incorporates the following U.S. applications by reference:

U.S. patent application Ser. No. 08/919,649 entitled "Surgical Instrument Trajectory Guide Method and Apparatus", filed on Aug. 28, 1997;

U.S. patent application Ser. No. 08/856,664 entitled "Surgical Instrument Trajectory Guide Method and Apparatus", filed on May 15, 1997; and U.S. patent application Ser. No. 09/058,092 entitled "Trajectory Guide Method and Apparatus for use in Magnetic Resonance and Computerized Tomographic Scanners", filed on Apr. 9, 1998.

Figure 1:
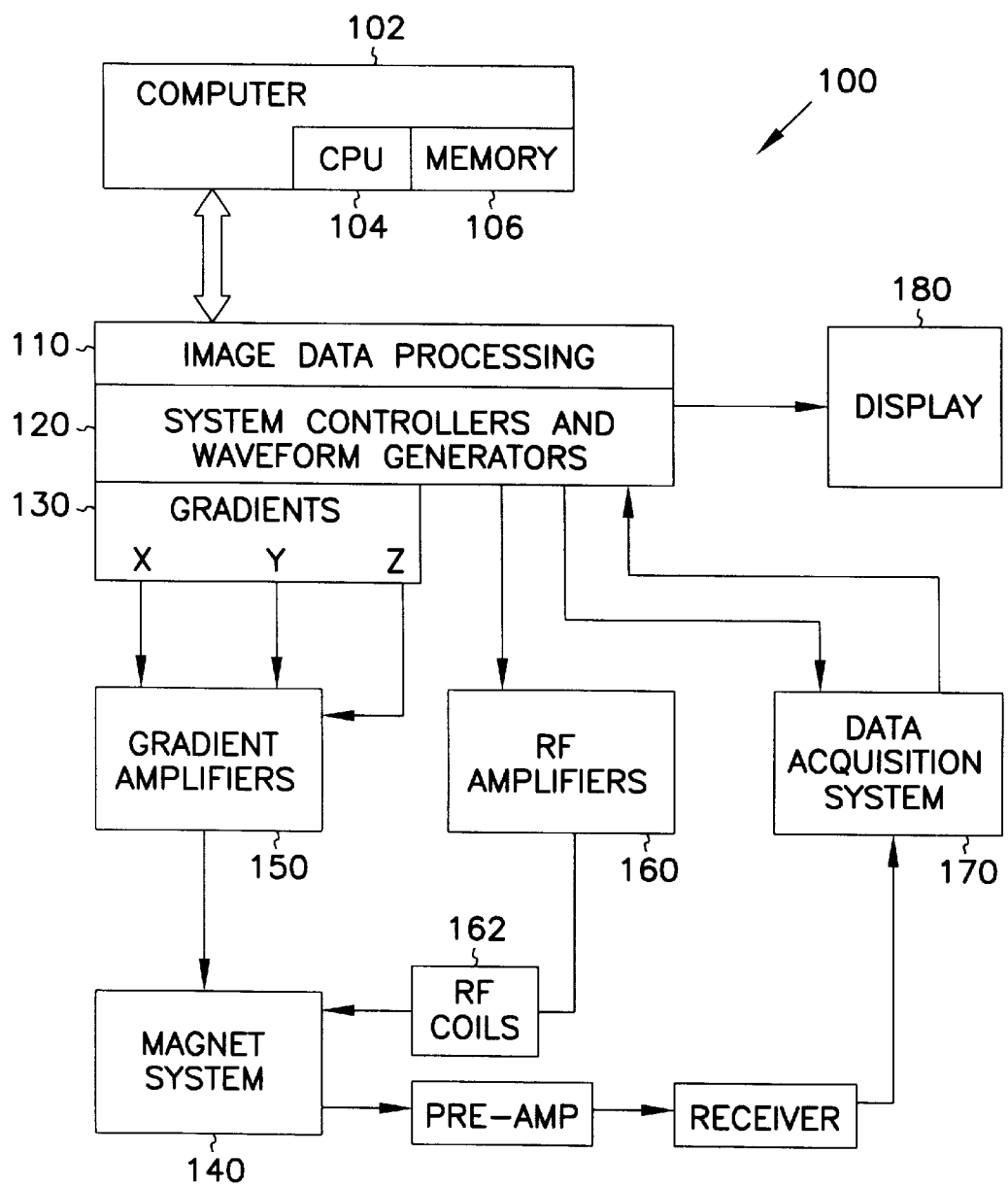
FIG. 1 is a block diagram of a patient scanning system.

FIG. 1 is a block diagram of a patient scanning system 100. The specific scanning system shown is for a magnetic resonance imaging ("MRI") system. An MRI scanning system 100 includes a computer 102. The computer 102 includes a central processing unit ("CPU") 104 and memory 106. The CPU 104 and memory 106 has the capacity to perform multiple calculations used to determine images as well as positions of various organs, or portions or within an image field.

The computer 102 controls an image data processing portion 110, a system controller and wave form generator portion 120, and an XYZ gradient producing portion 130. The XYZ gradients are amplified and used to provide a gradient magnetic field in the X, Y, and Z directions as part of a magnet system 140. The magnet system 140 includes a magnet which produces a magnetic field through which a patient can pass. The shape of the magnet varies among MRI systems. The shape of the magnet and its relation to the table upon which the patient lies, determines whether the patient can be accessed by a surgeon while an MRI is being performed. There are many styles of MRI devices that do not place the surgeon within a close enough proximity to allow access to the patient during an MRI scan operation.

The MRI system 100 also includes gradient amplifier 150. Also included are a set of RF amplifiers 160 and RF coils 162 which are used in conjunction with the magnet system 140 to produce and transmit RF pulses in the magnetic field. Either the same RF coil or another RF coil is used to detect the MR signals from the interrogated tissues. This detected MR signal is then amplified by a preamplifier 164 and received by a receiver 166 for transmission to the data acquisition system 170 and then transmitted to the image data processing computer system 110. The data acquisition system is input to the system controllers and waveform generator portion 120 of the computer 102 as part of a feedback loop. The data is interpreted and placed on a display 180 associated with the computer of the MRI system 100. The computer 102 and the CPU 104 and memory 106 can use data acquired from the MRI system 100 to build up images of a portion of the patient which is being scanned. The images are typically referred to as slices. For example, a horizontal slice and a vertical slice can be made of the portion of the body or patient being imaged. The computer can also recalculate and build other slices for use by doctors and radiologists having any selected orientation needed to facilitate study of various items within a patient. For example, lesions can be found within the body as well as certain organs. Different slices can be requested to facilitate study of these targets. From the data acquired, the position of the lesions or organs can also be very accurately determined using a Cartesian or polar coordinate system. The above description of the MR scanner is simply for demonstrative purposes and multiple alternative MR scanning systems can be described herein.

Figure 2:
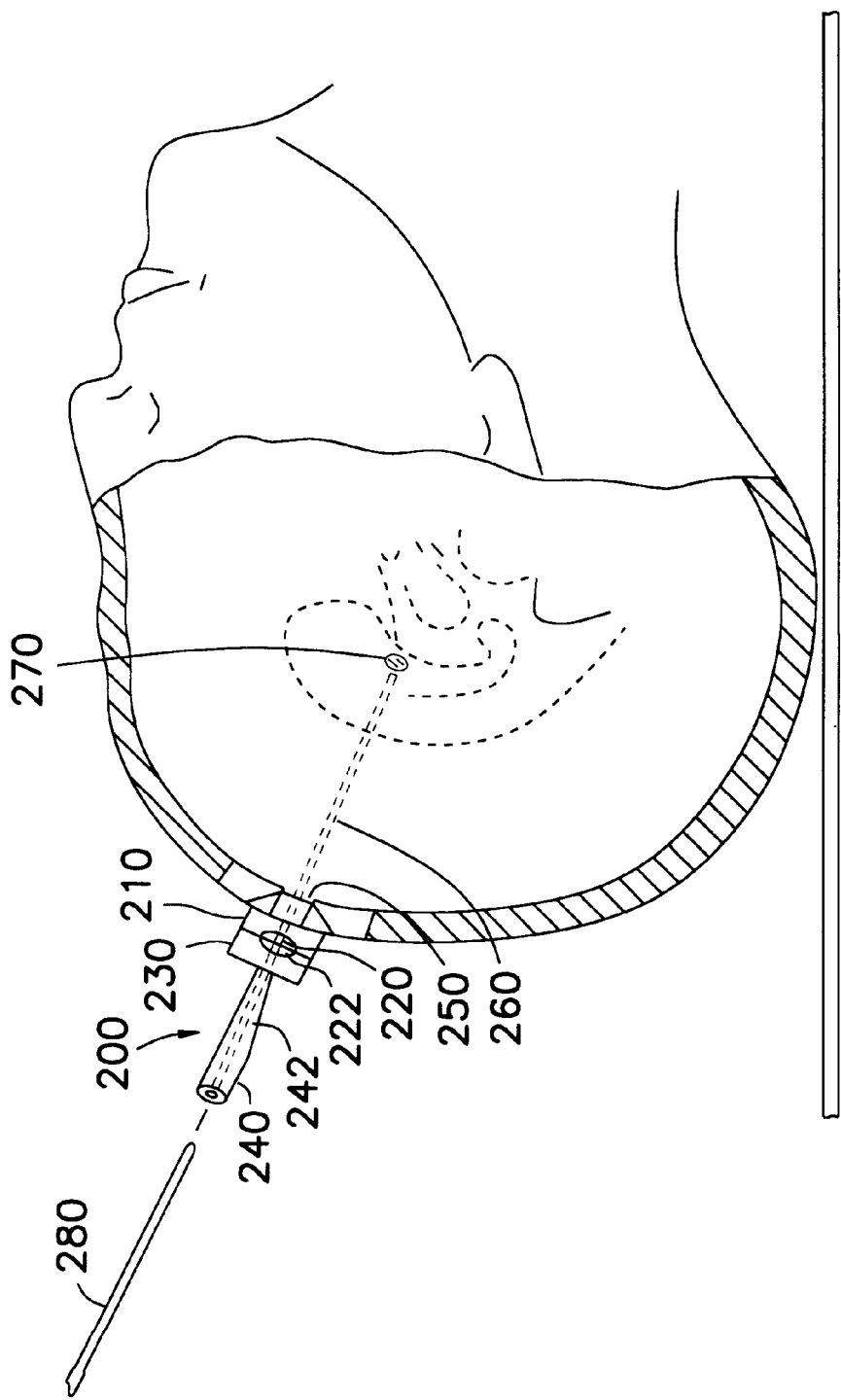
FIG. 2 is a partial cut away side view of a patient on which the trajectory guide is being used.

Within some parts of a patient, it is critical to very accurately place a surgical instrument. For example, in neurosurgery, it is very critical to have instruments, such as catheters or needles, placed very accurately within the cranium or head of a patient. FIG. 2 shows a side view of a patient on which trajectory guide 200 is being used. The trajectory guide 200 includes a base unit 210, a movable member 220, a locking member 230 and a guide stem 240. The base unit 210 is attached to the skull of the patient. In the particular embodiment shown, the attachment is made by way of bone screws. However, it is contemplated, that there may be any number of ways to attach the base 210 to the skull. For example, the base 210 could also be threaded to screw into a burr hole 250. The flange could also be added to the base 210 to attach the base to the skull.

The movable member 220 has a passage therein 222 which is shown in FIG. 2 as dotted lines. The guide stem 240 also has an elongated opening 242 therein. The opening 242 is also shown as dotted lines in FIG. 2. The passage 242 in the guide stem 240 and the opening 222 in the movable member or ball 220 form a line or a trajectory 260 which intersects with a target 270 within the patient. The guide stem 240 and movable member or ball 220 form the first part of the trajectory 260. A surgical instrument or observational tool can be inserted into the opening 242 of the guide stem 240 and passed through the passage in the movable member 220 and then further inserted into the patient a selected distance to the target 270. The opening 242 in the guide stem 240 and the passage 222 in the movable member 220 guide a surgical instrument along the trajectory 260 to the target 270. Of course, the movable member 220 is locked into place by locking member 230 before a surgical instrument 280 is placed through the opening 242 in the guide member 240.

Figure 3:
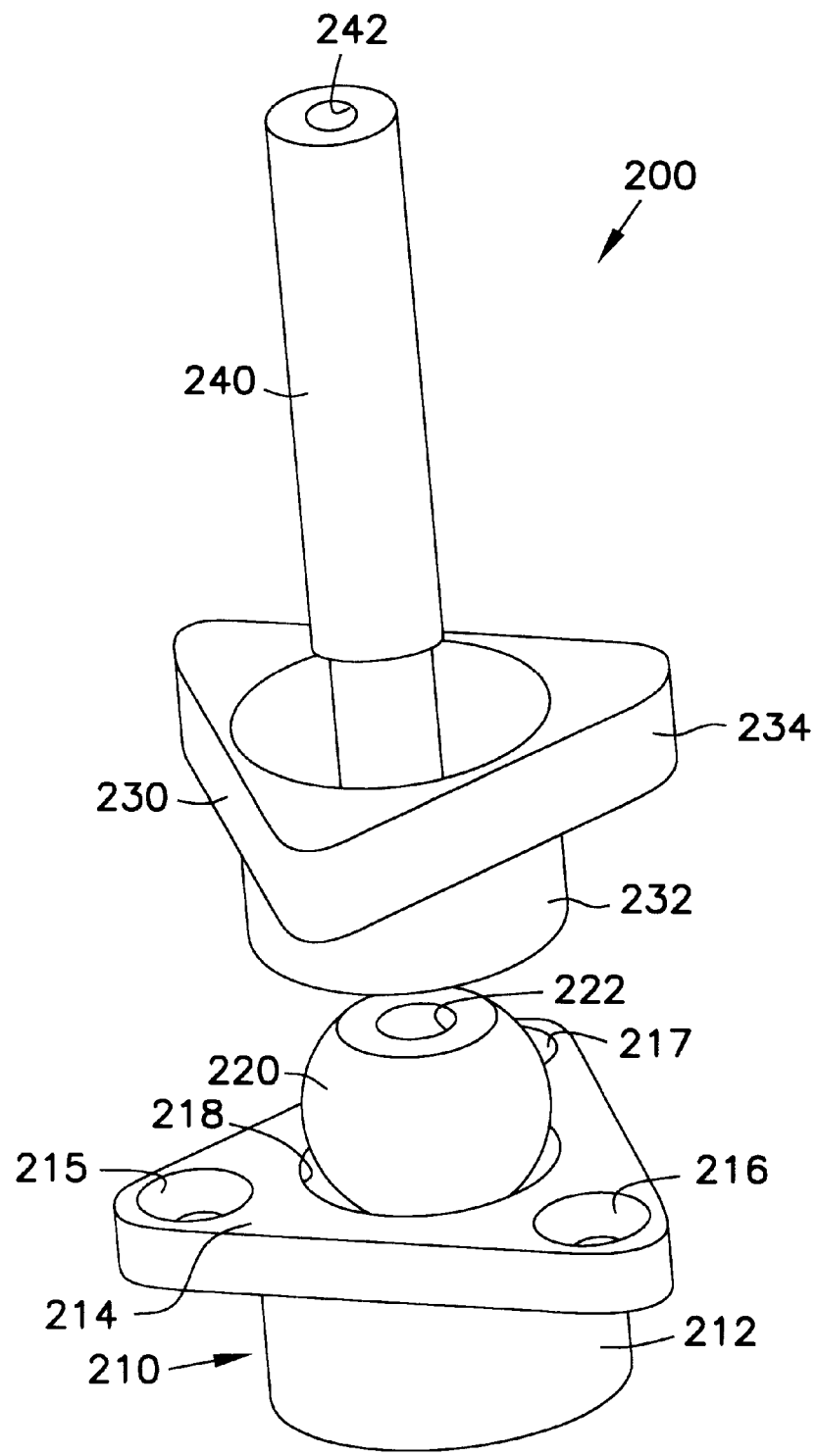
FIG. 3 is an exploded isometric view of the trajectory guide with a removably attached guide member installed.

FIG. 3 shows an exploded isometric view of the trajectory guide 200 with a guide member installed. As shown in FIG. 3, the trajectory guide 200 is comprised of a base 210, a movable member 220, a locking member 230, and a guide member 240. The base 210 includes a cylindrical portion 212 and a flange 214. The flange 214 includes a plurality of countersunk screw openings 215, 216, and 217. The countersunk screw openings 215, 216, and 217 receive bone screws which are screwed into the skull bone or the bone of a patient. The cylindrical portion 212 fits withing the burr hole 250 in the patient. The base also includes a semi-spherical seat 218. Although not shown in FIG. 3, there is an opening in the base 210 having a first end which terminates at the seat 218 and another end which terminates at the bottom of the base 210.

As shown in FIG. 3, the movable member 220 is essentially a spherical member or a ball. The spherical member or ball fits within the seat 218. The spherical member or ball moves freely within the seat 218. The ball-shaped movable member 220 also has an opening therein 222. The opening passes through the ball shaped movable member. One end of the opening may have a set of internal threads therein, which can be used to receive mating threads which are placed onto the guide stem or member 240 or positioning stem (discussed with respect to FIG. 4).

The locking member 230 also has an opening therethrough. The locking member 230 includes a cylindrical bottom portion 232 and a flange 234. The opening through the locking member 230 has sufficient space to allow movement of movable member 220 when the locking member is in an unlocked or untightened position. Although not shown in FIG. 4, the bottom of the cylindrical portion 232 of the locking member 230 includes a set of internal threads. The set of internal threads engage a set of external threads on the base unit 210 (shown in FIG. 7b). As will be detailed later, when the internal threads of the locking member 230 are engaged with the threads on the base 210, a portion of the locking member engages the movable member 220 to fix the movable member and the passage 222 therethrough at a fixed position.

A guide stem or guide member 240 is also shown in FIG. 3. The guide stem has an elongated opening 242 therein. The elongated opening passes through the length of the guide stem 240. One end of the guide stem includes a set of external threads which engage the internal threads of the spherical, movable member 220. When the external threads of the guide stem 240 engage the internal threads of the movable member 220, the opening 242 is substantially aligned with the passage 222 in the movable member. The opening 242 and passage 222 form the first part or guide for the trajectory 260 to the target 270 within the patient. It should be noted that the movable member 220 need not necessarily be a spherical element, although the spherical shape allows the ball to have a universal joint type swivel action which is preferred. It should also be noted that the movable element 220 and the guide stem 240 can be formed as one piece. This would eliminate the need for the threaded end of the guide stem 240 and the threaded inner diameter 222 of the movable member 220.

In addition, the locking member 230 can be formed in most any shape. A flange 234 is useful in that it allows additional leverage for tightening or loosening the locking member. Any shape capable of being turned or placed into a locking position with respect to the movable member 220 is acceptable.

Positioning Member

Figure 4:
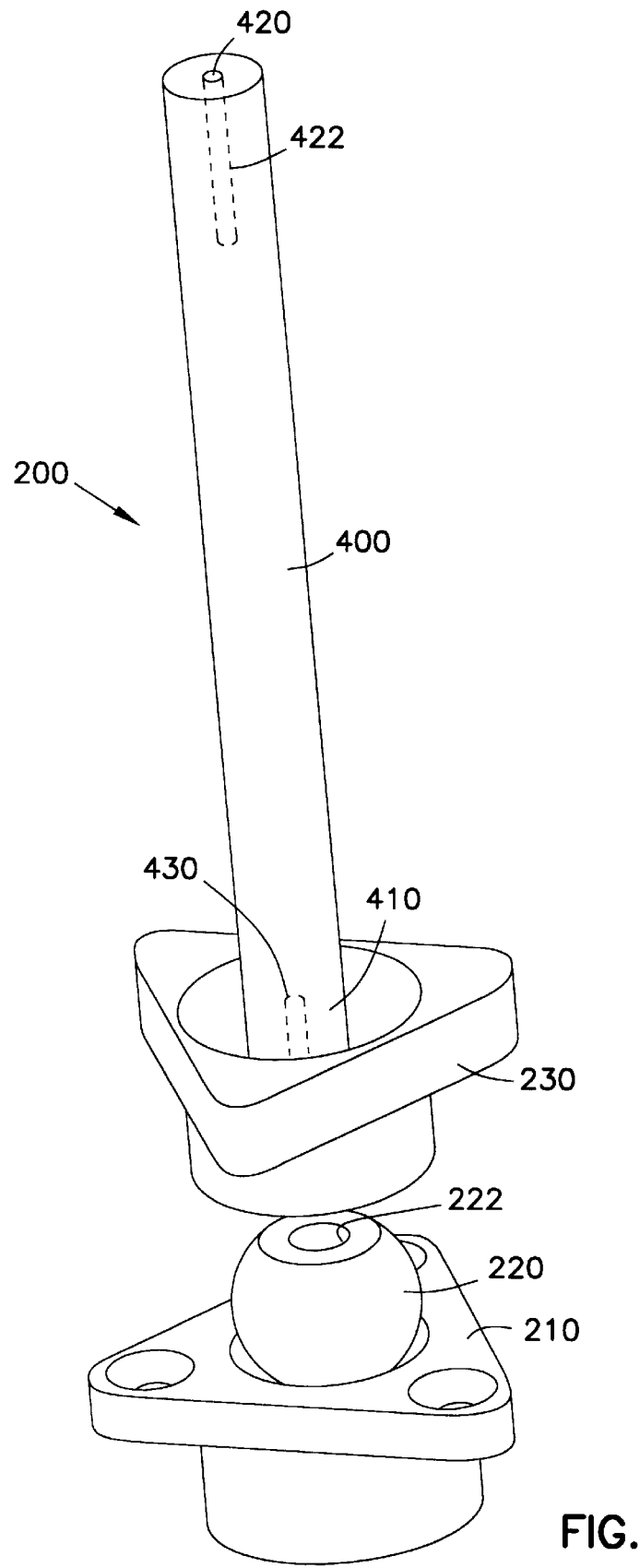
FIG. 4 is an exploded isometric view of the trajectory guide with a removably attached positioning member installed.

Now turning to FIG. 4, an exploded isometric view of the trajectory guide 200 with a positioning member 400 is shown. Many of the parts of the trajectory guide 200 shown in FIG. 4 are the same as those shown in FIG. 3. In the interest of time, a discussion of the common elements will not be repeated. Several of the basic elements will be numbered for the purposes of this discussion. The difference between FIGS. 3 and 4 is that the guide stem or guide member 240 has been replaced with a positioning stem. The positioning stem 400 includes an end 410 which carries threads for engaging internal threads within the passage 222 in the movable element 220. The positioning stem 400 also includes a first locator 420 and second locator 430. The first locator 420 includes a small opening 422 located at one end of the positioning stem 400. The small opening 422, which is shown in phantom in FIG. 4, is filled with a fluid or a substance that can be seen by a scanning device such as the MRI scanning device 100 described and shown in FIG. 1. After a fluid or substance is inserted into the opening 422 the end is sealed with a cap and adhesive. Similarly, the second locator 430 includes an opening 432 which contains a substance which is readable by a scanner such as an MRI scanner shown in FIG. 1. As shown in FIG. 4, the first locator 420 and the second locator 430 are coaxial with the axis of the cylinder formed by the positioning stem 400. It is contemplated that a first locator 420 and a second locator 430 could also be formed in an offset position from the axis of the cylinder formed by the positioning stem 400.

Figure 17:
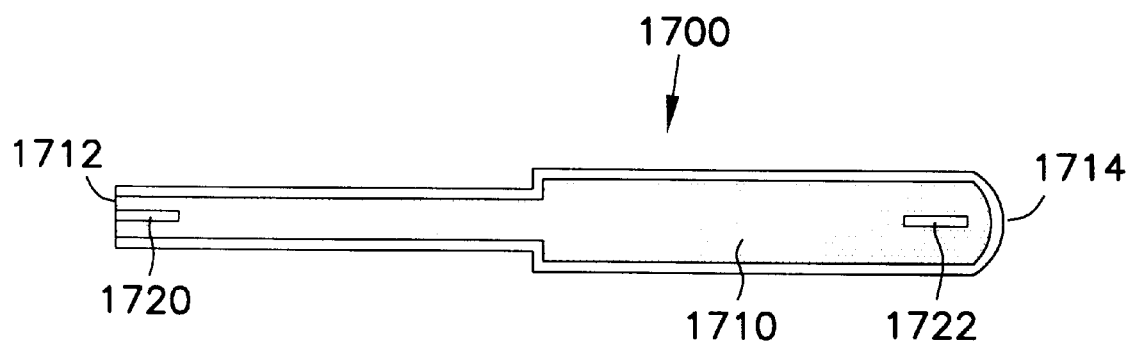
FIG. 17 is an side view of an alternate embodiment of a guide stem for the trajectory guide.

Now turning to FIG. 17, an alternate of embodiment of the positioning stem 1700 is shown. The positioning stem 1700 includes a chamber 1710 which is substantially hollow and sealed at both ends by end caps 1712 and 1714. A fluid, which is readable by nuclear magnetic resonance imaging system, is housed or kept in the chamber 1710 of the alternate embodiment positioning stem 1700. Within the chamber 1710 is a first locator 1720 and a second locator 1722. The first locator 1720 and the second locator 1722 may include a fluid doped with a different material which is discernable from the majority of fluid within the chamber 1710 by a nuclear magnetic resonance imaging system. The chamber 1710 with a first doped fluid can be easily located and is used for rough alignment of the positioning stem. The first locator 1720 and the second locator 1722 are used to more precisely align the positioning stem 1700 so that the opening 222 within the movable member 220 is on a straight line trajectory with a target within the patient. The positioning stem 1700 includes a shaft end 1730 which is adapted to fit within the opening 222 in the movable member 220 of the trajectory guide. Alternatively, the first and second locators 1720 and 1722 may consist of a solid material that appears on the MR image only by virtue of its absence of MR visibility.

Figure 18:
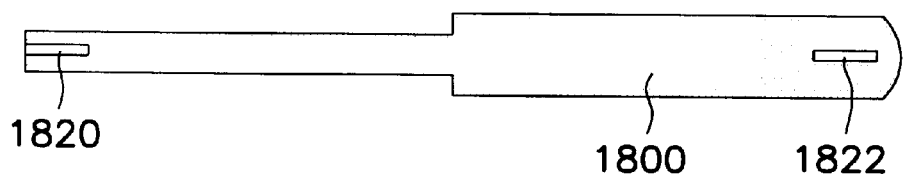
FIG. 18 is view of an image as seen on a display of a nuclear magnetic imaging system.

FIG. 18 shows the image that will be shown on the display 180 of a nuclear magnetic resonance imaging system 100. The image 1800 comprises two rectangles which reflect the shape of the chamber 1710. Each of the rectangles image 1800 has another image 1820 and 1822 therein. The image 1820 and the image 1822 can be used to precisely align the positioning stem and the opening 222 within the movable element 220 of the trajectory guide, so that the opening in the movable element forms a trajectory that intersects a target, such as 270, within the human body. This particular embodiment of the positioning stem 1700 is advantageous in that the main body of fluid within the hollow cylinder 1710 is more easily found and can be used for rough alignment.

The fluid filled openings could be replaced with small coils which detect a radio frequency readable by the scanning mechanism 100. Other transducers could be used for other scanning systems. The different transducers or elements would serve as the first locator 420 and the second locator 430 in another scanning system. For example, in frameless stereotaxy, infrared cameras are used to locate various points in space. It is contemplated that the first locator 420 could include at least one LED or light emitting diode readable by an infrared camera. Similarly, at least one LED or light emitting diode could be used for the second locator 430. Generally multiple LEDs or light emitting diodes are arranged in an array. Within the array, the LEDs or light emitting diodes are positioned so that the LEDs are at least a few degrees apart such that the infrared camera can discern a locational difference. In an embodiment that uses LEDs or light emitting diodes as locators, the LEDs must be positioned in view of the infrared camera.

The first locator 420 and the second locator 430 need not be the same type of readable transducer unit. For example, in an MR imaging system the first locator 420 could be an opening 422 filled with an MR readable substance while the second locator 430 could be a coil which detects and/or emits radio frequencies. Both would be readable on an MR imaging system.

Movable Member

Figure 5A:
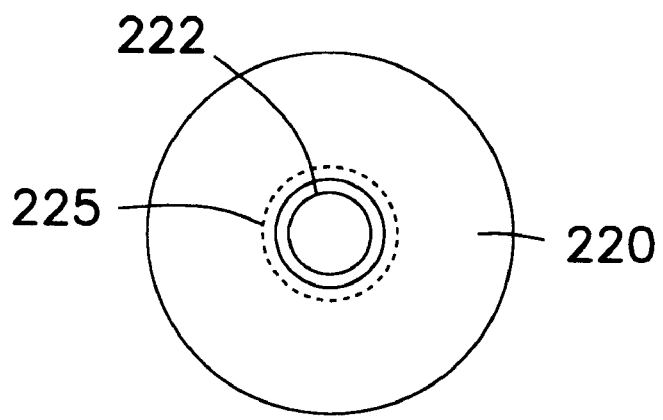
FIG. 5a is a top view of the movable member or ball of the trajectory guide.
Figure 5B:
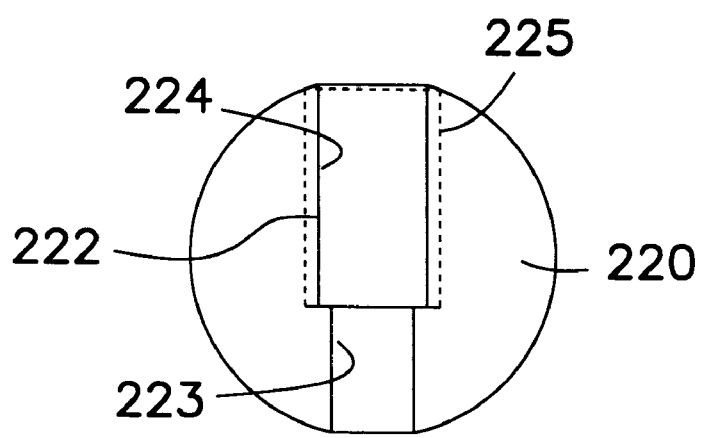
FIG. 5b is a side view of the movable member or ball of the trajectory guide.

FIGS. 5a and 5b show the movable member which will now be discussed in slightly more detail. FIGS. 5a and 5b show that the movable member 220 is substantially spherical in shape. The movable member 220 has an opening 222 therein. The opening 222 includes a smaller diameter portion 223 and a larger diameter portion 224. The inside surface of the larger portion 224 of opening 222 is threaded as indicated by reference numeral 225. The larger diameter portion 224 and the threads 225 receive the external threaded portion of either the positioning stem 400 or the guide stem 240. The smaller diameter portion 223 of the opening 222 is of a sufficient diameter to allow an instrument, such as a needle, probe, catheter, endoscope, or electrode to pass through the opening. The movable member 220 is made of a biocompatible material such as delrin.

FIGS. 6a and 6b show a side and top view of the base 210 of the trajectory guide 200. The base 210 includes the cylindrical portion 212 and the flange 214. The flange 214 includes countersunk openings 215, 216, and 217 as well as the seat 218 which receives the movable member 220. The seat 218 is part of an opening 600 which includes an internally threaded portion 610. The internally threaded portion 610 is dimensioned so as to receive the threaded external surface 700 of the locking member 230.

Now turning to FIGS. 7a and 7b, the locking member of the trajectory guide 200 will now be discussed. The locking member 230 includes the cylindrical portion 232 and a flange 234. The external surface of the flange 232 is threaded to form a threaded external surface 700. The threads associated with the externally threaded surface 700 are dimensioned so as to engage the internally threaded surface 610 of the base 210. The locking member 230 also includes an opening 710 which passes through the locking member 230. The locking member also has a locking surface 720. In this particular embodiment, the locking surface 720 is flat so that it engages a flat face on the movable member 220. The flanges 234 are extended so that the threads of the threaded surface 700 can be easily engaged with the internal threads 610 of the base 210. It is contemplated that other geometric shapes could be used for the locking member and that other locking surfaces could be employed.

In operation, a patient undergoes a scan with an apparatus such as an MRI or magnetic resonance imaging system 100 as part of a normal diagnostic medical procedure. A scan can be used to locate a particular organ within a patient or to locate lesions or any other target 270 within the patient. It should be noted that targets are not necessarily limited to being within the head of a patient. There can also be other areas of a patient where it would be critical to accurately place a surgical or observational tool. In addition, it should also be noted that the patient need not necessarily be human. A patient may include any living animal. Once a target is found and located using an MRI or other scanning system, the base 210 of the trajectory guide 200 can be attached to the patient. The base is affixed to the patient in an area near the target 270. The computer 102 of the scanning device 100 is used to determine the exact location of the target 270. The exact location can be found in any type of coordinate system, although normally a Cartesian coordinate system is used. Once the base 210 is attached to the patient, the remaining portions of the trajectory guide 200 are attached to the base 210. In other words, the movable member 220, the locking guide, the locking member 230 and a positioning stem 400 are added to form a complete trajectory guide 200.

The first locator 420 and the second locator 430 of the positioning stem 400 are read by the scanning system 100 and a line defined by the first locator 420 and the second locator 430 is calculated by the computer 102. The calculated line corresponds to the center line of the passage 222 and the opening 242 of the guide stem. If the line aligns with the target 270, the locking member is used to lock the movable member 220 into position. If the line does not intersect the target 270, the positioning stem 400 is moved until a line is formed by the first locator 420 and the second locator 430 intersects the target 270. If the patient and the positioning stem 400 can be easily reached by a surgeon during a scanning operation, positioning stem 400 can be moved or readjusted manually. If the patient is remote from the surgeon or cannot be reached by the surgeon, a hydraulic or other actuator may be used to move the positioning stem 400. Once such a line is formed the locking member 230 is secured.

After fixing the position of the movable member 220, the positioning stem 400 is removed, and the guide stem 240 is attached to the movable member 220. Once the guide stem 240 is attached to the movable member 220 the trajectory 260 is formed by the opening 242 and the passage 222. The guide is then positioned so that an instrument or an observational tool may be placed through the guide opening to intersect the target 270.

Remote Actuation and Control—First Embodiment

Figure 30:
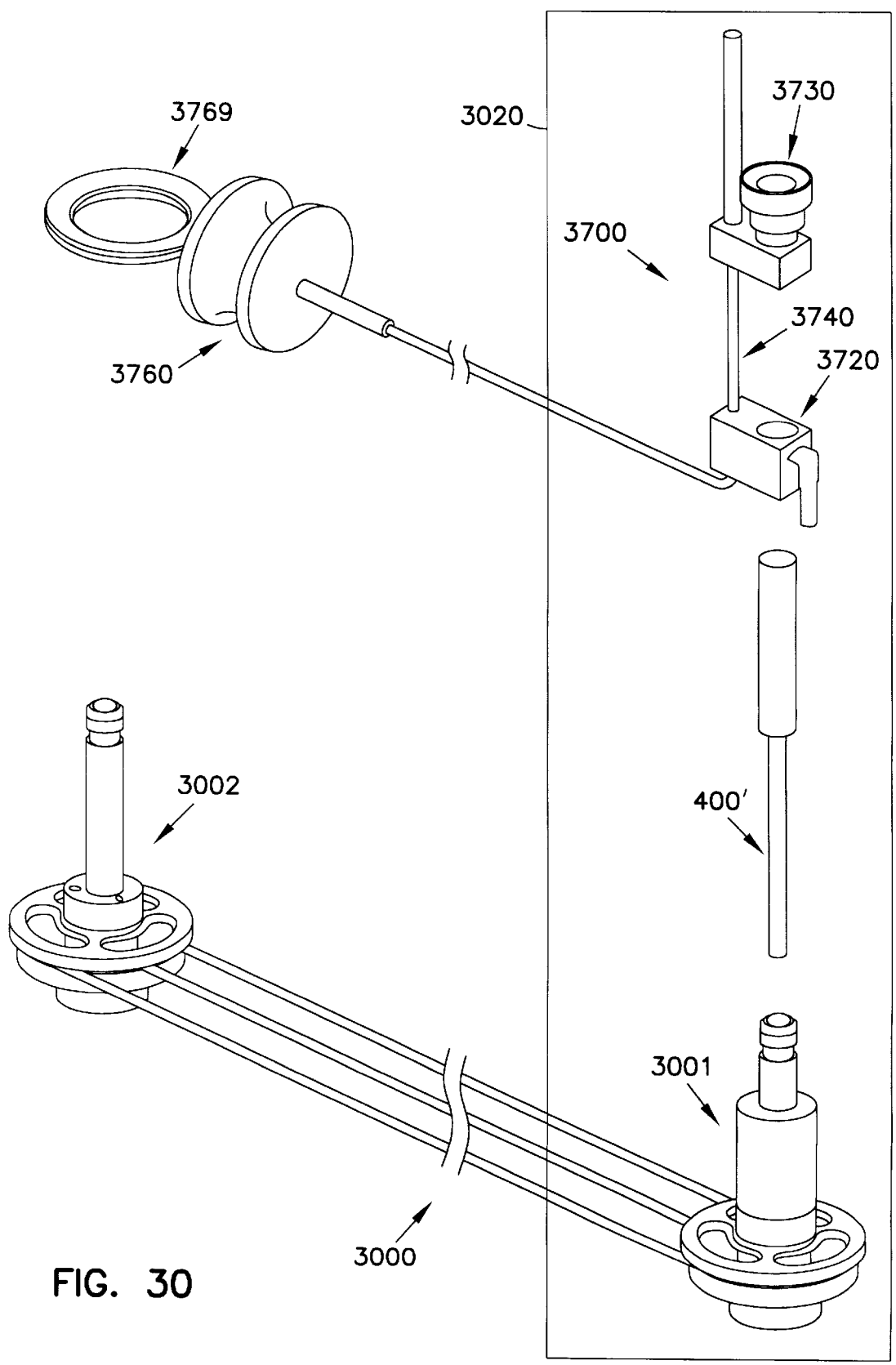
FIG. 30 shows a perspective view of a preferred embodiment of a mechanical remotely actuated trajectory guide mechanism.
Figure 31:
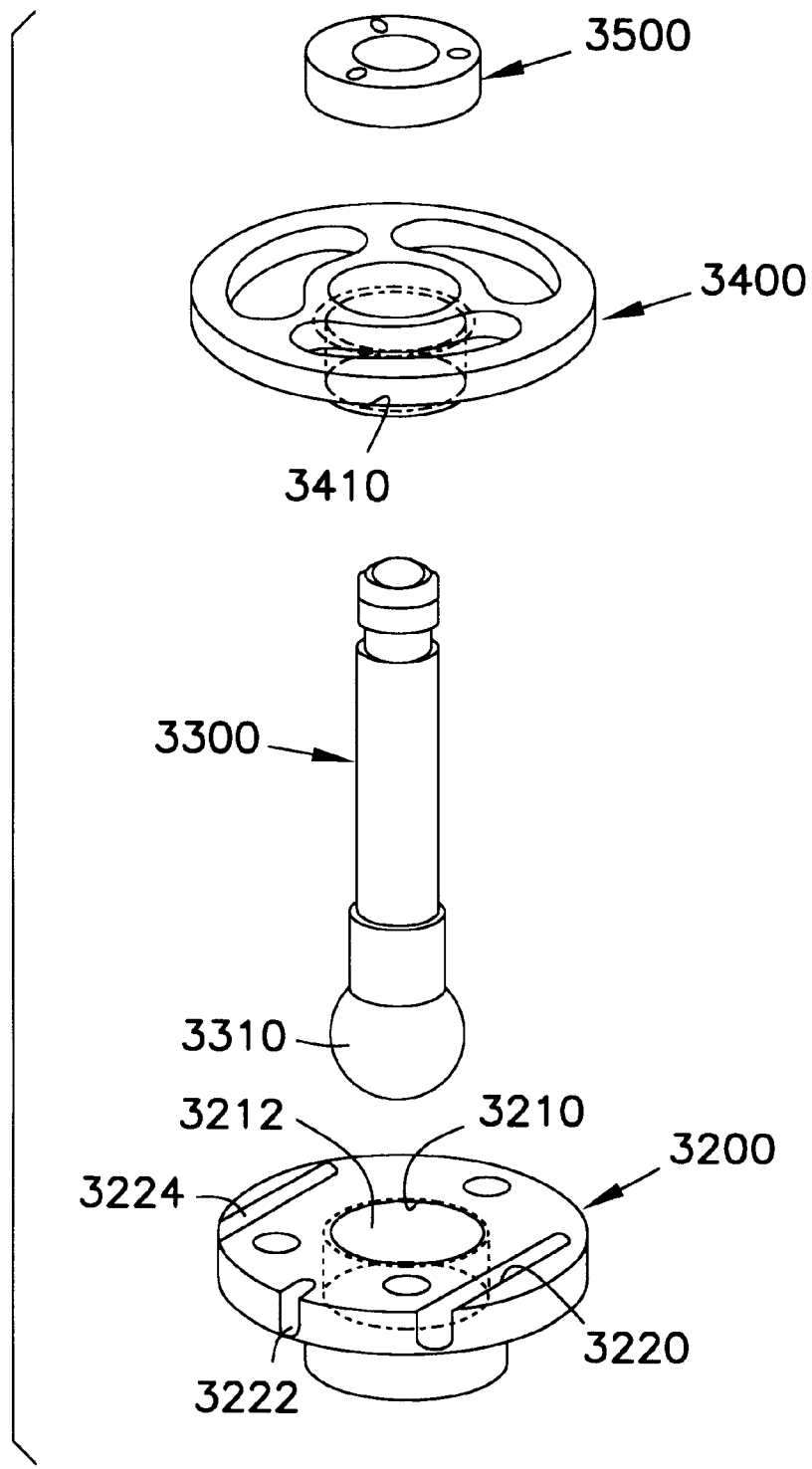
FIG. 31 is a perspective view of one of the first or second trajectory guides used as part of the mechanical remotely actuated trajectory guide mechanism shown in FIG. 30.
Figure 32:
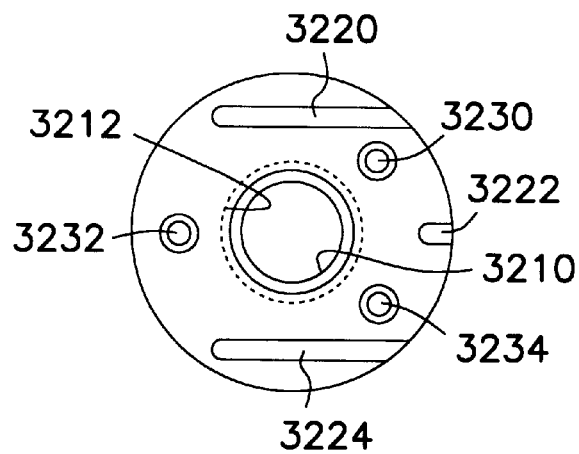
FIG. 32 is a top view of the base of the trajectory guide used as part of the mechanical remotely actuated trajectory guide mechanism.

FIGS. 30 to 32 detail a mechanical remote actuation and control device 3000. The mechanical remote actuation and control device 3000 includes a first or actual trajectory guide 3001 which is attached to a patient and a second trajectory guide 3002 that is remote from the patient. The second trajectory guide 3002 is sometimes referred to as the remote trajectory guide 3002. The second trajectory guide 3002 is a duplicate of the first trajectory guide 3001. The first trajectory guide 3001 and the second trajectory guide 3002 each have the same look and feel. In this way, the physician surgeon or technician using a remote actuation control device 3000 only has to learn how one particular trajectory guide, such as the first trajectory guide 3001 or the second trajectory guide 3002, works rather than learning the look and feel of both the actual trajectory guide 3001 and the second or remote trajectory guide 3002.

Typically, first trajectory guide 3001 is attached to a patient that is within a scanning environment 3020. The scanning environment 3020 can be an MR imaging suite as described above or can be a CT scanning environment as will be discussed in more detail below or can be in any other scanning or imaging environment. The second trajectory guide 3002 is outside the scanning environment. Using the remote actuation control device 3000, a surgeon or physician can then manipulate the first trajectory guide 3001 that is within the scanning environment by manipulating the second trajectory guide 3002 that is outside the scanning environment. In many cases, the first trajectory guide 3001 is not accessible while the patient and the first trajectory guide 3001 are located within the scanning environment. Being able to manipulate the first trajectory guide 3001 by moving the second trajectory guide 3002 positioned outside the scanning environment allows the physician surgeon to make necessary adjustments to the first trajectory guide 3001 without having to remove the patient from the scanning environment. This saves time for the surgical procedure as moving a patient in and out of a scanning environment takes a large amount of time. In addition, since the procedure is shortened, the exposure of the patient to any detrimental aspects of the scanning environment is also lessened. In addition, the physician surgeon is also not exposed to the scanning environment. As an overview, MR and x-ray compatible cables 3030, 3032 and 3034 are used to translate the motion at the second trajectory guide 3002 or remote trajectory guide to the first trajectory guide 3001 which is attached or otherwise associated with the patient. The term cable means any type of strong wires or other filaments that can translate the motions of the second trajectory guide 3002 to the first trajectory guide 3001. The filaments or wires used in the device are made of materials which are compatible with the scanning environment. For example, if the remote actuation control device 3000 is used in an MR environment, the material for the cables must be made of a non-magnetic material as strong magnetic fields are used in an MR environment. It should be noted that FIG. 30 also shows the surgical instrument advancement assembly 3700 which will be more fully discussed below in the description of FIG. 37.

Now turning to FIG. 31, the details of the first trajectory guide 3001 and the second trajectory guide 3002 will be discussed. The first trajectory guide 3001 and the second trajectory guide 3002 are identical to one another so rather than describe the same item twice for the sake of saving space, only one will be described in detail. FIG. 31 is a perspective view of one of the first or second trajectory guides, 3001 or 3002, used as part of the mechanical remotely actuated trajectory guide mechanism shown in FIG. 30. The trajectory guide 3001 includes a base 3200, a movable element also called a guide stem 3300, a locking member 3400 and a guide stem cable mount 3500. The guide stem 3300 has a ball or rounded end 3310 which is received in an opening 3210 in the base 3200. The locking member 3400 fits over the ball end 3310 of the guide stem 3300. The locking member has an outside threaded portion 3410 which engages an inside thread 3212 in the opening 3210 of the base 3200. The ball end 3310 of the guide stem 3300 moves or rotates freely within the opening 3210 of the base 3200 until the locking member 3400 is screwed into engagement with the ball end 3310 and the base 3200. The guide stem cable mount 3500 fits over the guide stem 3300 and sits atop the locking member 3400. The base 3200 has a plurality of recesses 3220, 3222, and 3224 which accommodate the cables 3030, 3032, and 3034. When the locking member 3400 is engaged with the base 3200 the recesses are covered in part by the locking member 3400 to form routing paths for the cables 3030, 3032, and 3034.

FIG. 32 is a top view of the base 3200 of the trajectory guide 3001 used as part of the mechanical remotely actuated trajectory guide mechanism 3000. As shown in FIG. 32, the base 3200 includes an opening 3210. The opening 3210 does not pass completely though the base 3200 but is rather a pocket for receiving the ball end 3310 of the guide stem 3300. The bottom of the opening 3210 is chamfered so that the ball end 3310 contacts the opening on a line about the ball end. The opening 3210 also has an inside threaded portion shown by the dotted lines 3212. In addition, the base 3200 includes the recesses 3220, 3222, and 3224 for receiving cables. Three recesses are shown. It should be understood that additional recesses could be formed if the particular design required more cables. In addition, it should also be understood that there could be a lesser number of recesses if there were less numbers of cables were used. It is also conceivable that the recesses could be eliminated altogether and provided elsewhere other than on the base 3200. The base 3200 also includes openings 3230, 3232, and 3234 which could receive mounting screws or could be used to mount the base 3200 to any other type of mount on the body of a patient.

Figure 33:
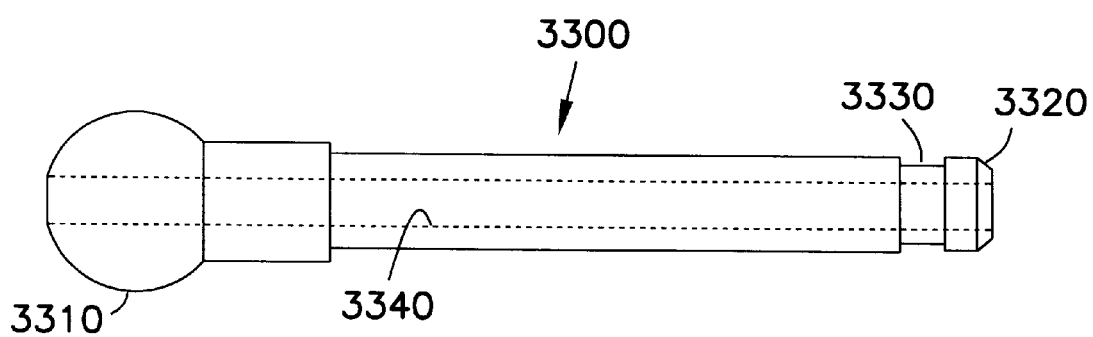
FIG. 33 is a side view of the guide stem of the trajectory guide used as part of the mechanical remotely actuated trajectory guide mechanism.

FIG. 33 is a side view of the guide stem 3300 of the trajectory guide 3001 used as part of the mechanical remotely actuated trajectory guide mechanism 3000. The guide stem 3300 has a ball shaped end 3310 and free end 3320. Near the free end 3320 is a detente or groove 3330. The guide stem 3300 has an opening 3340 therein which runs the length of the guide stem 3300. The opening 3340 is dimensioned so that a surgical instrument can be received and passed through the guide stem 3300. The opening 3340 is positioned so that it is coaxial with the trajectory to the target 270 within the patient. The guide stem 3300 of the trajectory guide 3001 is the moveable member which is moved so that the opening is coaxial or on target with the target 270 within the patient.

Figure 34:
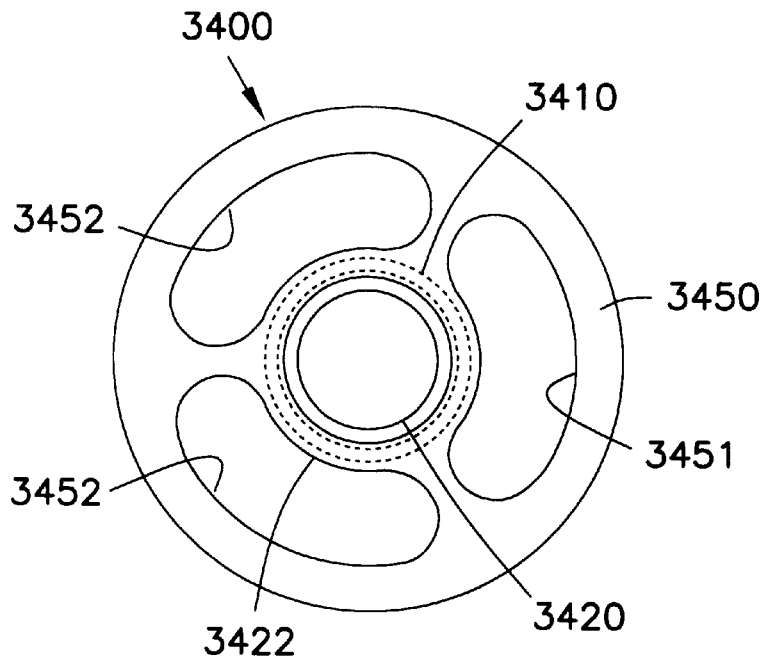
FIG. 34 is a top view of the locking member of the trajectory guide used as part of the mechanical remotely actuated trajectory guide mechanism.

FIG. 34 is a top view of the locking member 3400 of the trajectory guide 3001 used as part of the mechanical remotely actuated trajectory guide mechanism 3000. The locking member has an opening 3420 therein which passes all the way through the locking member 3400. The opening 3420 is dimensioned to allow motion of the guide stem 3300 so that the guide stem 3300 can be repositioned to align the opening 3340 therein with the trajectory to the target within the patient The opening is the inside of a tubular portion 3422 which has an outside threaded portion 3410. The locking member 3400 includes a disk shaped portion 3450 having a larger diameter than the tubular portion 3422. The larger diameter of the disk shaped portion 3450 makes it easier for an surgeon or technician to tighten the locking member 3400. The outer diameter of the disk shaped portion may be provided with frictional edge, such as a knurled edge, to further enhance the ability to tighten the locking member 3400 with respect to the base 3200. The disk shaped portion 3450 also has several large openings 3451, 3452, and 3453 therein. The openings 3451, 3452, and 3453 provide clearance for the cables 3030, 3032 and 3034 which pass therethrough and are attached to the guide stem cable mount 3500 which rests or sits adjacent the locking member 3400.

Figure 35:
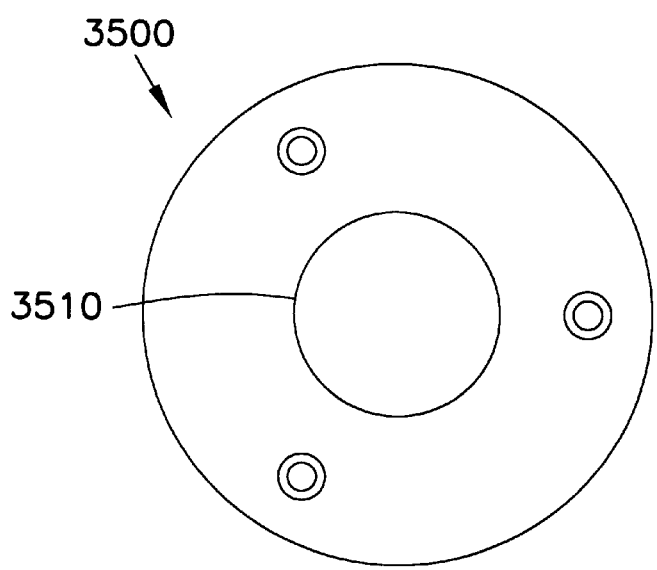
FIG. 35 is a top view of the guide stem cable mount of the trajectory guide used as part of the mechanical remotely actuated trajectory guide mechanism.

FIG. 35 is a top view of the guide stem cable mount 3500 of the trajectory guide 3001 used as part of the mechanical remotely actuated trajectory guide mechanism 3000. The guide stem cable mount 3500 includes a central opening 3510 which is dimensioned to fit over the guide stem 3300 with an adequate clearance to allow the guide stem 3300 to pass but with a small enough clearance to exert a force on the guide stem 3300 when cables 3030, 3032 and 3034 are placed in tension by moving the other guide stem. The guide stem cable mount 3500 includes several other openings 3520, 3522, and 3524 for receiving the ends of the cables 3030, 3032 and 3034. Each opening 3520, 3522, and 3524 is spaced a set distance from the center of the guide stem cable mount 3500. Each opening includes a larger diameter portion for receiving holding the end of the cable. Each cable 3030, 3032 and 3034 has an enlarged end for fitting within the openings 3520, 3522, and 3524.

Figure 36:
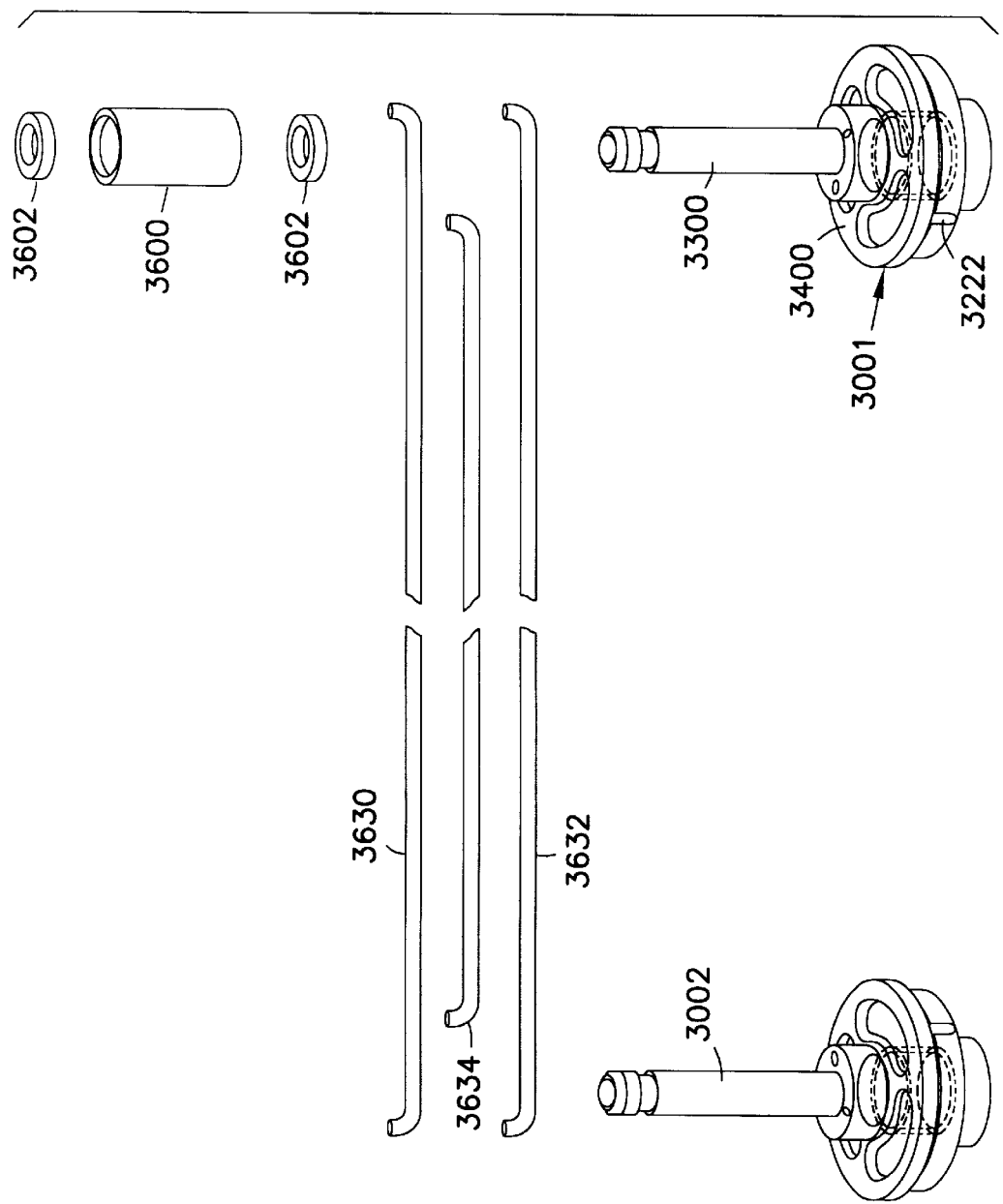
FIG. 36 is an exploded perspective view of the mechanical remotely actuated trajectory guide mechanism with the spacing sleeve for spacing the surgical instrument advance mechanism up the guide stem.

FIG. 36 is an exploded perspective view of the mechanical remotely actuated trajectory guide mechanism 3000 with the guide spacing sleeve 3600 for spacing the surgical instrument advance mechanism 3700 up the guide stem 3300. The cables, filaments or wires 3030, 3032 and 3034 travel within cable sleeves 3630, 3632 and 3634. Each of the cable sleeves 3630, 3632 and 3634 has a first turned end that fits within the recesses 3220, 3222, 3224 of the first base 3200 of the first trajectory guide 3001, and a second turned end that fits within the recesses 3220, 3222, 3224 of the second base 3200 of the second trajectory guide 3002. After the guide stem 3300 of the first trajectory guide 3001 is positioned using the guide stem 3300 of the second trajectory guide 3002 so that the opening 3340 is coaxial with the trajectory to the target in the patient, the patient is removed from the scanning environment 3020. While outside the scanning environment, the locking member 3400 is tightened to affix the guide member 3300 in place. The next step while the patient is outside the scanning environment 3020, is to add the surgical instrument and the surgical instrument advance mechanism 3700 (discussed in detail in FIG. 37). Initially, several spacers are added for the proper placement of the surgical instrument advance mechanism 3700. The surgical instrument advance mechanism has a portion that locks or snaps onto the detente or groove 3320 in the guide stem 3300. A first guide marker cap 3602 is placed onto the locking member 3400. The guide spacing sleeve 3600 is then placed onto the first guide marker cap 3602 and over the guide stem 3300. The final spacer is a second guide marker cap 3604. Once these spacers are in place the surgical instrument advance mechanism 3700 is placed onto the guide stem and the surgical instrument. The surgical instrument, the trajectory guide 3001, and a portion of the surgical instrument advance mechanism 3700 are then placed back into the scanning environment 3020.

Figure 37:
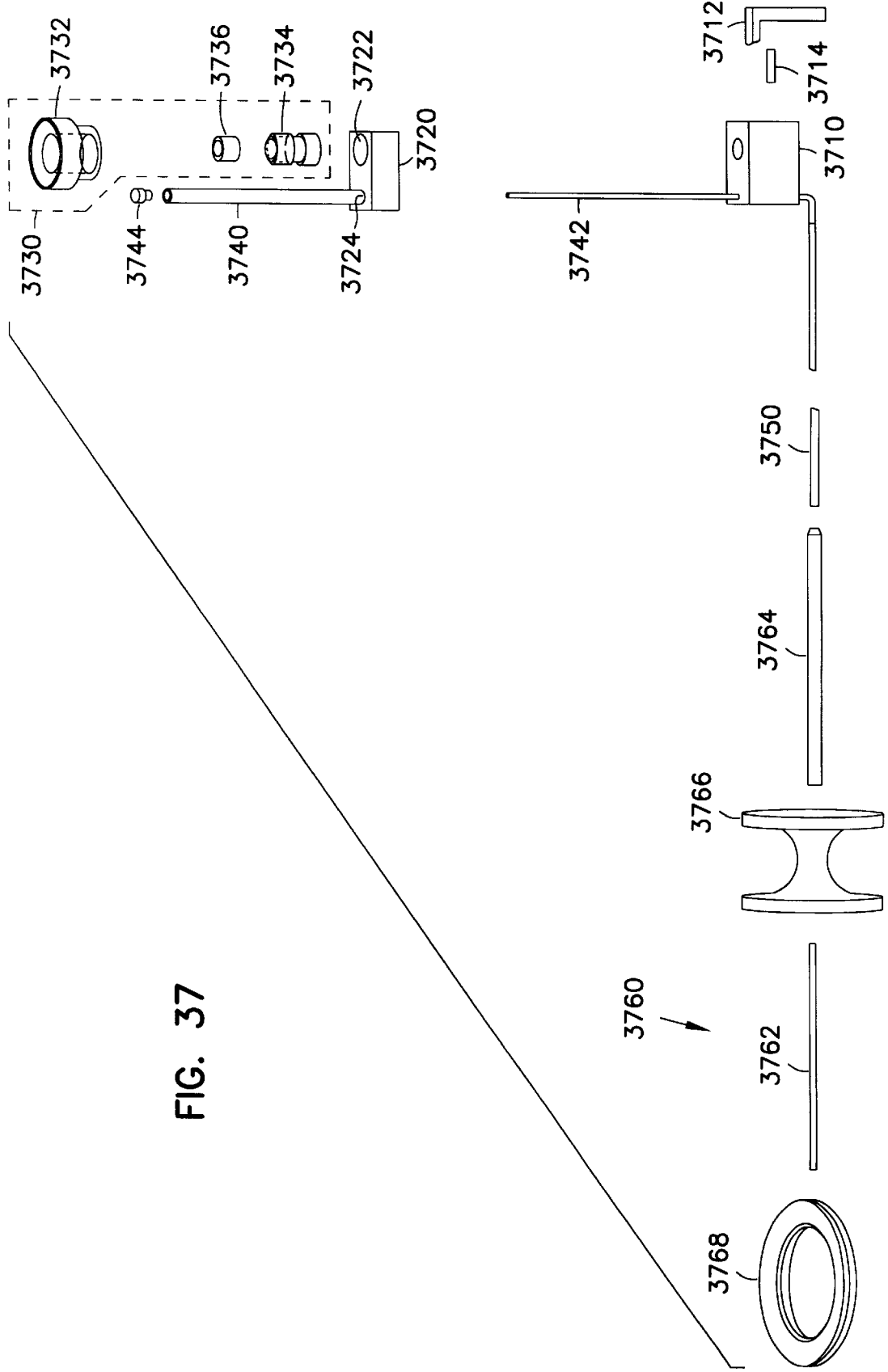
FIG. 37 is an exploded perspective view of the surgical instrument advance mechanism for use with the mechanical remotely actuated trajectory guide mechanism.

FIG. 37 is an exploded perspective view of the surgical instrument advance mechanism 3700 for use with the mechanical remotely actuated trajectory guide mechanism 3000. The surgical instrument advance mechanism 3700 includes an advancement guide mount 3710 which locks onto the detent or groove 3320 in the guide stem 3300, an instrument guide mount 3720, an instrument lock mechanism 3730, an advancement sleeve 3740, a cable 3750 and a mechanism for moving the cable 3760.

The instrument lock mechanism 3730 includes a top instrument lock 3732, a bottom instrument lock 3734, and a lock tube 3736. The lock tube 3736 is placed between the top instrument lock 3732 and the bottom instrument lock 3734. The exterior of the lock tube 3736 is surrounded and constrained by the top instrument lock 3732 and the bottom instrument lock 3734. The top instrument lock 3732 and the bottom instrument lock 3734 threadably engage one another. In operation, the instrument lock mechanism 3730 is placed over the instrument. The top instrument lock 3732 and the bottom instrument lock 3734 are moved toward each other by threading one of either the top instrument lock 3732 or the bottom instrument lock 3734 into the other of the top instrument lock 3732 and the bottom instrument lock 3734. The lock tube 3736 is elastomeric so as the top and bottom are brought closer together, the elastomeric tube bulges and captures or locks onto the surgical instrument. This also locks the surgical instrument into an opening 3722 in the instrument guide mount 3720.

The outer advancement sleeve 3740 is attached to the instrument guide mount 3720. The instrument guide mount has a second opening 3724 therein which corresponds to the opening in the advancement sleeve 3740. There is also an inner advancement sleeve 3742 which is attached to the advancement guide mount 3710 which locks onto the detent or groove 3320 in the guide stem 3300. The inner advancement sleeve 3742 fits within the outer advancement sleeve 3740. The cable 3750 is attached to one end of the inner advancement sleeve 3742. Pulling or pushing the filament or the cable 3750 allows the inner sleeve 3742 to move with respect to the outer advancement sleeve 3740.

The advancement guide mount 3710 includes an advancement lock 3712 and a locking pin 3714. The advancement lock 3712 has an end which fits into the detent or groove 3320 in the guide stem 3300. The locking pin 3714 keeps the advancement lock 3712 in place. After the advancement guide mount 3710 is locked into place it does not move with respect to the guide stem 3300.

The mechanism for moving the cable 3760 includes an inner sleeve 3762, an outer sleeve 3764, a syringe ring 3766, and a thumb ring 3768. The cable is attached to one end of the inner sleeve 3762. By moving the thumb ring 3768 with respect to the syringe ring 3766, the inner sleeve 3762 moves with respect to the outer sleeve 3762 and in turn moves the cable 3750 on the other end. Moving the thumb ring 3768 away from the syringe ring 3766 causes the instrument guide mount 3720 to move toward the advancement guide mount 3710. Since the surgical instrument is attached to the instrument guide mount 3720, the surgical instrument is advanced into the patient. When the thumb ring 3768 is moved toward the syringe ring 3766, the surgical instrument is withdrawn from the patient body. The the thumb ring 3768 and the syringe ring 3766 are positioned outside the scanning environment 3020 so that the surgeon or technician can control the advancement or withdrawal of the instrument into and out of the trajectory guide in the scanning environment. In the first or actual trajectory guide 3001 the outer advancement sleeve 3740 includes markings thereon indicative of units of measure such as centimeters, millimeters, or inches. On the second trajectory guide 3002 the the outer sleeve 3762 includes markings thereon indicative of units of measure such as centimeters, millimeters, or inches. In this way the surgeon can advance the surgical instrument from outside the environment by moving the thumb ring 3768 toward the syringe ring 3766 a certain number of units of measure to get the surgical instrument relatively close to the target. The surgeon can advance the instrument to the target while watching the surgical instrument from outside the environment using an available scanning apparatus. The needle can be advanced to just the exact position of the body organ.

It should be noted that this advancement mechanism can be adapted for use with any base or for use with any trajectory guide. For example, a hydraulic mechanism for moving the guide stem 3300 from side to side, which is discussed below, could be used with this advancement mechanism. In addition, this advancement mechanism can be used with any base or on any variation of the trajectory guide.

Hydraulic Actuator for Remote Actuation and Control—Second Embodiment

Figure 10:
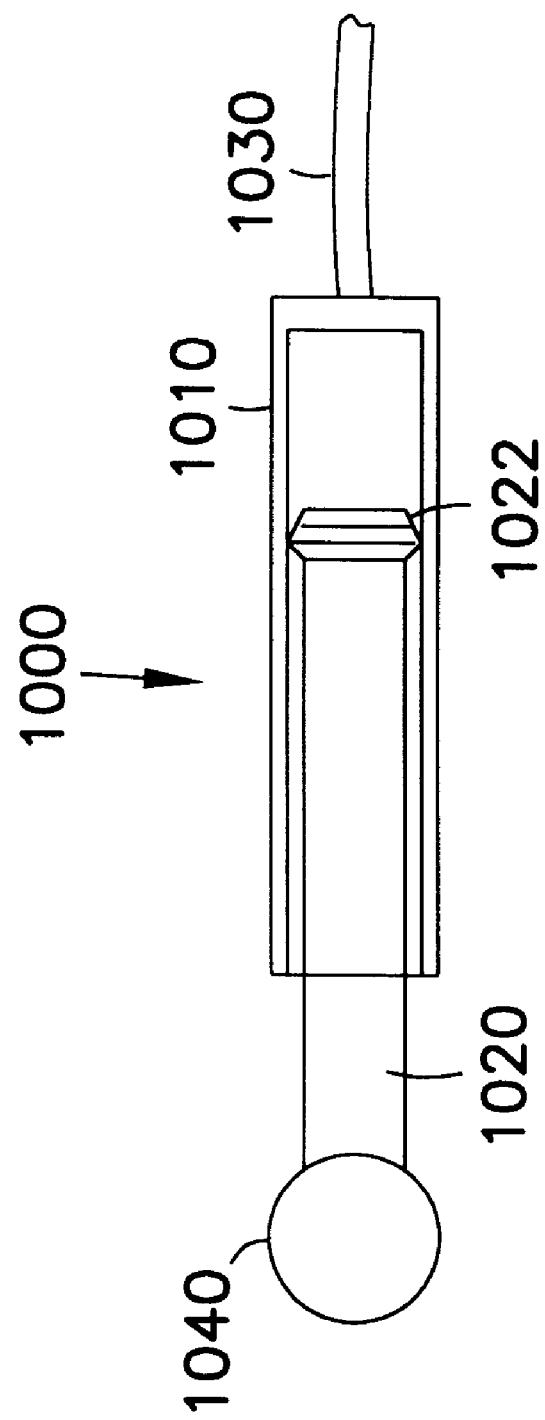
FIG. 10 is a side view of a hydraulic actuator used to move the guide stem of the trajectory guide.

Now turning to FIG. 10, a hydraulic actuator 1000 is shown. The hydraulic actuator 1000 includes a cylinder 1010, a plunger 1020, a hydraulic line 1030 and an attachment mechanism 1040. The plunger 1020 has a seal 1022 located on one end of the plunger. The seal 1022 prevents the flow of liquid from the cylinder to a position past the plunger 1020. When fluid is forced or fluid pressure is placed on the fluid in the hydraulic line 1030, the fluid passes into the cylinder 1010. When more fluid is passed into the cylinder 1016, the plunger 1020 moves in a direction to allow for an increased volume between the seal 1022 and the bottom of the cylinder 1010. If the fluid in the hydraulic line 1030 is drawn away from the cylinder, the plunger and the end with the seal 1022 move closer to the bottom of the cylinder 1010 so that a smaller volume is formed within the cylinder. As a result, the plunger 1020 moves in response to fluid being pressed into the cylinder 1010 or being removed from the cylinder 1010. The attachment mechanism 1040 is used to attach the plunger to the guide stem or other surgical instrument that needs to be moved or adjusted. The attachment mechanism 1040 is attached to the plunger 1020. In this instance, the attachment mechanism 1040 is a hoop which can be used to encircle the guide stem 240. Other attachment mechanisms could also be used such as hooks or clamps. The hoop arrangement shown allows the guide stem to be moved or adjusted when the plunger 1020 moves in and out of the cylinder 1010. All of the pieces of the hydraulic actuator 1000 can be made of a material that is not affected by a magnetic field. A hydraulic cylinder such as the one shown can then be used in an MRI scanning environment. It is contemplated that other actuators could be formed and made from non-magnetic parts so they too could perform in an MRI environment.

Figure 11:
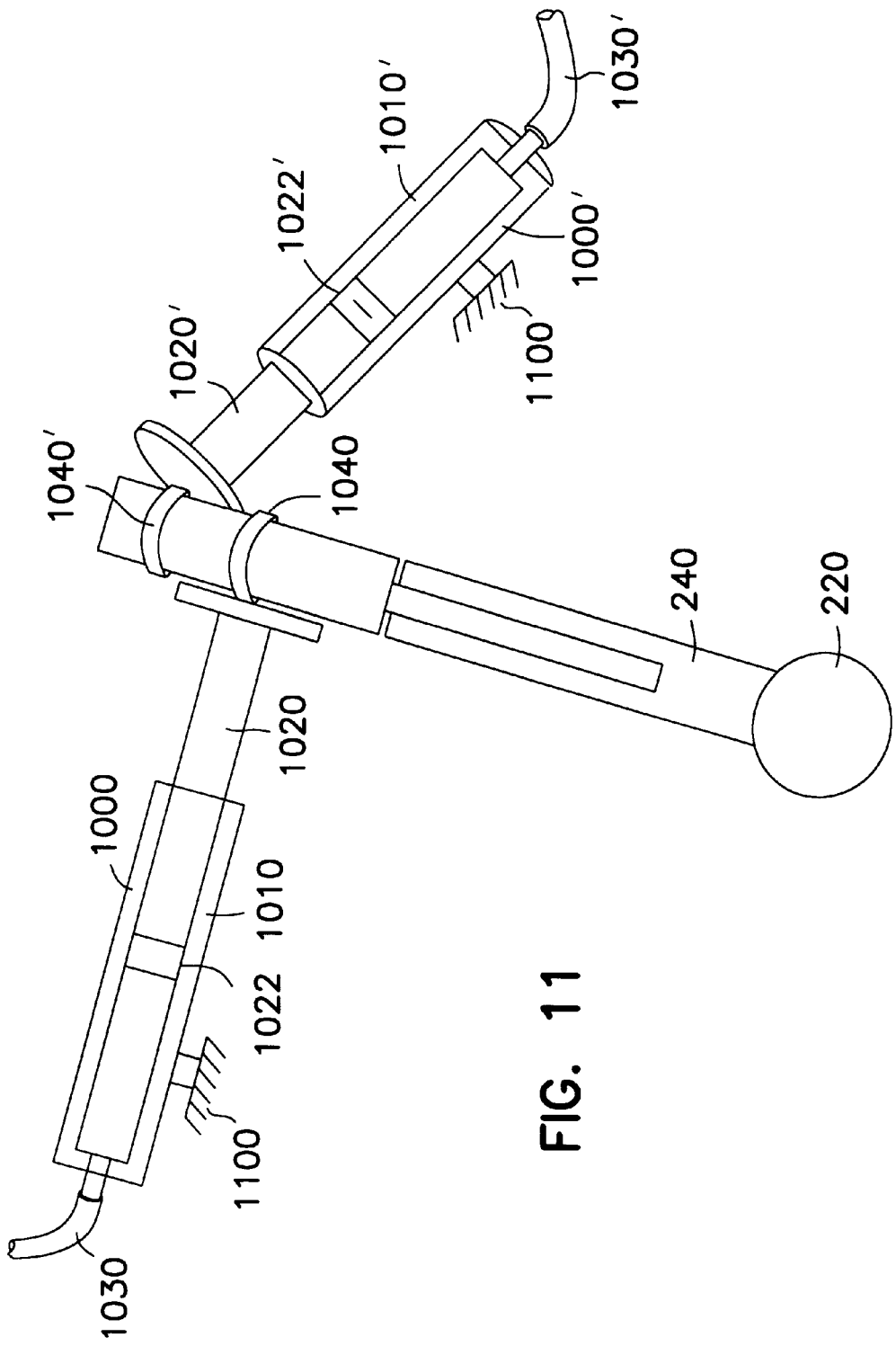
FIG. 11 is a top view of a guide stem of a trajectory guide having two hydraulic actuators attached to the guide stem.

FIG. 11 is a top view of a guide stem 240 of a trajectory guide 100 which has two hydraulic actuators 1000 and 1000' attached thereto. Hydraulic actuators 1000 and 1000' one used to move the guide stem when it is remote from the surgeon. The attachment mechanism 1040 from the actuator 1000 passes around the guide stem of the trajectory guide 100. Similarly, the attachment mechanism 1040' is also attached around the guide stem 240. The plunger 1020 and the plunger 1020' are at approximately 90° with respect to each other. Each of the plungers can then move the guide stem 240 to adjust its trajectory toward a target within the human body. Each of the hydraulic cylinders 1010 and 1010' is attached or affixed to a solid base 1100. As shown in FIG. 11, both of the cylinders 1010 and 1010' are attached to a base 1100 which is shown schematically. Any number of arrangements can be used to attach the cylinders to a base 1100. For example, it is contemplated that the base 1100 could be the base 210 of the trajectory guide 100. It is also contemplated that the base 1100 could be a ring configuration which holds the cylinders 1010 and 1010' solid with respect to the guide stem 240.

In operation, the hydraulic cylinders 1000 and 1000' are attached to the guide stem 240 by the attachment mechanism 1040 and the attachment mechanism 1040'. The guide stem 240 can then be moved by moving either plunger 1020 or 1020'. By moving these plungers, the attitude or the trajectory of the guide stem can be changed before the locking member is used to lock the movable member into position. Once the hydraulic cylinders 1000 and 1000' move the guide stem 240 to a position in line with the target, the patient is moved to a point where the locking member can be used to immobilize the movable member. The hydraulic system described thus far is used to position the guide stem so that a trajectory may be selected.

Remote Actuation and Control—Second Preferred Embodiment

Figure 19:
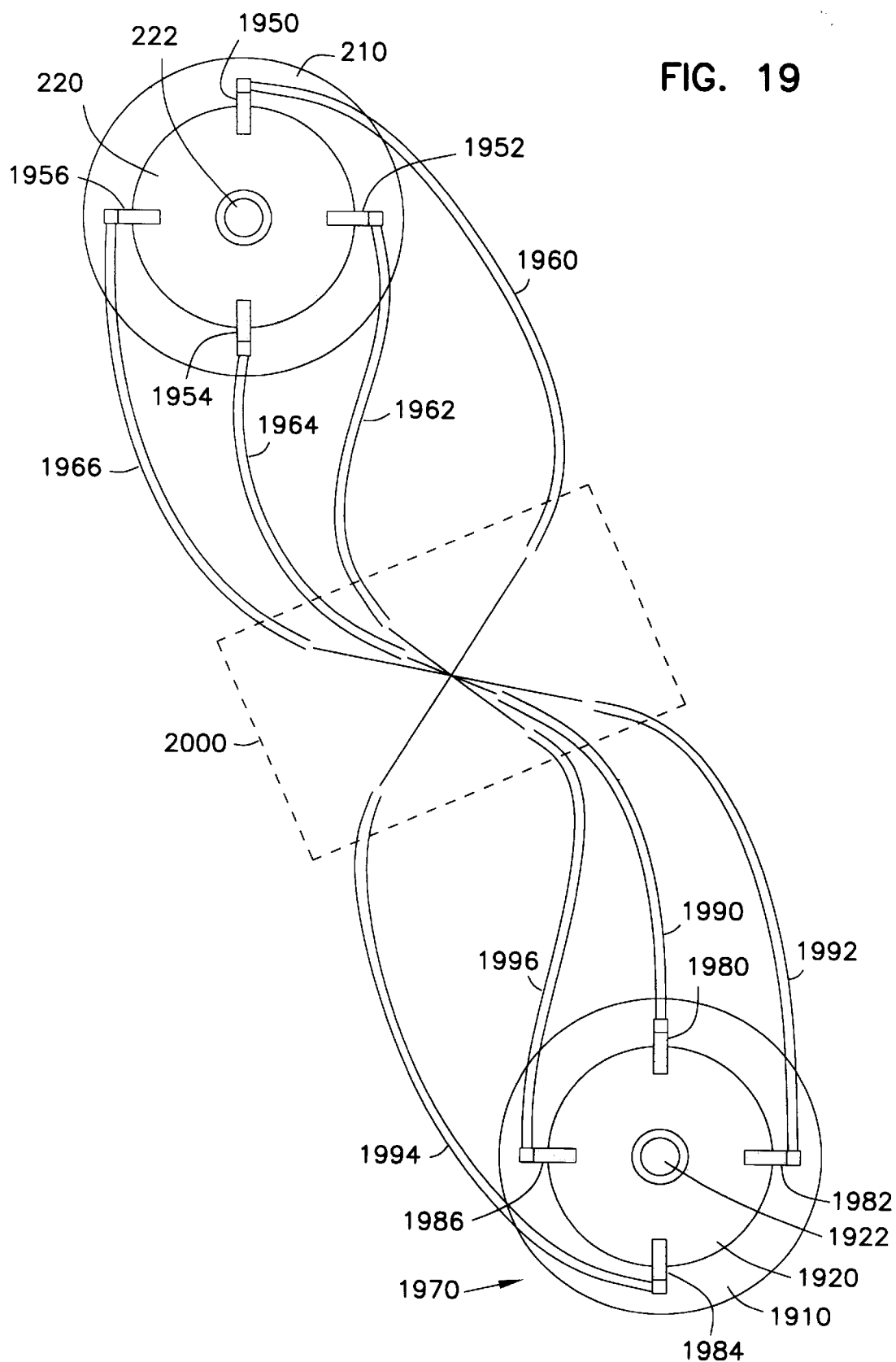
FIG. 19 is a remotely controlled actuator mechanism used to control movement of the movable member associated with the patient

FIG. 19 shows a remotely controlled actuator mechanism which is used to control the movement of the movable member 220 associated with the trajectory guide system 200. To remotely control the movable member 220 there is provided a duplicate or remote movable member 1920 having an opening 1922 therein. The movable member 220 has a series of subactuators 1950, 1952, 1954, and 1956 which are attached to the movable member 220 and have one end embedded in a base of a trajectory guide. The base 210 shown in FIG. 19 is schematically depicted as a ring to which the subactuators 1950, 1952, 1954, and 1956 are attached. Attached to each subactuator is a hydraulic line. Attached to subactuator 1950 is hydraulic line 1960, attached to subactuator 1952 is hydraulic line 1962, attached to subactuator 1954 is hydraulic line 1964, and attached to subactuator 1956 is hydraulic line 1966. The subactuators 1950, 1952, 1954, and 1956 are positioned so that the movable member 220 can be adjusted in or about at least two orthogonal axes. It should be noted, that only two subactuators are really required to produce movement about two orthogonal axes. Four are shown in FIG. 19. Four are used since many of the movements are very small and precise.

Therefore it is advantageous to have one subactuator offset another subactuator to effectuate the precise, small motions of the movable member 220. The movable member 220 is associated with the patient.

Attached to the movable member 220 and the base 210 is a duplicate or remote actuator 1970. The remote actuator 1970 includes movable member 1920 and a ring 1910 or base in which the movable member 1920 is able to rotate. Attached to the movable member 1920 are a series of four subactuators 1980, 1982, 1984, and 1986. A hydraulic line 1990 is attached to subactuator 1980. Similarly, a hydraulic line 1992 is attached to subactuator 1982, hydraulic line 1994 is attached to subactuator 1984 and hydraulic line 1996 is attached to subactuator 1986. The hydraulic lines 1960, 1962, 1964, and 1966 are attached to an intermediary actuator device 2000. Also attached to the intermediary actuator device 2000 are hydraulic lines 1990, 1992, 1994, and 1996. Within the intermediary actuator device 2000 the hydraulic line associated with a subactuator on a patient is attached to an opposite hydraulic subactuator on the remote 1970. In other words, the hydraulic line 1960 associated with subactuator 1950 is attached to hydraulic line 1994 associated with subactuator 1984. Similarly, hydraulic line 1964 is attached to hydraulic 1990, and hydraulic line 1966 is attached to hydraulic line 1992. By attaching the hydraulic lines to subactuators that are opposite on the remote when compared to the movable member 220, movement of the movable member 1920 mirrors movement of the movable member 220. In other words there is a direct relation between moving movable member 1920 on the remote device and moving the movable member 220 associated with the patient.

Figure 20:
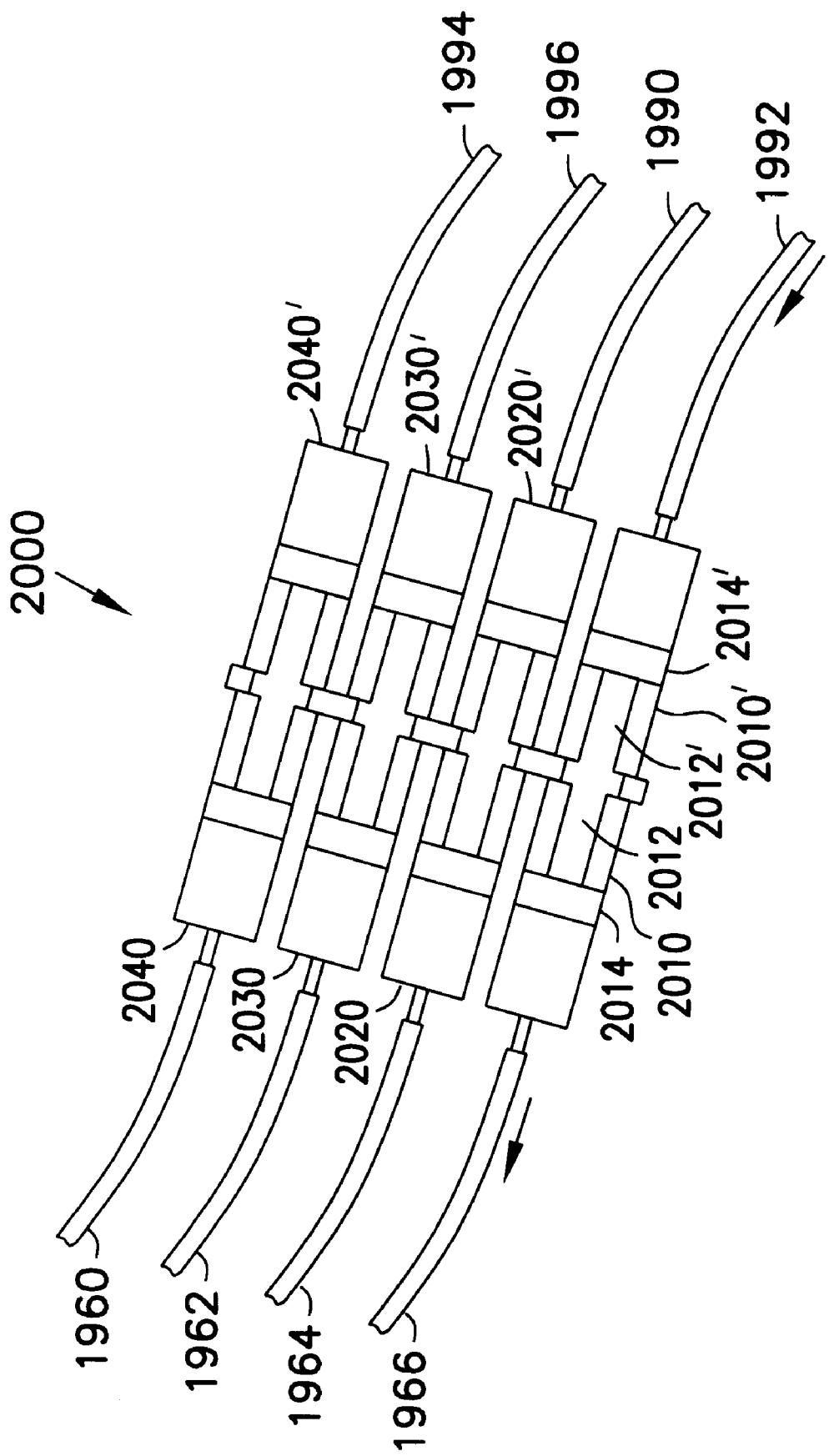
FIG. 20 shows the set of intermediary hydraulic rams used to interconnect the movable member associated with the patient and the movable member associated with remote control.

FIG. 20 shows the intermediary actuator device 2000. The intermediary actuator device 2000 includes a set of intermediate double hydraulic rams which are used to interconnect the movable member 1920 and the movable member 220. As shown in FIG. 20, hydraulic ram 2010 is removably attached to another identical hydraulic ram 2010', with identical subunits 2012' and 2014'. Four hydraulic rams 2010, 2020, 2030, and 2040 are thus removably attached to identical mirror-related hydraulic rams 2010', 2020', 2030', and 2040', hence four double hydraulic rams. One such double hydraulic ram will be described. The remaining double hydraulic rams are the same. Intermediary actuator device 2000, including four double hydraulic rams, each of which comprises dual, mirror-related hydraulic rams, includes hydraulic rams 2010 and 2010' that include shafts 2012 and 2012' respectively. On each end of shafts 2012 and 2012' are seals 2014 and 2014' respectively. The seals 2014 and 2014' can also be thought of as plungers. The seals 2014 and 2104' keep hydraulic fluid on the away from the shafts 2012 and 2012' and outside of the plungers, 2014 and 2014'. For example, the hydraulic rams 2010 and 2010' have no or are devoid of fluid in the area adjacent to cylinders 2012 and 2012'. The seals 2014 and 2014' maintain the fluid on the outside of the cylinders 2012 and 2012'. Fluid is depicted by the gray areas on the outside of the seals 2014 and 2014'.

In operation, when fluid is forced toward the hydraulic ram 2010 in the hydraulic line 1992 due to a movement of microactuator 1982 (FIG. 19), the cylinders 2012' and 2012 and the seals 2014' and 2014 move in the direction of the fluid pressure. In other words, when the fluid is moved in the direction shown by the arrow adjacent hydraulic line 1992, additional fluid is forced into the hydraulic ram 2010' near the seal 2014' to which the hydraulic line 1992 is added and this forces the cylinders 2012' and 2012 and the seals 2014' and 2014 to move in the same direction as the arrow. The other double hydraulic rams 2020/2020', 2030/2030', and 2040/2040' work in the same manner.

Advantageously, the intermediary actuator device 2000 provides a break in the various hydraulic lines so that the movable member 220 and base 210 are disposable, while the movable member 1920 and the base 1910 which are used to control the trajectory guide associated with the patient, can be reused. The intermediary actuator device 2000 is also part of the reusable portion. In other words, a new sterile movable member 220 and base 210 as well as sterile hydraulic line 1960, 1962, 1964, and 1966, and hydraulic rams 2010, 2020, 2030, and 2040 can be used on a patient. After the use, the movable member 220 and base 210 and the hydraulic lines 1960, 1962, 1964, and 1966 can be discarded. A new assembly including movable member 220 and base 210 and the associated hydraulic lines and hydraulic rams can then be attached to the appropriate mirror-related hydraulic rams 2010', 2020', 2030', and 2040' of the intermediary actuator device 2000 for the next use.

Of course it is not necessary that hydraulics be used. A small mechanical device can also work equally well. In such a design, hydraulics would be replaced by wires or other filaments that would translate the motion at the remote end to the device in are associated with the patient. An MR-compatible deflection device could also be used. The deflection device is a laminated composite material including at least one piezo-electric layer.

Now turning to FIGS. 12, 13 and 14, a hydraulic system for introduction or insertion of a surgical instrument through the opening 242 in the guide stem 240 and through the opening 222 in the movable member 220 will now be discussed.

Figure 12:
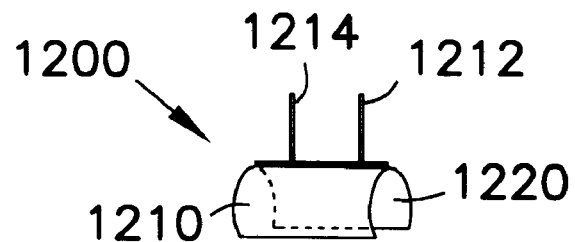
FIG. 12 is an isometric view of a first clamp for holding a hydraulic cylinder.

FIG. 12 shows a clamp 1200 which is used to clamp onto one of either the surgical instrument 1400 or the guide means 240. In FIG. 14, clamp 1200 is attached to the surgical instrument, 1400. The clamp 1200 includes a first wing 1210 and a second wing 1220. The first wing 1210 and the second wing 1220 have an arcuate shape that conforms with either the surgical instrument 1400 or the outside body of the guide means 240 The wings 1210 and 1220 are spring loaded such that the wings 1210 and 1220 tend to urge toward each other. One wing 1210 includes a C-shaped holder 1212 and a P-shaped tab 1214. The C-shaped holder 1212 holds a portion of a plunger 1020 of a hydraulic actuator 1000. The tab 1214 provides an end stop for the plunger 1220. The C-shaped holder 1212 also serves to limit the range of motion of the end of the plunger 1220. The end of the plunger has a disk-shaped end 1025.

Figure 13:
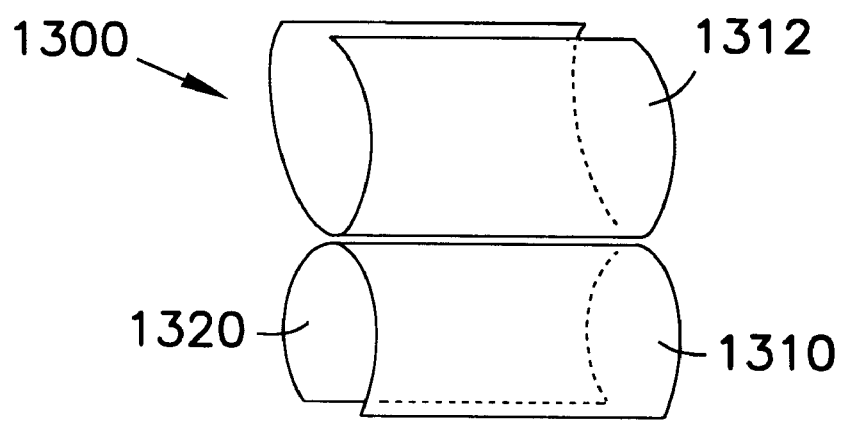
FIG. 13 is an isometric view of a first clamp for holding a hydraulic cylinder.
Figure 14:
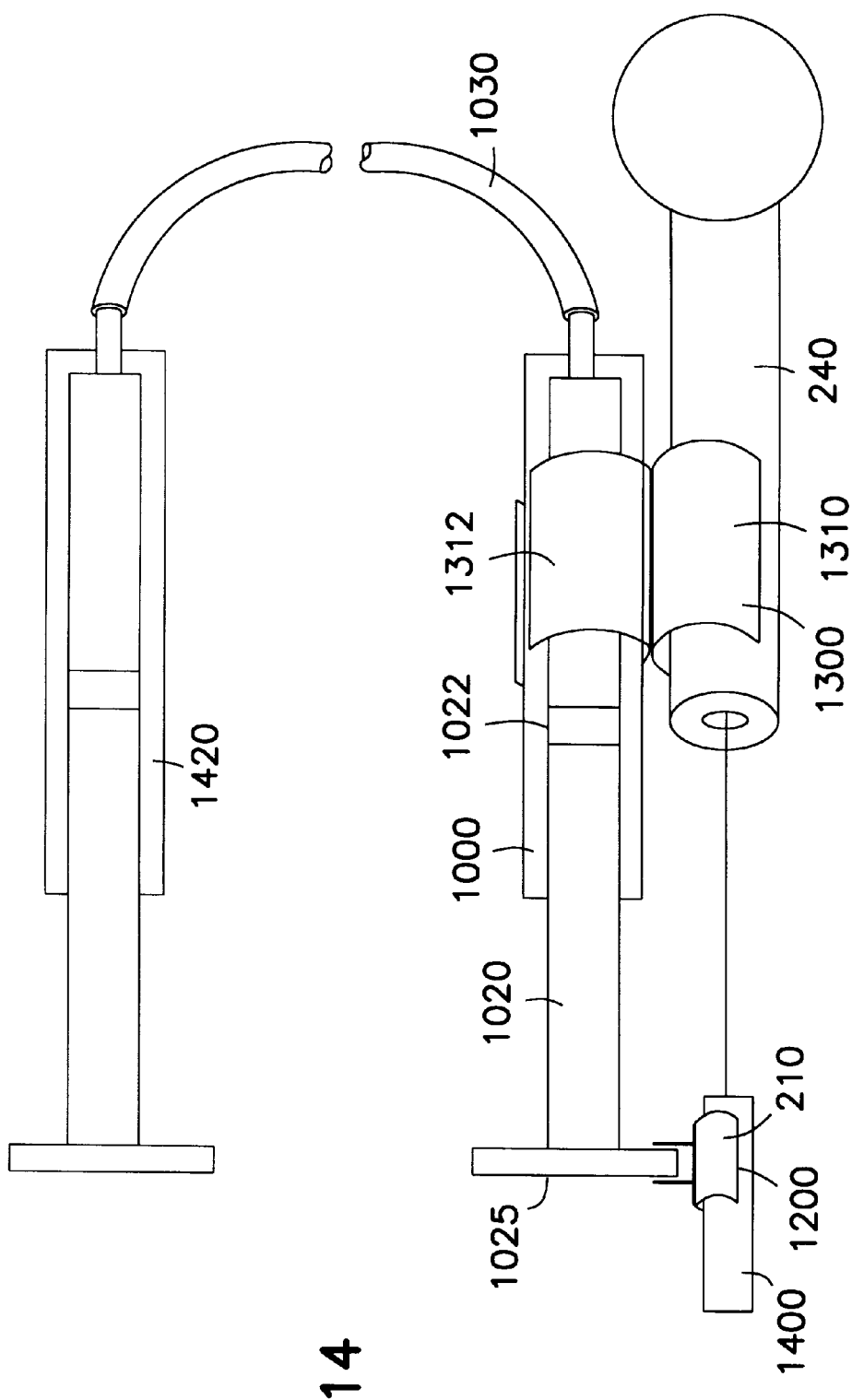
FIG. 14 is an exploded isometric view of the first clamp and the second clamp for holding a hydraulic cylinder onto a surgical instrument and a trajectory guide.

Now turning to FIG. 13, there is shown a second clamp 1300. The second clamp 1300 includes a first wing 1310 and a second wing 1320. The first wing 1310 and the second wing 1320 are assembled such that the wings urge toward one another. The shape of the wings 1310 and 1320 conform the clamp to the outer body of the guide means 240. The clamp 1300 also includes a holder 1312 which is used to hold the cylindrical body 1010 of the hydraulic cylinder 1000.

In operation, the hydraulic system for inserting or introducing a surgical instrument 1400 into the trajectory guide 100 is used as described below. Clamp 1200 is applied to one of either the surgical instrument 1400 or the guide means 240. The other clamp 1300 is applied to the other of the surgical instrument or the guide means 240. As shown in FIG. 14, the clamp 1200 is applied to the surgical instrument 1400 while the clamp 1300 is applied to the guide means 240 of the trajectory guide 100. It should be noted that the clamps 1200 and 1300 are made of a lightweight material and furthermore are made of a material that can be used in an MR or magnetic environment. Once the clamps are put in place, a hydraulic cylinder is attached to the holder 1212 of clamp 1200 and to the holder 1312 of clamp 1300. The holder 1212 grips or holds the plunger 1220 while the holder 1312 holds the cylinder 1010 of the hydraulic actuator 1000. Once the clamps 1200 and 1300 have been placed and once the hydraulic actuator 1000 has been placed onto the clamps, fluid can be passed into the hydraulic cylinder 1010 or removed from the cylinder 1010 to move the clamps 1200 and 1300 with respect to one another. As shown in FIG. 14, fluid would be removed from the cylinder 1010 via hydraulic line 1030 which would draw the clamp 1200 attached to the surgical instrument 1400 toward the clamp 1300 on the guide stem 240. This would result in an insertion of the surgical instrument 1400 into the guide means and into the body of a patient. It should be noted that the clamps must be lightweight so as not to produce an excessive torque on the guide means 240 or the surgical instrument 1400. If too large a torque is placed on the guide means or the surgical instrument 1400, the guide means may be repositioned out of alignment due to torque placed on the guide stem 240 or the surgical instrument 1400. In addition, it should be noted that it is not necessary to use clamps 1200 and 1300. The holders 1212 and 1312 as well as the tab 1214 could be formed integral with the surgical instrument 1400 and the guide stem 240. It is also contemplated that a pair of clamps could be used to prevent a torque in a sideways mode or bending mode. In other words, if two hydraulic actuators 1000 were used side by side, the surgical instrument 1400 would be less likely to bend with respect to the guide stem 240.

In an actual operation using the hydraulically controlled guide, the position of the tip of the surgical instrument with respect to the target is monitored or tracked in real time using fast MR imaging techniques, so-called MR fluoroscopy. The position of the plunger and therefore the surgical instrument can be controlled through a precision fluid pump in a remote location inside or outside of the MR magnet. This controlling mechanism can also be a manual control 1420, as shown in FIG. 14, or may be interfaced to a computer that may also control the advancement of withdrawal of the hydraulic assembly can be bidirectional for the purpose of both insertion and extraction of a surgical instrument within a targeted tissue in the MR imaging volume. It should be noted that a manual controller may include one or more hydraulic actuators. In other words, one may move small amounts of hydraulic fluid for fine adjustment while the other may move large amounts of hydraulic fluid for course adjustment.

It should be noted that two embodiments of remote actuation of trajectory guides have been discussed. This invention covers many other types of remote actuation which could be substituted for either of the two embodiments discussed so far. In other words, variations could be made to the two remote actuation devices discussed so far that would be within the scope of this invention.

Stage

Figure 8:
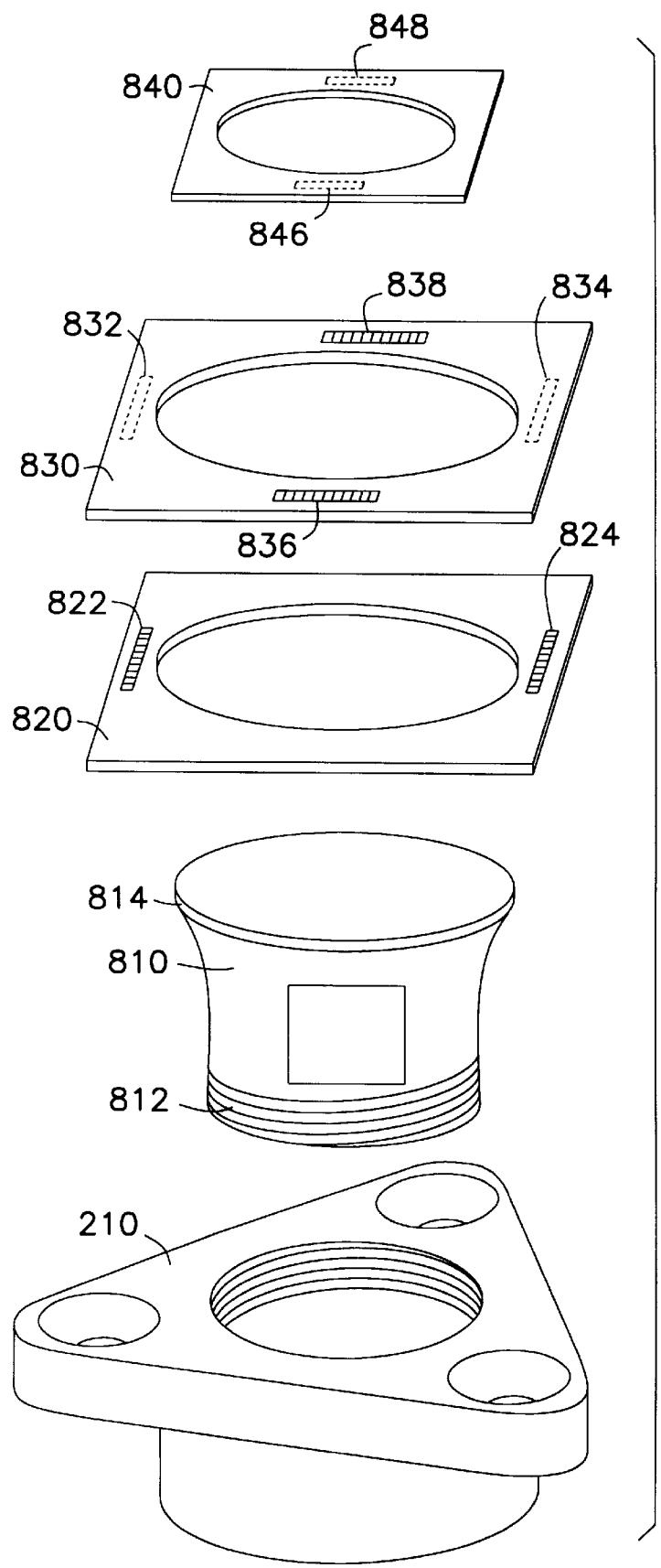
FIG. 8 is an exploded view showing a stage for attachment to the base of the trajectory guide.

The base 210 of the trajectory guide 200 can also be fitted with a stage 800 as is shown in FIG. 8. The stage 800 is used to move the guide opening within a plane that intersects the center line of the trajectory line 260 defined by the opening 242 in the guide member or stem 240 and the opening 222 in the movable member 220. FIG. 8 shows an exploded view of a stage 800 for attachment to the base 210 of the trajectory guide (shown in FIG. 2). The stage 800 includes a suspension tube 810, a first or lower suspended platform 820, a middle or second suspended platform 830 and an upper or third suspended platform 840. The suspension tube 810 includes an outside thread which mates with the inner thread of the base 210. The outside thread is located near one end 812 of the suspension tube. On the other end of the suspension tube is another outside threaded portion 814 which mates with inside threads formed in the first or lower suspended platform 820. The suspension tube 810 has a flanged body which allows the movable member and attached guide stem 240 to have freedom of motion within the suspension tube 810. The first suspended platform 820 is threadably attached to the threaded end 814 of the suspension tube 810. The first suspended platform includes geared areas 822 and 824. The geared areas 822 and 824 mesh with geared areas 832 and 834 of the second or middle suspended platform 830. The second or middle suspended platform 830 is attached to the first or lower suspended platform 820 via the geared areas 822, 824, 832 and 834. The result is that the middle or second suspended platform is able to move with respect to the first suspended platform 820 in a plane that includes the geared areas 822, 824, 832 and 834. The second suspended or middle platform 830 also includes geared areas 836 and 838 which enmesh with geared areas 846 and 848 of the third or top suspended platform 840. The geared areas 836, 838, 846 and 848 allow the third suspended platform 840 to move with respect to the second suspended platform 830. The movement of the third suspended platform 840 with respect to the first suspended platform 830 is transverse in a direction transverse to the movement of the second suspended platform 830 with respect to the first suspended platform 820. The stage is useful in allowing for slight adjustments when using the trajectory guide means 100. Sometimes when the trajectory guide means is used, the instrument 1400 is placed at the target within the body only to discover either that the target has shifted slightly due to tissue changes, such as edema or swelling, or that the anatomic target selected from the MR or other images is not, in fact, the physiological target. In such situations, the trajectory may be proper, however, it is linearly displaced slightly. By moving the trajectory guide means in a linear fashion using the stage 800, the trajectory is maintained. A parallel trajectory is thus formed so that the surgical instrument can be re-inserted into the human body and hit a target. There are numerous types of gearing mechanisms that can enable the stage to operate, with linear, curvilinear or other movements, to reposition the trajectory in a parallel fashion.

Figure 9:
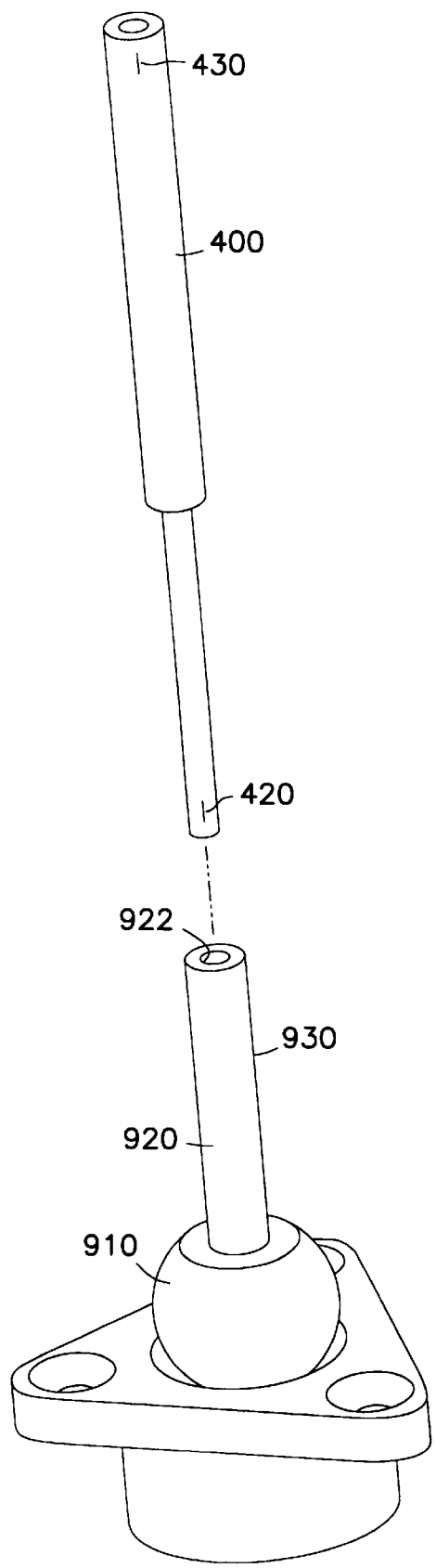
FIG. 9 is an exploded isometric view of another preferred embodiment of the movable member of the trajectory guide and a positioning stem.

FIG. 9 shows an exploded isometric view of a movable element 920 that has a ball end 910 and a guide stem end 930. The movable element 920 fits within the base 210 and locking member 230. As shown, the movable element 920 has a passageway 922 therein which traverses the length of the movable element 920. FIG. 9 also shows a positioning stem 400. The positioning stem 400 is dimensioned so that it fits snugly within the passageway 922. The positioning stem includes the first locator 420 and the second locator 430 but has no threaded end. In order to correctly position the movable element 920, the positioning stem 400 is placed into the passageway 922. The movable element 920 with the positioning stem 400 is moved until the computer 102 determines that the line formed by the first locator 420 and the second locator 430 align with the target 270. Once alignment is achieved, the locking member 230 is used to lock the movable element 920 into place. Once locked, the positioning stem 400 is removed. Passageway 922 then corresponds or is collinear with the trajectory 260 to the target 270 within the patient.

Computer Control

The remote actuators can be controlled by a computer program that, once calibrated, can be used to perform the alignment, and even the introduction of a device through the guiding stem. Several methodologies for enabling this are available. Using the MR imaging coordinates of a target, and the MR imaging coordinates of the two or more micro coils on the alignment or guiding stem, a computer program can be written to direct the remotely actuated trajectory guide to align with the target. One essential component of such a software program is the ability of the system to accurately and efficiently measure both MR position on the images and physical position in the bore of the MR scanner. Various linear transformations are required to correctly reference all positional points of reference and achieve precise spatial registration. In addition, geometric distortions inherent in the MR images need to be quantified and corrected.

Figure 21:
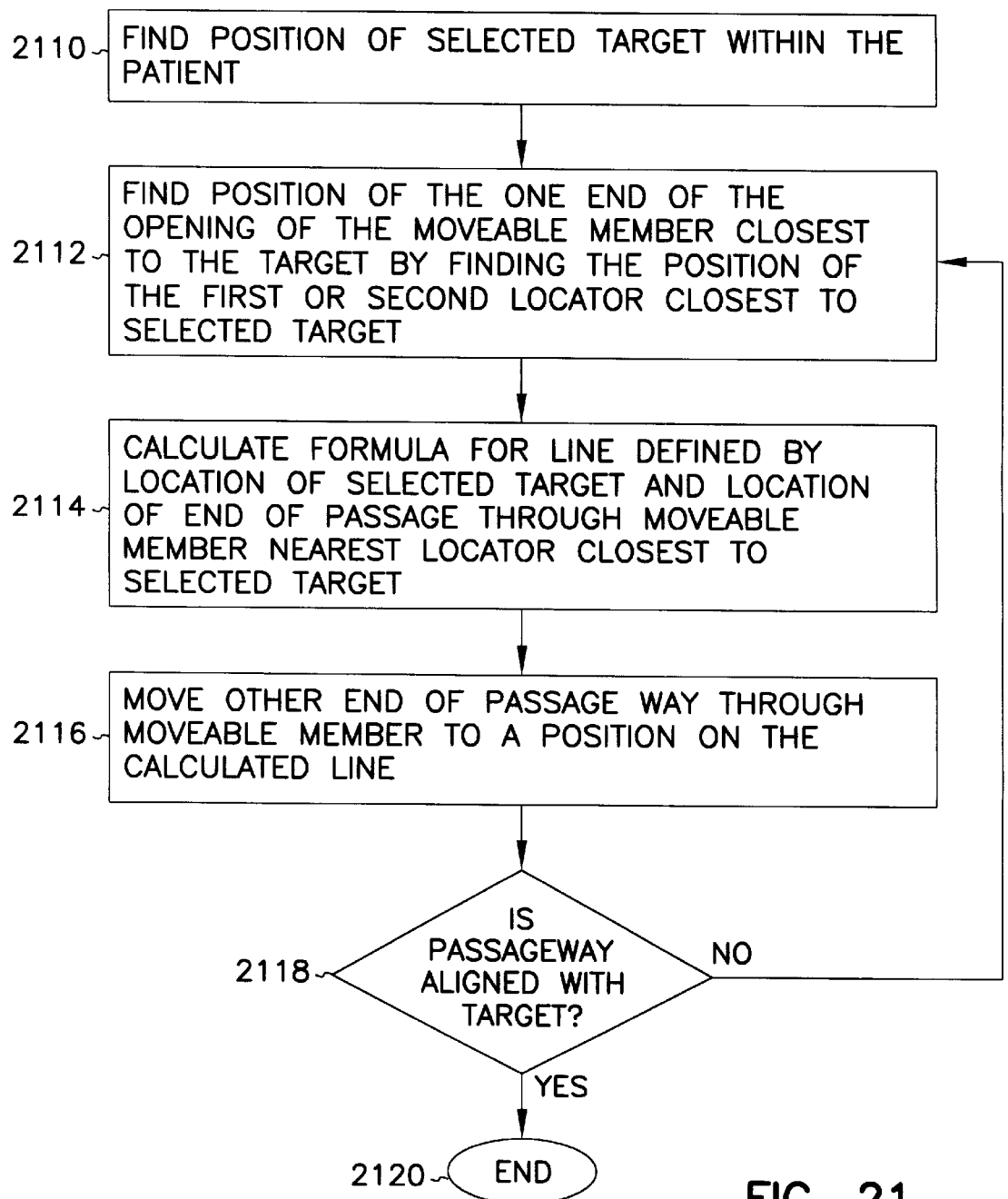
FIG. 21 is a flow chart of the software program used to control movement of the movable member.

FIG. 21 shows a flow-chart of computer software used to implement computer control of the alignment of the opening 222 within the movable member 220 with a selected target 270 within the body. The first step is to find the position of the selected target within the patient, as depicted by reference numeral 2110. The position of the target 270 within the patient may be in a coordinate system specific to the nuclear magnetic resonance system and may have to be converted to another coordinate system. For example, a coordinate system associated with a particular nuclear magnetic resonance imaging system may have to be converted into polar coordinates or into Cartesian coordinates with an "x", "y" and "z." The next step is to find the position of one end of the passageway with respect to the first or second locator which is closest to the selected target, as denoted by reference number 2112. Many times the first or second locator will be associated with or co-linear with one end of the opening 222 in the movable member 220. At other times, the first or second locator will be offset from the opening. Therefore, the position of the first or second locator will have to be mathematically moved or corrected so that it corresponds to the position of one end at the opening 222 and the movable member 220. The next step is to determine the formula for a line defined by the selected target within the patient and the end of the opening 222 and the movable member 220. Once the formula of the line is known and the distance between the first locator and second locator is known, the exact position of the first or second locator most distant from the selected target can be calculated. If the most distant first or second locator is offset from the opening or a line co-linear with the passageway through the movable member, this too can be mathematically corrected for. The next step is to move the movable member such that the second locator is in the calculated or determined position, as depicted by reference numeral 2116. After the second locator is in its determined position, the system checks whether the opening is aligned with the target, as shown by the decision box carrying the reference numeral 2118. If the passageway is not aligned with the target, the movable member is repositioned, or the step depicted by reference numeral 2112 is repeated and steps 2114 and 2116 are repeated. If the passageway is aligned with the target, the program ends, as depicted by reference numeral 2120. After the adjustment of the movable member 220 is complete, a clamp or other means is used to firmly affix the movable member so that a surgical instrument can be passed through the opening 222 in the movable member.

Base with RF Coil

Figure 15:
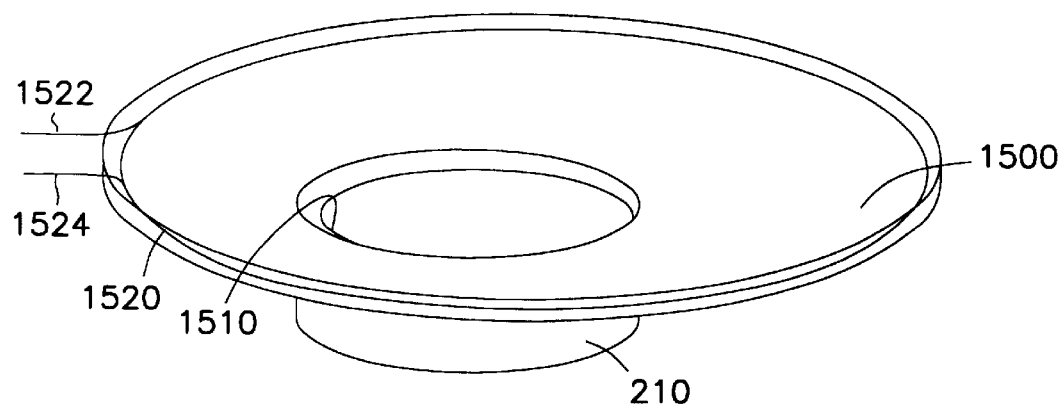
FIG. 15 is a perspective view of an attachment to the base of the trajectory guide.

FIG. 15 shows an attachment 1500 to the base. The attachment is flat, may be rigid or flexible, may be round or other geometric or non-geometric shape. The attachment is designed to be screwed into the base much like the locking component. The attachment 1500 has a threaded end 1510 which engages the base member 210. Within the attachment 1500 is a radio frequency coil 1520 for imaging the subjacent tissues by using an MR scanner. Leads 1522 and 1524 from the coil 1520 are attached to the MR scanning system. In the figure, the coil 1520 is circular, but it is not limited to that design. There are numerous different coil designs that could be used to enable the detection of signals from the subjacent tissues. Not shown in the figures are the typical preamplifier and other electrical components required to enable the coil 1520 to function. In one embodiment, these components could be designed on a silicon chip such that they are quite small and only two wires would need to exit the attachment for connection to the MR scanner. In another embodiment, the electrical components could be physically included within the attachment in a more traditional manner. In either embodiment, both imaging and spectroscopy of the subjacent tissue could be enabled in order to monitor the deliver of a therapy, such as a drug or a thermal therapy. In addition, the coil or coils included in the attachment could function in conjunction with a coil or coils on a delivery device implanted in the subjacent tissue as described above, when using the guide stem and movable member.

Figure 16:
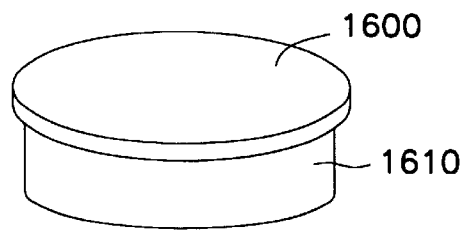
FIG. 16 is a perspective view of a cap and plug for use with the base of the trajectory guide.

Turning to FIG. 16, a cap 1600 with a plug 1610 may be used to seal the base 210 in the event that it is desirable to leave the base 210 in place. Typically, the cap 1600 would include a plug 1610, so as to fill the space of the surgical opening to prevent escape of tissues or bodily fluids. The cap 1600 and plug 1610 can be attached to the base by any number of means, such as a threaded connection or force fit connection. It is also envisioned that the cap and plug could be used in conjunction with an implantable medical device, such as a drug delivery device, in which case the cap 1600 and plug 1610 might include a reservoir and pump mechanism. In another embodiment, the cap 1600 and plug 1610 might serve as a connector to the drainage tubing of a cerebrospinal fluid shunt, in the case where the trajectory guide were used to enable the placement of a shunt catheter into the cerebral ventricles.

Small Incision Procedure

Currently, many surgical procedures are now performed through a twist drill hole of approximately 2 mm. This is much smaller than the burr hole previously discussed above. If a 2 mm hole is used in a surgical procedure there is no requirement for a suture at the end of a procedure. A drill hole of this small size can be made with a minor incision or scalp or upper body area and with minimal trauma. Many times the small hole approach is used when performing biopsies on areas that present a relatively large target within the patient. In other words, the use of a 2 mm hole is typically used in applications where the target is relatively large. A fixation device is attached to a therapy table. The fixation device may include a flexible snake which are easily repositioned by hand or by remote control. Once a remote button is released, a snake retains its last position.

Figure 22:
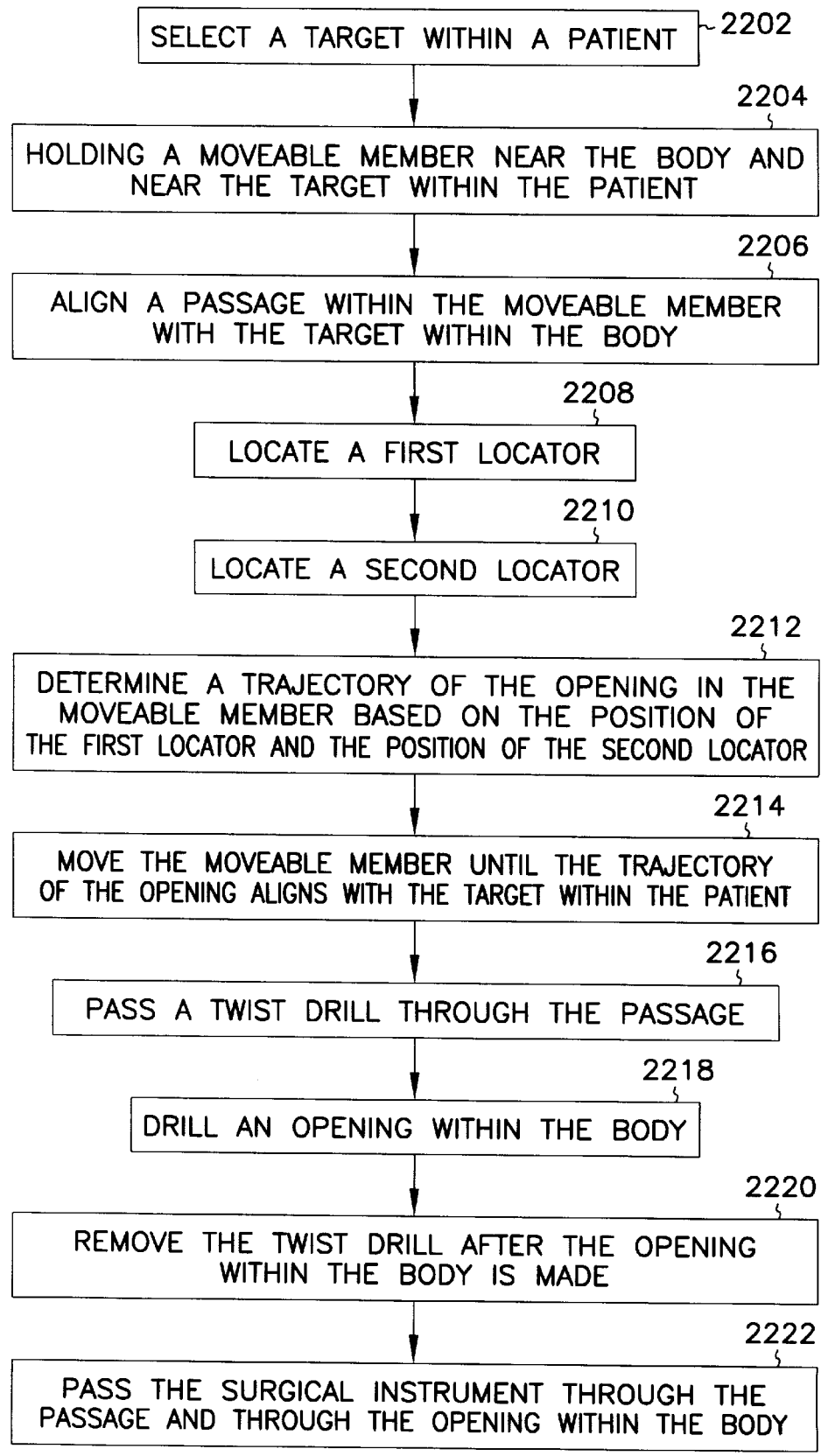
FIG. 22 is a flow chart of the process for performing a surgical procedure through a small opening within the body.

Initially as is shown in FIG. 22 a target is selected within the patient as depicted by step 2202. The movable member of the trajectory guide is positioned near the body of the patient and near the target within the patient using the snake to hold the trajectory guide 200, as depicted by step 2204. The next step, depicted by reference no. 2206, is to align the passage within the movable member with the target within the body. This can be done using nuclear magnetic resonance imaging or a CT scanner or infrared lights or any other suitable means. The methods discussed above are used in aligning the passage of the movable member with the target within the body of the patient. As shown in FIG. 22, step 2208 is to locate a first locator, and step 2210 is to locate a second locator. The trajectory of the opening in the movable member is based on the position of the first locator and the second locator, as shown by step 2212. The next step is to move the movable member 220 until the trajectory of the opening 222 aligns with the target within the patient, as depicted by step 2214. Once aligned a twist drill is passed through the opening 222, as depicted by step 2216. An opening is then drilled within the body, as depicted by step 2218. The twist drill is removed, as depicted by step 2220 and then the surgical instrument is passed through the opening 222, and through the opening within the body to the target. Another snake secures the guiding instrument, which will permit passage of a surgical drill, a biopsy needle, an observational tool, or other surgical instruments, a thermal therapy probe, or other diagnostic or therapeutic device into the body of the patient. The other snake holds a clamp which holds a hydraulic piston which can either introduce or withdraw the surgical instrument from a remote location. In this way, the device very easily can be used remotely from outside the bore of a standard MR scanner in order to introduce a surgical instrument to either a predetermined depth or to a point visualized on the MR scan obtained, while the instrument is being advanced. This simple device can be used with great precision and accuracy. It has no specific parts that are introduced into the body and can be used for repeat intervention. The device is completely external, and the only component that is, in fact, introduced into the body is the surgical instrument itself.

The device should be fully MR compatible, as well as x-ray translucent. Initially, an alignment stem is placed into the guiding component. The alignment stem is filled with fluid, but is easily visualized under routine MR, CT, or other radiographic procedures. The fluid, for MR purposes, can be normal saline or other fluid. For x-ray purposes, it might be doped with barium or other such compound.

Procedures that formerly required many hours can now be performed in substantially less amounts of time with the trajectory guide 200. For example, previously procedures to require considerable set up time including MR or CT scan, computer reconstruction of data with fiducial markers, calculation of trajectory, placement of stereotactic frame apparatus. Now with the trajectory guide 200, these procedures can be done in a matter of minutes. Furthermore the procedure is much more accurate and safer since the positioning stem can be seen by the MRI or other scanning device after the placement, whereas stereotactic systems have only retrospective data and have no such capability after placement. In a stereotactic procedure, the calculations are done and the placement procedure is performed based solely on the calculations. It is presumed to be accurate and there is really no way to determine if a surgical instrument was inserted to the target or missed the target. If the target is missed, the set up steps must be repeated. In other words, the stereotactic procedure does not have the benefit of immediate or near immediate feedback with respect to the target being missed or met. In the procedure described which uses the scan readable device, immediate or near immediate feedback can be obtained. The feedback comes with the next image calculated in an MRI scanning system, for example. The procedure described herein is also more accurate since the target 270 is also locatable by the scanning device 100 and the computer 102 associated with the scanning device is calculating the trajectory to determine if the line defined by the first locator 420 and the second locator 430 is collinear with the trajectory 260.

Many uses are contemplated for this new trajectory guide 200. For example, a surgical instrument can be used to access certain portions of the body of the patient. Using the head of a human patient as an example, the trajectory guide 200 can be used to deliver an instrument to an area of the brain for biopsy. An instrument can also be used to access the ventricular area of the brain and cerebrospinal fluid for placement of a ventricular shunt or drain. The trajectory guide can also be used to enable a neurosurgeon to perform ventricular endoscopy. The instrument in such endoscopy typically includes a fiber optic for viewing a portion of the brain. The instrument can be rigid or flexible. The trajectory guide 200 can also be used in treating or researching various other disorders or diseases of the brain, such as Alzheimer's disease, multiple sclerosis, Huntington's chorea, Parkinson's disease and other neurodegenerative diseases. The globus pallidus is one key to controlling the tremors that patients with Parkinson's disease have. In some treatments, electrodes are used to deliver electrical signals to this organ to reduce or eliminate the effect of Parkinson's disease. In addition, a surgical instrument can be used to perform a pallidotomy (i.e. lesion the globus pallidus). Similarly, other targets include the thalamus and subthalamic nucleus. Depending on the surgeon, additional targets could be considered, including nuclear and nonnuclear regions of the brain stem. Another surgical procedure is the removal of tumor material in the brain. The tumor can be located and eliminated using an instrument delivered with the help of the trajectory guide 200. Still other procedures second arm 2320 has a handle 2322 on one end and a cup 2324 on the other end. A movable member 220 with a passage or opening 222 therein is held between the cups 2314 and 2324. The movable member 220 is a ball or is substantially spherical in shape. The cups 2314 and 2324 have a radius that is close to the radius of the substantially spherically shaped movable member 220. The cups 2314 and 2324 may also be lined with an elastomeric or other material to enhance the gripping of the cups on the movable member 220. It should be noted that the size of the movable member 220 is not limited to one size and that larger and smaller spherically shaped movable members may require specialized surgical instruments 2300 having cups 2314 and 2324 with radii that are near the radius of the movable member 220. Located between the handles 2312 and 2322 is a bias or spring element 2340. The spring element 2340 is held in compression between the handle 2312 and the handle 2322. The spring element 2340 therefore biases the arm 2312 away from the arm 2322 which in turn biases cup 2314 toward cup 2324. The surgical instrument 2300 is designed so that in the absence of a force which counteracts the spring or bias element 2340, the cups 2314 and 2324 will engage the movable member 220 to fix it in one position so that surgical instruments may be passed through the opening 222 in the movable member 220. The spring element or bias element 2340 can be mounted on an arcuate portion which is attached to one of either the first arm 2312 or the second arm 2322. The spring or bias element 2340 can be placed over the arcuate member. A mating or receiving member can be attached to the opposite arm. The opposite arm also may include an opening for allowing the arcuate member to pass through the opening. A stop is typically provided on the surgical instrument 2300. The stop 2350 limits the amount of motion that can take place between the movable member 220 and the cups 2314 and 2324. By limiting the amount of motion between the cups 2314 and 2324, the spherical movable member 220 cannot be removed from the surgical instrument 2300. This would prevent an inadvertent drop of the movable member 220 during a critical portion of an operation. The stop 2350 can be incorporated within the bias are removal of lesions which are formed in the brain due to strokes or other medical conditions.

Other Uses of the Trajectory Guide

Described above are procedures associated with the brain. There are numerous other surgical procedures that can also be performed on other than the brain that would benefit from accurate placement of a surgical tool. In particular, it is anticipated that cardiac and pulmonary conditions will be ameliorated by minimally invasive therapies that can be made possible with the trajectory guide. In such procedures, the trajectory guide is more of a body portal and may or may not be used to lock into a specific trajectory toward a target. Moreover, such procedures may require use of more than one trajectory guide or may require a multiple body portal configuration in which each of the portals include one or more trajectory guides. In such therapies, surgical instruments or observational tools may be inserted to enable the surgeon in performing surgical procedures. Similarly, probes may be delivered to specific targets or general targets by the trajectory guide for the performance of cryotherapy, laser therapy, radio frequency ablation, microwave interstitial therapy, focussed ultrasound therapy and other therapies. These therapies are all currently done on various parts of the body in conjunction with an imaging device, such as an MR scanning device. A CT scanner could similarly be employed. The trajectory guide makes delivery of the instruments to the various targets easier in all of these therapies.

Figure 23:
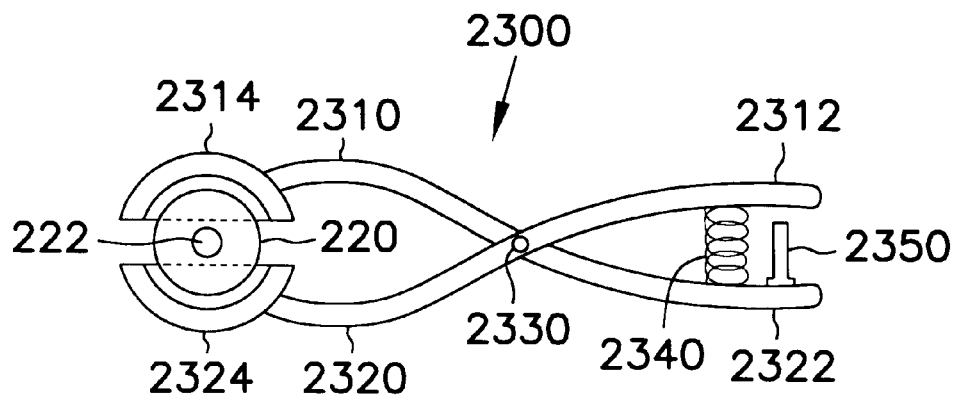
FIG. 23 is a top view of a surgical instrument for holding a movable member.

FIG. 23 is a top view of a surgical instrument for holding a movable member. The surgical instrument 2300 can be used for other surgical procedures as discussed above. The surgical instrument 2300 includes a first arm 2310 and a second arm 2320. The first arm 2310 is pivotally connected to the second arm 2320 at a pivot point 2330. The first arm 2310 has a handle 2312 on one end and a cup 2314 on the other end. The cup 2314 doesn't necessarily have to be attached to the end of the arm 2310 but may be close to the end of the arm. The element 2340, or can be incorporated at any location along arm 2322 or arm 2312, as shown in FIG. 23. In other words, stop 2350 limits the amount of potential loosening of cups 2314 and 2324 with respect to movable member 220, while spring element 2340 maintains tension such that movable member 220 is held in position.

Figure 24:
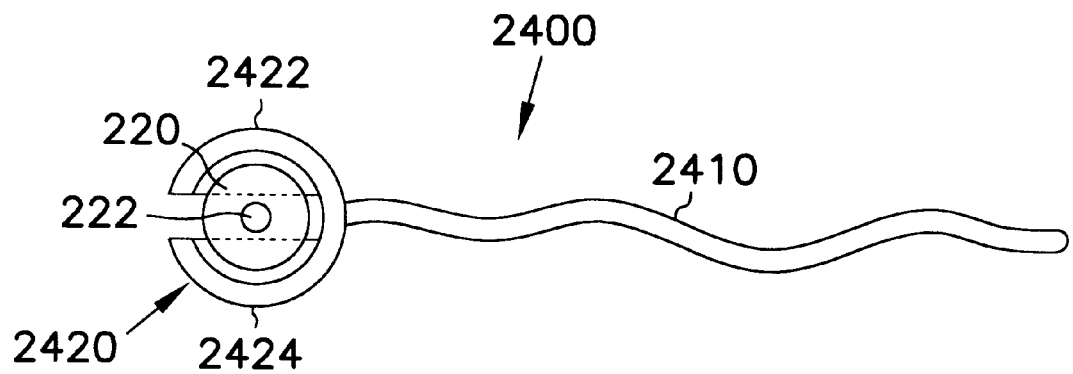
FIG. 24 is a top view of a snake clamp for holding a movable member.

FIG. 24 shows another clamp for holding a movable member 220. This clamp is commonly known as a snake clamp. The clamp 2400 includes a snake end 2410 and a jaw end 2420. The jaw end 2420 includes a set of two or more jaws which can be opened and closed slightly to allow a movable member 220 positioned between the jaws to be moved. As shown in FIG. 24, there are two jaws 2422 and 2424 associated with the jaw end 2420 of the clamp 2400. The snake end 2410 includes a plurality of articulated sections which are connected together to allow the clamp to be moved and adjusted and positioned to a selected position. The snake end 2410 includes a clamp for clamping onto an operating table or other fixed structure. In operation, the surgical instrument 2400 can be clamped to a table. The snake end 2410 can be moved so that the jaw end 2410 can be positioned to a desired location with respect to the patient. The individuals jaws 2424 and 2422 can be opened to allow for movement of the movable member 220 located between the individual jaws.

Figure 25:
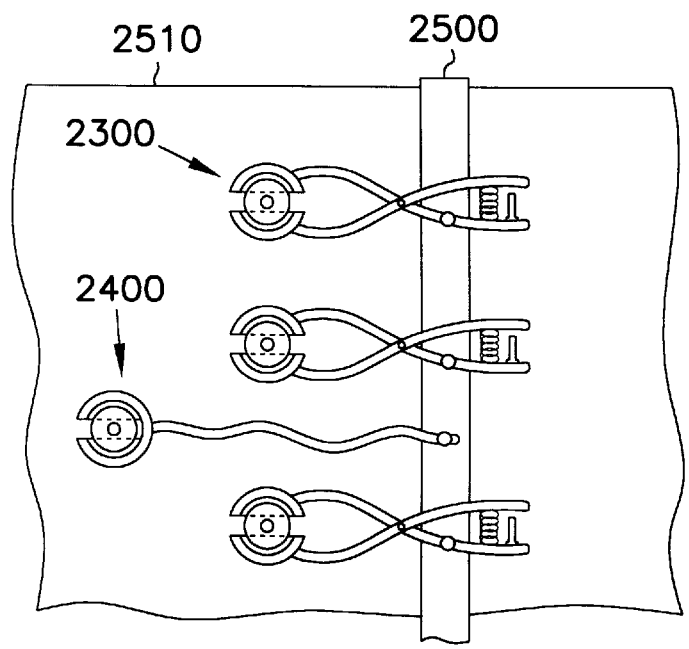
FIG. 25 is a top view of a platform or bar which holds a plurality of surgical instruments.

FIG. 25 is a top view of a platform or bar 2500 which holds a plurality of surgical instruments such as 2300 or 2400. The bar 2500 is fastened to a solid object such as a frame of a surgical table 2510. The bar 2500 can be attached at one or both ends to provide a solid platform to attach surgical instruments 2300 or 2400 thereto.

Figure 26:
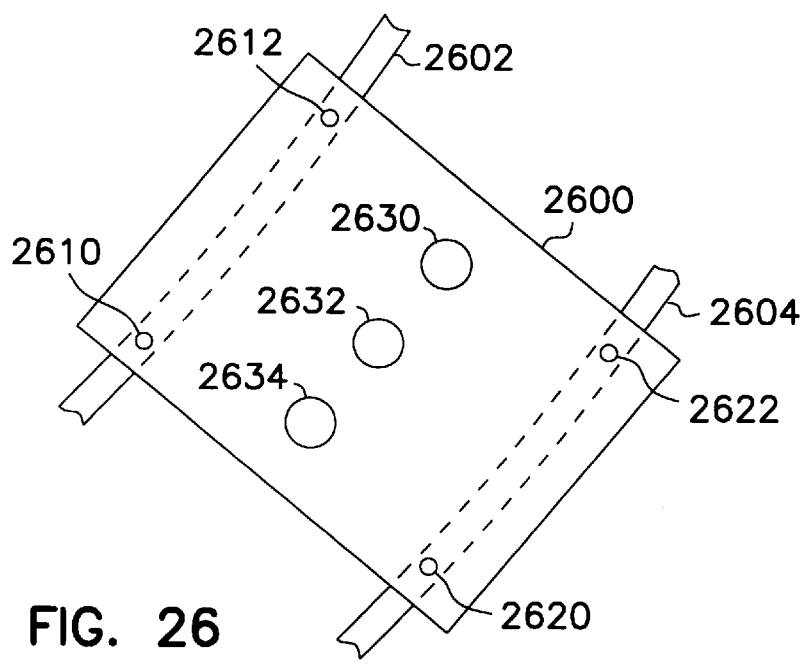
FIG. 26 is a top view of a plate which includes a plurality of movable members attached to a pair of ribs.

FIG. 26 is a top view of a plate 2600 which includes a plurality of movable member 220. The plate 2600 as shown in FIG. 26 is attached to a pair of human ribs 2602 and 2604. The plate 2600 has openings 2610 and 2612 or fasteners that pass into the rib 2602. The other end of the plate 2600 has a pair of openings 2620 and 2622 which allow fasteners to pass there through and into the second rib 2604. The openings 2610 and 2620 are spaced apart such that the spacing corresponds to the spacing between the ribs 2602 and 2604. Similarly, the spacing between the openings 2612 and 2622 are also spaced such that they correspond to the spacing between the ribs 2602 and 2604. The plate 2600 includes several cups 2630, 2632 and 2634, each of which receives a movable member 220. The cups 2630, 2632, and 2634 may have different radii to receive movable members having corresponding radii. Locking members may also be provided which are used to lock the movable members in place. The plate 2600 is contemplated for use in cardiac surgery, although it could be adapted for other uses.

Figure 27:
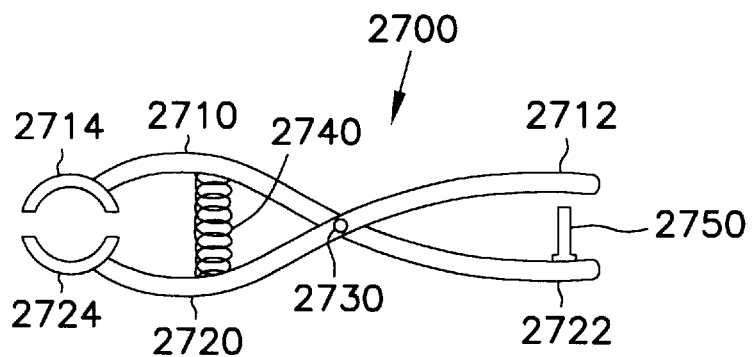
FIG. 27 is a top view of a surgical instrument designed to grip or be held within a burr hole a patient's skull.

FIG. 27 is a top view of a surgical instrument 2700 designed to grip or be held within a burr hole a patient's skull. Burr holes typically have a radius of 14 mm. Currently, many surgical procedures are performed through craniotomy flaps or craniotomy burr holes. Needles or probes are typically passed through the burr hole into the brain. The surgical instrument 2700 is typically used other surgical instruments, as shown and discussed with respect to FIG. 28. The surgical instrument 2700 includes a first arm 2710 and a second arm 2720. The first arm 2710 is pivotally connected to the second arm 2720 at a pivot point 2730. The first arm 2710 has a handle 2712 on one end and a tubular half 2714 on the other end. The cup 2714 does not necessarily have to be attached to the end of the arm 2710 but may be close to the end of the arm. The second arm 2720 has a handle 2722 on one end and a tubular half 2724 on the other end. The tubular halves 2714 and 2724 have an outside radius that is close to the radius of the burr hole. Located between the handles 2712 and 2722 is a bias or spring element 2740. The spring element 2740 is held in compression between the handle 2712 and the handle 2722. The spring element 2740 therefore biases the arm 2712 away from the arm 2722 which in turn biases tubular half 2714 and tubular half 2724 toward the edge of the burr hole. The surgical instrument 2700 is designed so that in the absence of a force which counteracts the spring or bias element 2740, the tubular halves 2714 and 2724 will engage the edge of the burr hole to fix it in one position with respect to the burr hole. The instrument 2700 also has a stop 2750 to limit the amount of motion between the handles.

Figure 28:
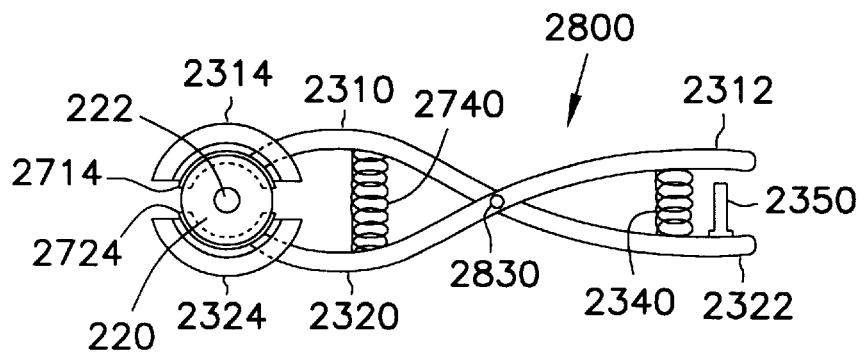
FIG. 28 shows a top view of a doublet instrument which is a combination of the instrument of FIG. 23 and a combination of the instrument shown in FIG. 27.
Figure 29:
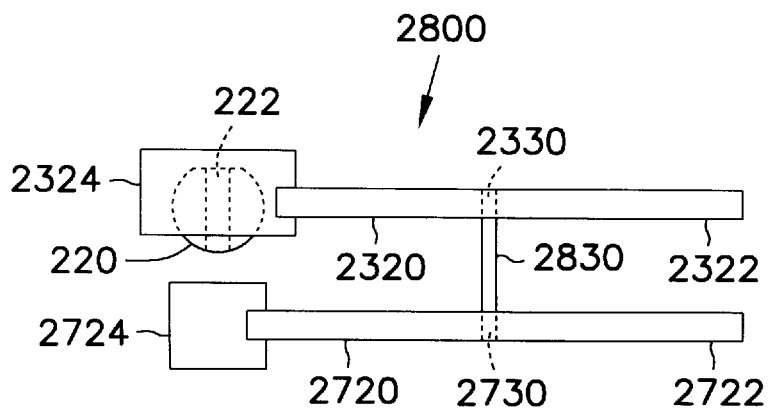
FIG. 29 shows a side view of a doublet instrument which is a combination of the instrument of FIG. 23 and a combination of the instrument shown in FIG. 27.

FIG. 28 shows a top view and FIG. 29 shows a side view of a doublet instrument 2800 which is a combination of the instrument 2300 of FIG. 23 and a combination of the instrument 2700 shown in FIG. 27. The instrument 2700 and the instrument 2300 are attached to one another via a common pivot axis 2830. The instrument 2700 holds the doublet within the burr hole in the patient's skull. The cups 2314 and 2324 of instrument 2300 hold the movable member 220 above the tubular halves 2714 and 2724 of instrument 2700 and above the burr hole in the patient's head. Once the instrument 2700 is positioned within the burr hole, the handles of the instrument 2300 can be forced open so that the movable member 220 can be adjusted to a selected angle or trajectory. Other instruments can then be passed through the opening 222 in the movable member, between the tubular halves 2714 and 2724, and through the burr hole in the patient's skull.

Figure 38:
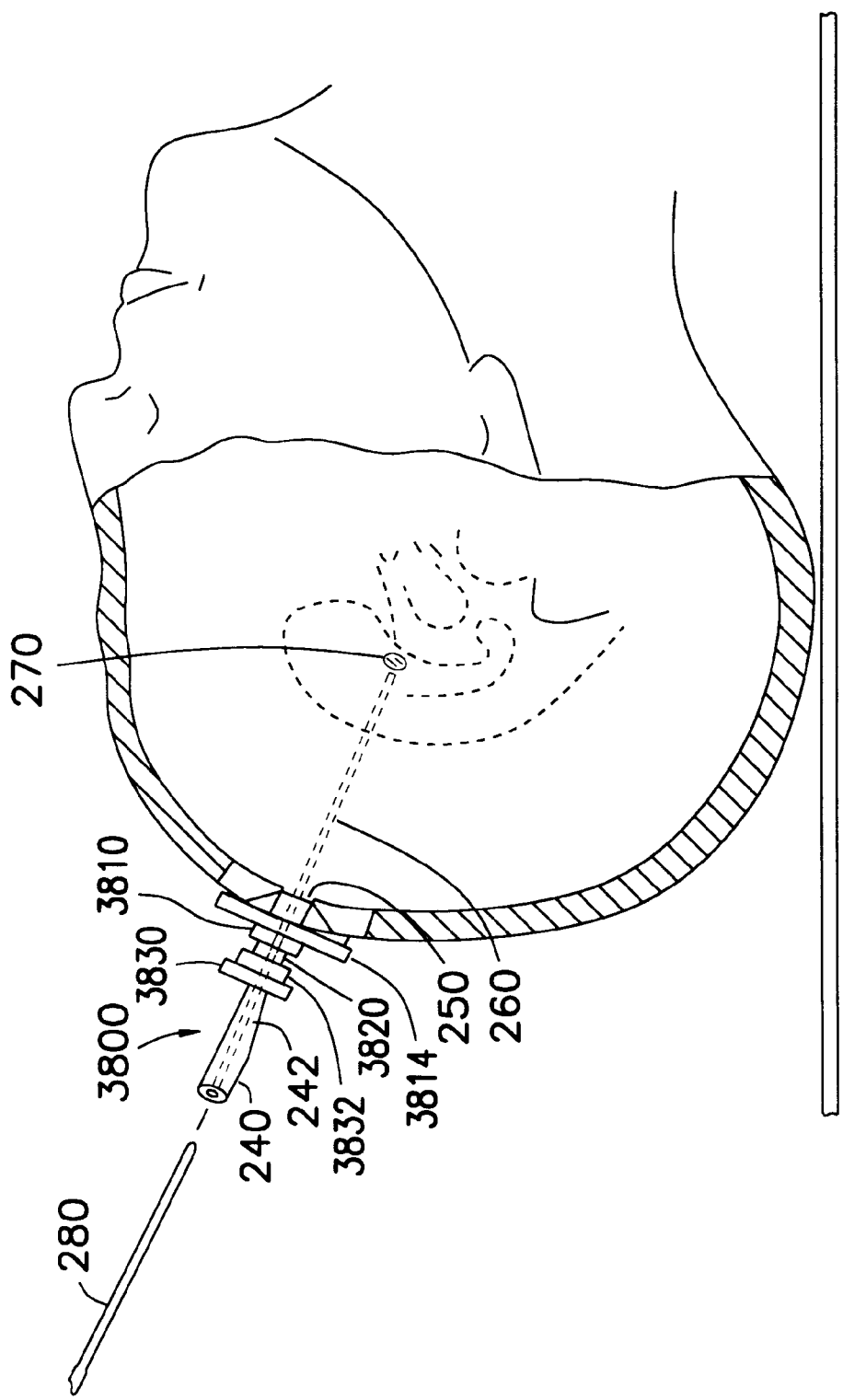
FIG. 38 is a side view of a patient on which an externalizer and trajectory guide are being used.

Within some parts of a patient, it is critical to very accurately place a surgical instrument. For example, in neurosurgery, it is very critical to have instruments, such as catheters or needles, placed very accurately within the cranium or head of a patient. FIG. 38 shows a side view of a patient on which a trajectory guide 3800 is being used. The trajectory guide 3800 includes a base unit 3810, a movable member 220, a locking member 230 and a guide stem 240. The base unit 3810 is attached to the skull of the patient. In the particular embodiment shown, the attachment is made by way of bone screws. A burr hole is not required in the patient. In this particular embodiment, the movable member 220 is held away from the patient's body such that a burr hole is not required.

The movable member 220 has a passage therein 222 which is shown in FIG. 2 as dotted lines. The guide stem 240 also has an elongated opening 242 therein. The opening 242 is also shown as dotted lines in FIG. 38. The passage 242 in the guide stem 240 and the opening 222 in the movable member or ball 220 form a line or a trajectory 260 which, when the guide stem 240 and movable member 220 are positioned correctly, intersects with a target 270 within the patient. The guide stem 240 and movable member or ball 220 form the first part of the trajectory 260. The base unit 3810 includes a seat 3818 or socket which allows the movable member 220 to move freely. The seat 3818 is positioned away from a flange 3814 on the base 3810. The seat 3818 is elevated with respect to the flange 3814. Below the seat is an opening through which instruments may pass. The elevated seat 3818 and opening below serve as a substitute for a burr hole in the skull.

After aligning the opening 242 and the opening 222 to form the trajectory 260, a twist drill is then used to make a small opening in the patient. The twist drill is passed through the opening 242 and opening 222 along trajectory 260. After a drill hole is formed in the patient, a surgical instrument or observational tool can be inserted into the opening 242 of the guide stem 240 and passed through the passage in the movable member 220 and through the drill hole formed along the trajectory 260. Further insertion of the surgical instrument or observational tool into the patient for a selected distance will strike or place the tool near or at the target 270. The opening 242 in the guide stem 240 and the passage 222 in the movable member 220 guide a surgical instrument along the trajectory 260 to the target 270. Of course, the movable member 220 is locked into place by locking member 230 before a surgical instrument 280 is placed through the opening 242 in the guide member 240.

Figure 39:
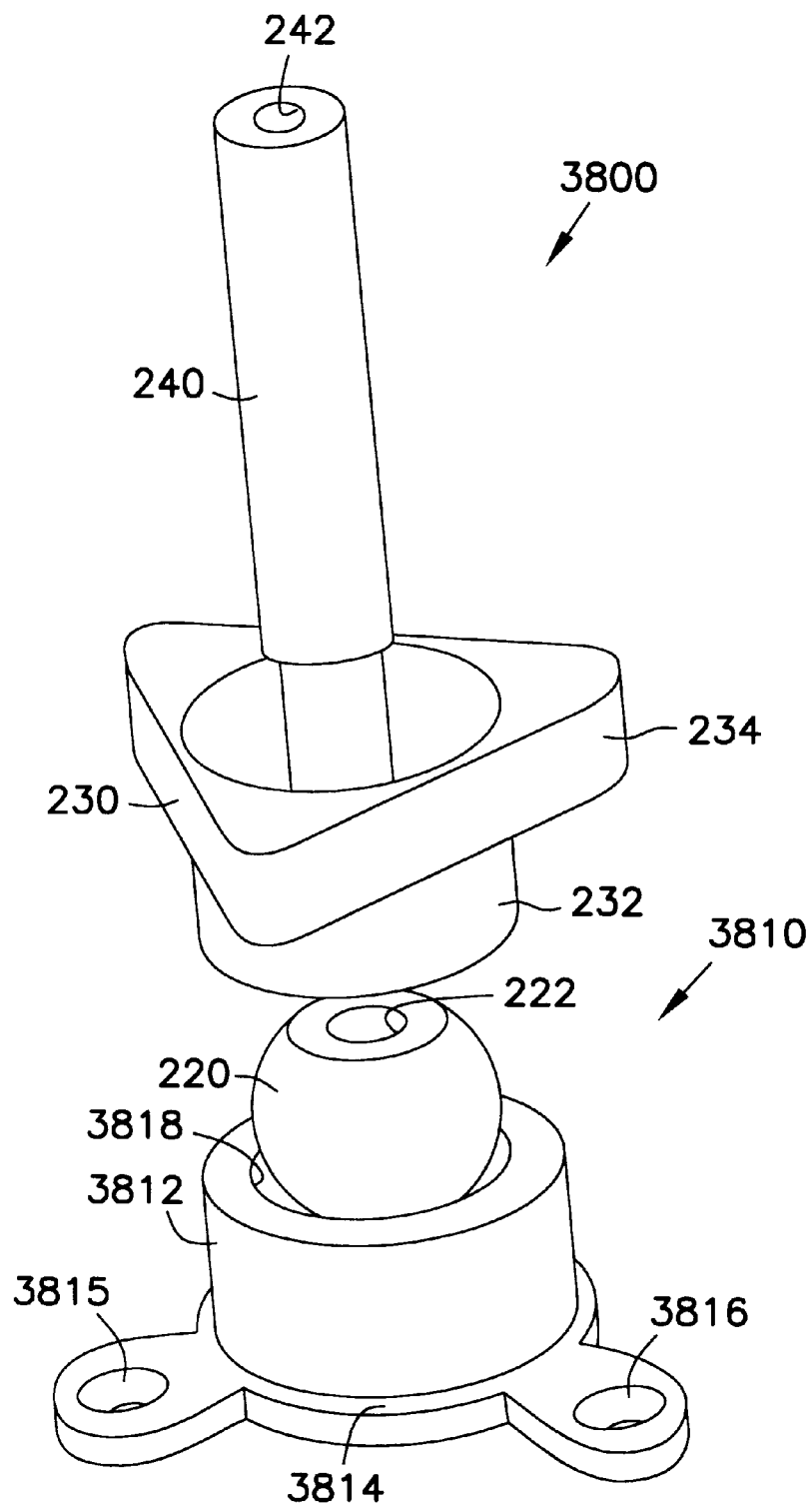
FIG. 39 is an exploded isometric view of the trajectory guide with an externalizer and a removably attached guide member installed.

FIG. 39 shows an exploded isometric view of the trajectory guide 3800 with a guide member installed. As shown in FIG. 3, the trajectory guide 3800 is comprised of a base 3810, a movable member 220, a locking member 230, and the guide member 240. The guide member 240 may be threadably attached or the guide member can be made integral with the movable member 220. The base 3810 includes a cylindrical portion 3812 and a flange 3814. The flange looks like a series of ears. Each of the ears of the flange 3814 includes a plurality of countersunk screw openings 3815, 3816, and 3817. The countersunk screw openings 3815, 3816, and 3817 receive bone screws which are screwed into the skull bone or the bone of a patient. The flange 3814 also may include markings 219 used to position the guide member 240. The base also includes a semispherical seat 3818 on the end of the base opposite the flange 3814. The flange 3814 is in a plane away from the seat 3818. Although not shown in FIG. 3, there is an opening in the base 3810 having a first end which terminates at the seat 3818 and another end which terminates at the bottom of the base 3810. This opening is essentially a substitute burr hole.

As shown in FIG. 39, the movable member 220 is essentially a spherical member or a ball. The spherical member or ball fits within the seat 3818. The spherical member or ball moves freely within the seat 3818. The ball-shaped movable member 220 also has an opening therein 222. The opening passes through the ball shaped movable member. One end of the opening may have a set of internal threads therein, which can be used to receive mating threads which are placed onto the guide stem or member 240 or positioning stem (discussed with respect to FIG. 40).

The locking member 230 also has an opening therethrough. The locking member 230 includes a cylindrical bottom portion 232 and a flange 234. The opening through the locking member 230 has sufficient space to allow movement of movable member 220 when the locking member is in an unlocked or untightened position. Although not shown in FIG. 4, the bottom of the cylindrical portion 232 of the locking member 230 includes a set of internal threads. The set of internal threads engage a set of external threads on the base unit 3810 (shown in FIG. 7b). As will be detailed later, when the internal threads of the locking member 230 are engaged with the threads on the base 3810, a portion of the locking member engages the movable member 220 to fix the movable member and the passage 222 therethrough at a fixed position.

A guide stem or guide member 240 is also shown in FIG. 39. The guide stem has an elongated opening 242 therein. The elongated opening passes through the length of the guide stem 240. One end of the guide stem includes a set of external threads which engage the internal threads of the spherical, movable member 220. When the external threads of the guide stem 240 engage the internal threads of the movable member 220, the opening 242 is substantially aligned with the passage 222 in the movable member. The opening 242 and passage 222 form the first part or guide for the trajectory 260 to the target 270 within the patient. It should be noted that the movable member 220 need not necessarily be a spherical element, although the spherical shape allows the ball to have a universal joint type swivel action which is preferred. As mentioned previously, the movable element 220 and the guide stem 240 can be formed as one piece. This would eliminate the need for the threaded end of the guide stem 240 and the threaded inner diameter 222 of the movable member 220.

In addition, the locking member 230 can be formed in most any shape. A flange 234 is useful in that it allows additional leverage for tightening or loosening the locking member. Any shape capable of being turned or placed into a locking position with respect to the movable member 220 is acceptable.

Positioning Member

Figure 40:
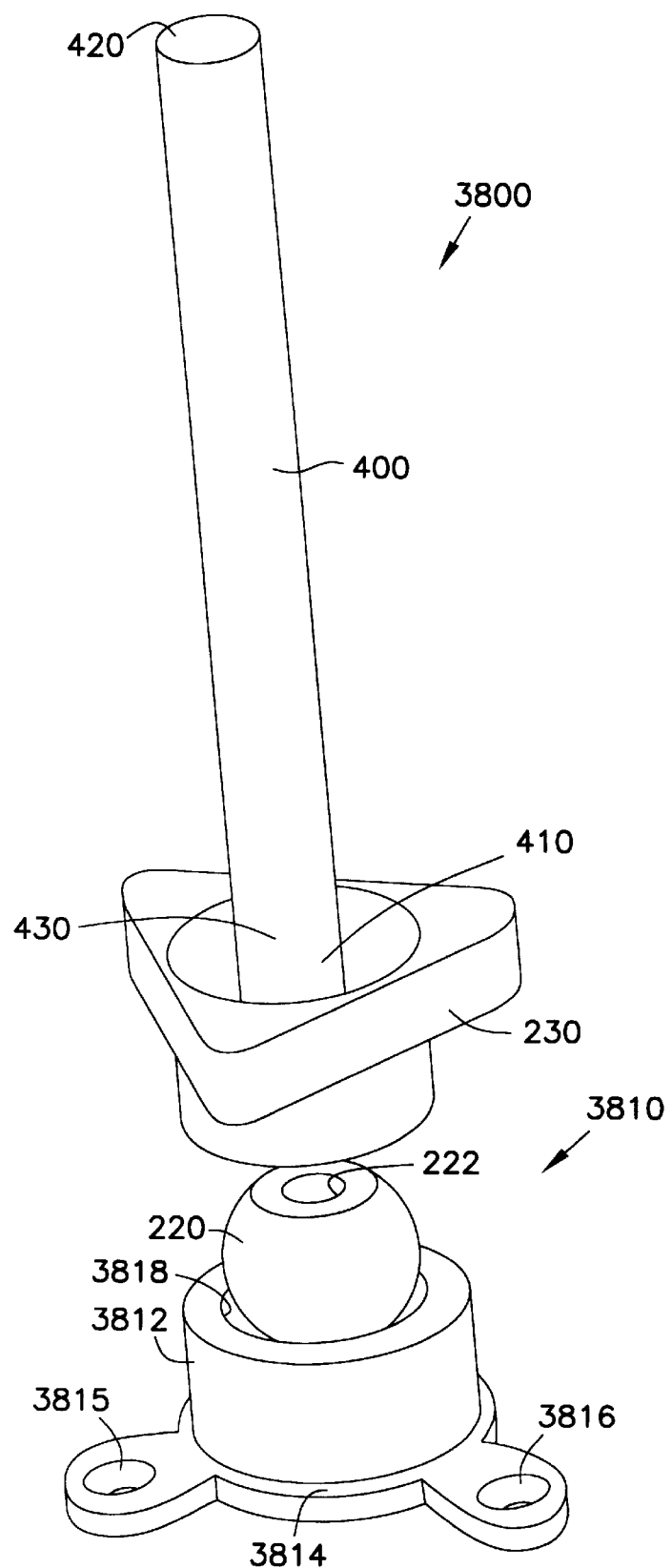
FIG. 40 is an exploded isometric view of the trajectory guide with an externalizer and a removably attached positioning member installed.

Now turning to FIG. 40, an exploded isometric view of the trajectory guide 3800 with a positioning member 400 is shown. The positioning member 400 may also be referred to as a positioning stem. Many of the parts of the trajectory guide 3800 shown in FIG. 4 are the same as those shown in FIG. 39. In the interest of time, a discussion of the common elements will not be repeated. Several of the basic elements will be numbered for the purposes of this discussion. The difference between FIGS. 39 and 40 is that the guide stem or guide member 240 has been replaced with the positioning stem 400. The positioning stem 400 includes an end 410 which carries threads for engaging internal threads within the passage 222 in the movable element 220.

Movable Member

FIGS. 5a and 5b show the movable member which is used as the movable member in the trajectory guide 3800.

Figure 41B:
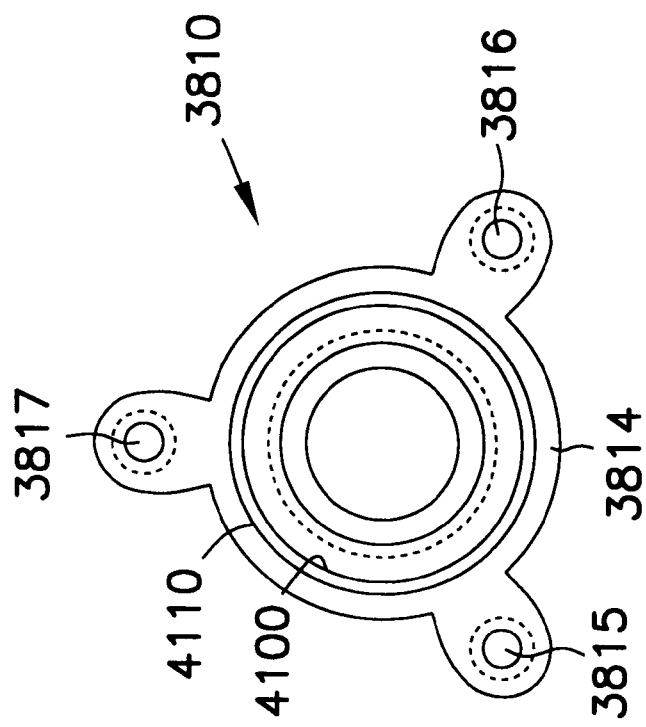
FIG. 41b is a top view of the base of the trajectory guide.
Figure 41A:
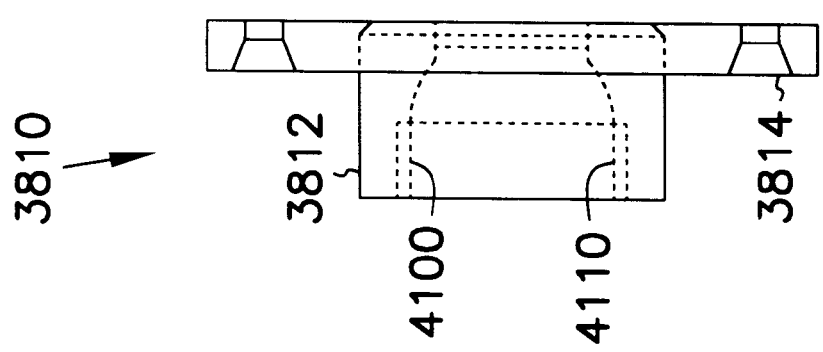
FIG. 41a is a side view of the base of the trajectory guide.
Figure 44:
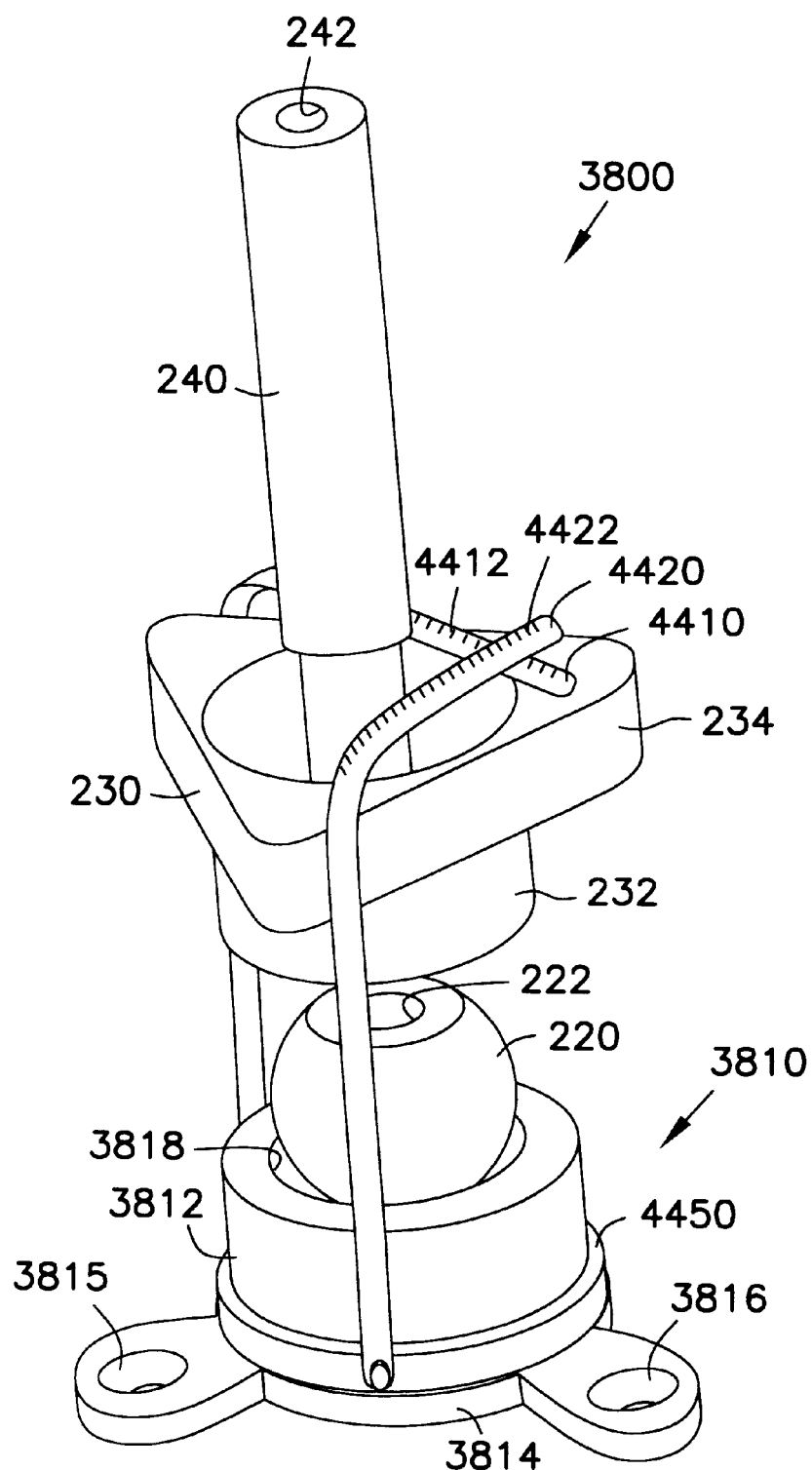
FIG. 44 is an isometric view of another preferred embodiment of the trajectory guide having arched positioning bails.
Figure 45:
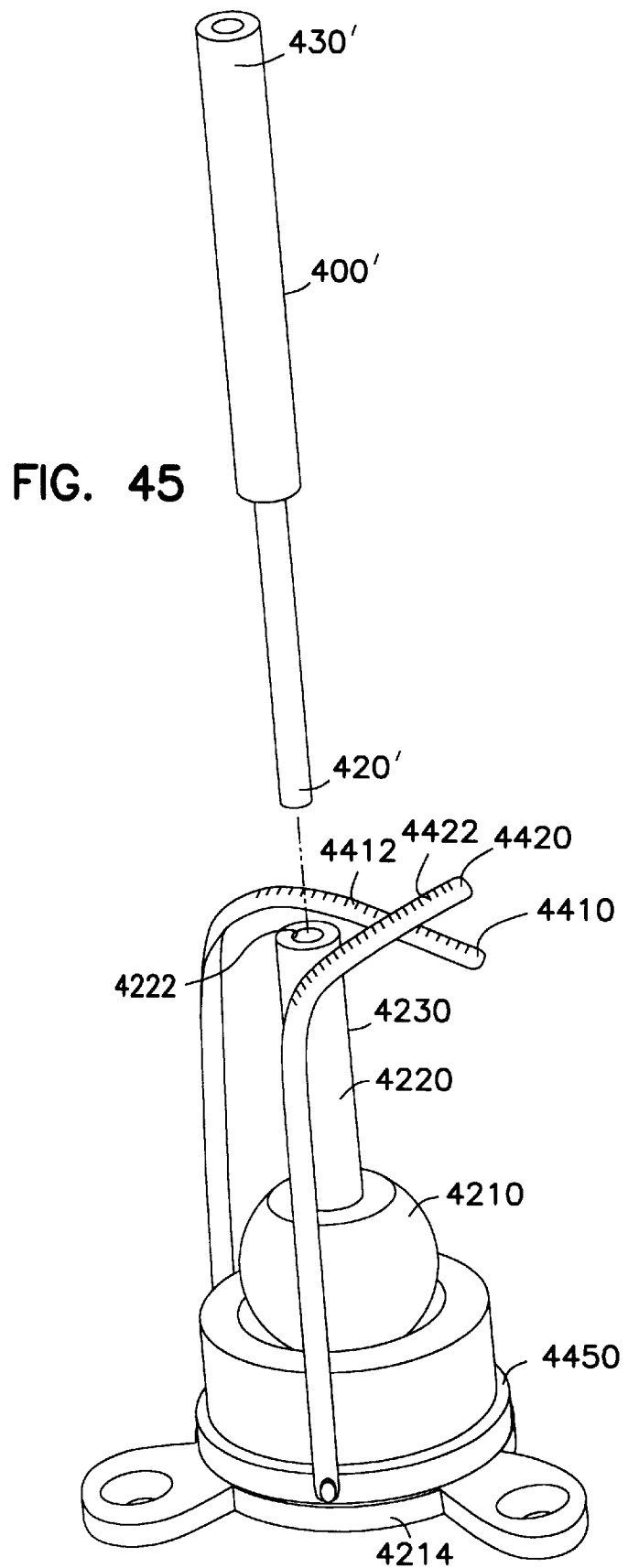
FIG. 45 is an isometric view of yet another preferred embodiment of the trajectory guide having arched positioning bails.

FIGS. 41a and 41b show a side and top view of the base 3810 of the trajectory guide 3800. The base 3810 includes the cylindrical portion 3812 and the flange 3814. The flange 3814 includes ears with countersunk openings 3815, 3816, and 3817 as well as the seat 3818 which receives the movable member 220. It should be noted that the flange 3814 can be of any shape. As shown, the seat 3818 is in a plane substantially parallel to the plane of the flange 3814. The seat 3818 is elevated with respect to the flange 3814. The seat 3818 is on one end of the base 3810 and the flange 3814 is on the opposite end of the base 3810. Between the seat and the flange is an opening 4100 which includes an internally threaded portion 610. The internally threaded portion 4110 is dimensioned so as to receive the threads of either the positioning stem 400 or the guide stem 240. The flange 3814 may include a first arched bail 4410 and a second arched bail 4420 (arched bails are shown in FIGS. 44 and 45) which are used to align the positioning stem 400 so that it defines a trajectory 260 which intersects the target 270 within the patient. It should be noted, that although the flange 214 is shown as having a triangular shape, the flange could be most any shape.

Figure 7B:
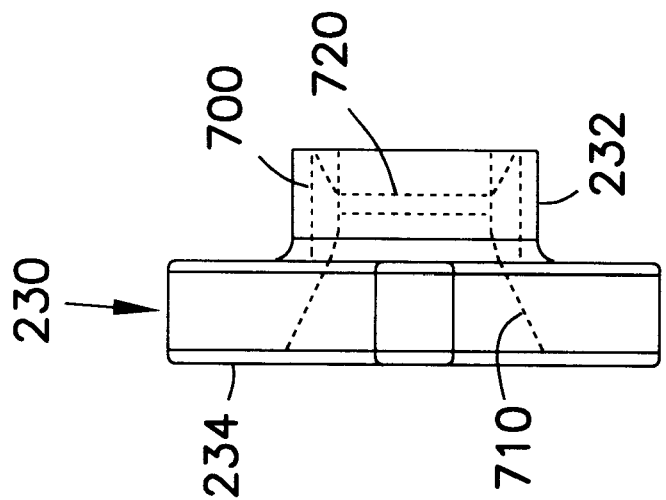
FIG. 7b is a side view of the locking member of the trajectory guide.
Figure 7A:
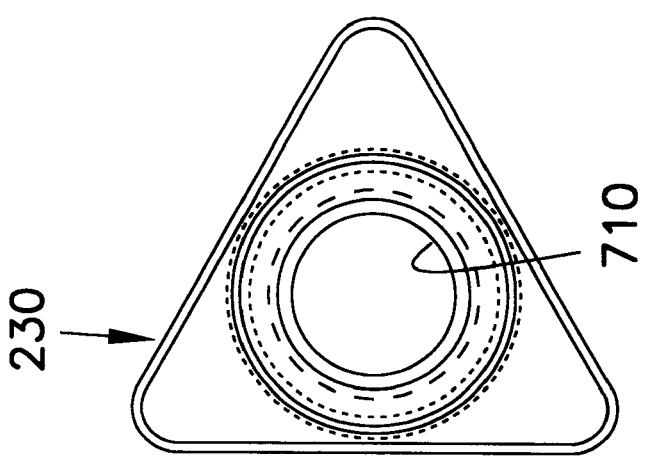
FIG. 7a is a top view of the locking member of the trajectory guide.

FIGS. 7a and 7b show the locking member 230 as used in the trajectory guide 3800.

Integral Guide Stem and Movable Member

Figure 42:
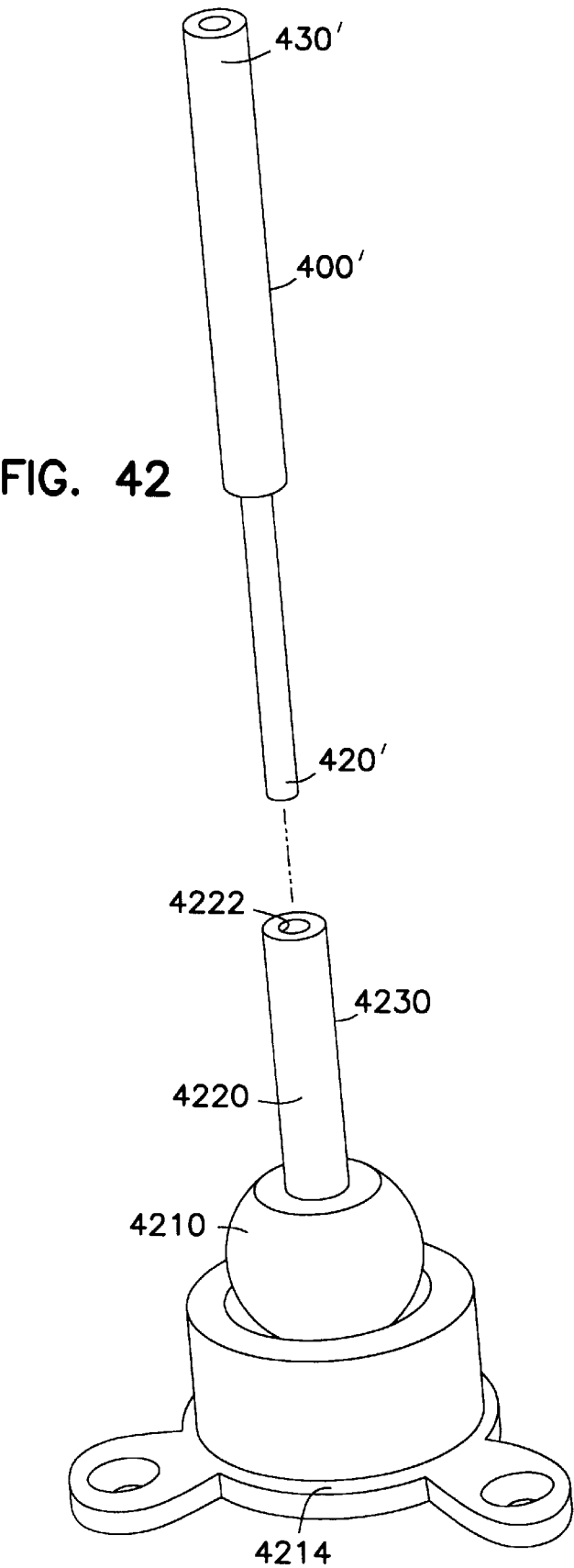
FIG. 42 is an isometric view of another preferred embodiment of the trajectory guide.

FIG. 42 shows an isometric view of a movable element 4220 that has a ball end 4210 and a guide stem end 4230. The movable element 220 fits within the base 3810 and locking member 230. As shown, the movable element 4220 has a passageway 4222 therein which traverses the length of the movable element 4220. In other words, the passageway 4222 passes through the guide stem end 4230 and through the ball end 4210. FIG. 42 also shows a positioning stem 400. The positioning stem 400 is dimensioned so that it fits snugly within the passageway 4222.

The various guide stems and positioning stems shown in FIGS. 142 can be used with any type of body scanner. The positioning stems can be provided with MR viewable portions and positioned with the aid of an MR imaging device similar to the one discussed in the U.S. patent application entitled "Surgical Instrument Trajectory Guide Method and Apparatus" filed Aug. 28, 1997 and having Ser. No. 08/919, 649. The guide stems shown in FIGS. 1–42 can also be adapted for use with a CT scanner. CT scanners are widely available around the world.

CT Scanner

Figure 43:
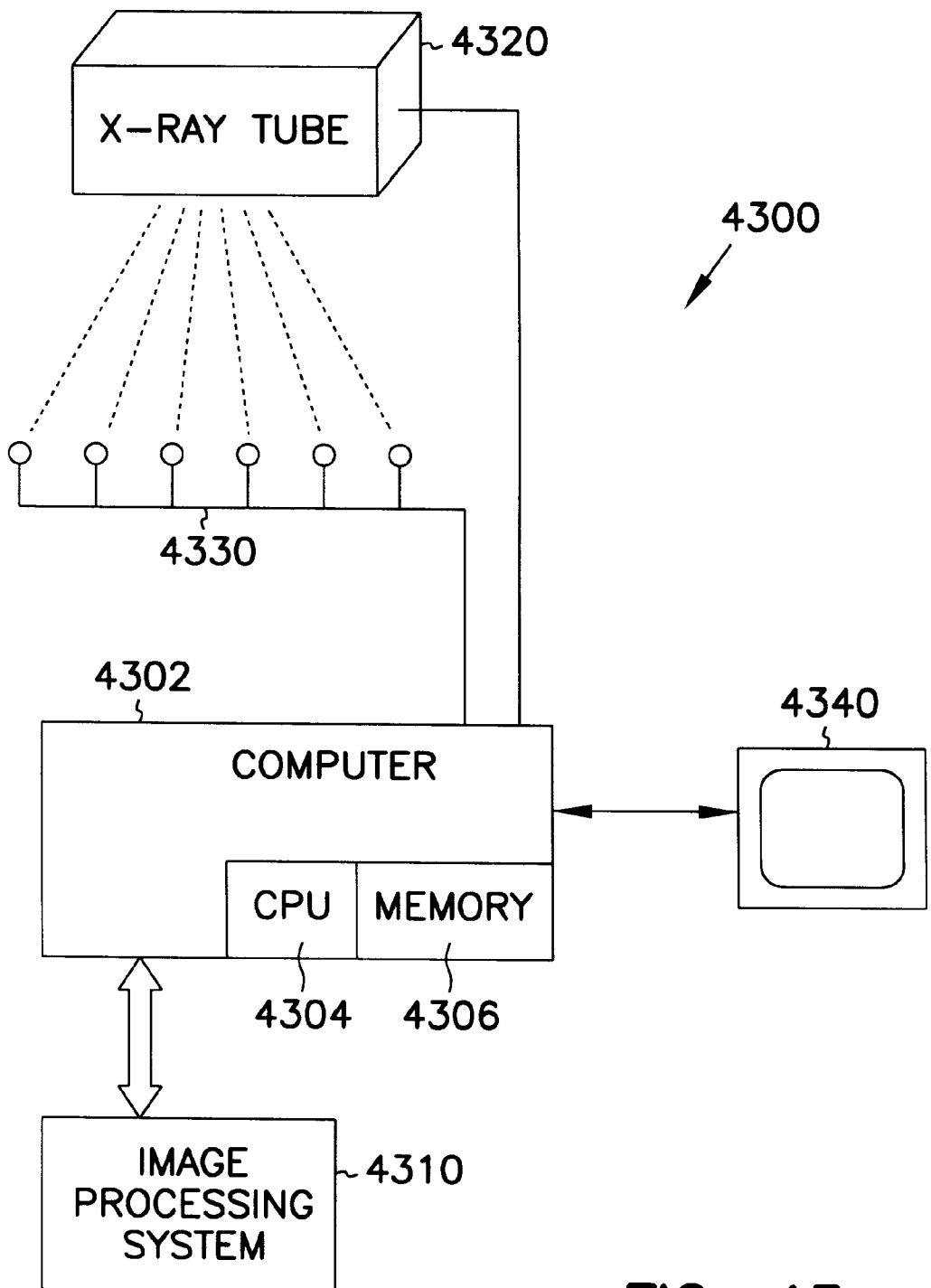
FIG. 43 is a block diagram of a computerized tomographic type patient scanning system.

FIG. 43 is a block diagram of a patient scanning system 4300. The specific scanning system shown is a computerized tomography ("CT") system. An CT scanning system 4300 includes a computer 4302. The computer 4302 includes a central processing unit ("CPU") 4304 and memory 4306. The CPU 4304 and memory 4306 have the capacity to perform multiple calculations used to determine images as well as positions of various organs, or portions or within an image field. The computer 4302 controls an image data processing portion 4310. The computer 4302 also reconstructs an image along a desired plane. An X-ray tube 4320 is pulsed at many times per second. Across from the x-ray tube are a plurality of detectors 4330. Most commonly, the detectors 4330 are photo diodes.

The data is interpreted and placed on a display 4340 associated with the computer of the CT system 4300. The computer 4302 and the CPU 4304 and memory 4306 can use data acquired from the CT system 4300 to build up images of a portion of the patient which is being subjected to x-radiation. The images are typically referred to as slices. For example, a horizontal slice and a vertical slice can be made of the portion of the body or patient being imaged. The computer can also recalculate and build other slices for use by doctors and radiologists having any selected orientation needed to facilitate study of various items within a patient. For example, lesions can be found within the body as well as certain organs. Different slices can be requested to facilitate study of these targets. From the data acquired, the position of the lesions or organs can also be very accurately determined using a Cartesian or polar coordinate system.

In operation, x-ray beams of a computerized tomography scanner pass through a human body or an object and are collected with an array of detectors; the beam is rotated to produce the equivalent of a "slice" through the area of interest. The x-ray information collected during the rotation is then used by a computer to reconstruct the "internal structures," and the resulting image is displayed on a television screen. This technique represents a noninvasive way of seeing internal structures, and has in many ways revolutionized diagnostic approaches. In the brain, for example, computerized tomography can readily locate tumors and hemorrhages, thereby providing immediate information for evaluating neurological emergencies.

Basically, the scanner gantry is composed of an x-ray tube, an array of detectors opposite the tube, and a central aperture in which the person (or object) is placed. X-rays are generated in short bursts, usually lasting 2–3 ms; the x-ray beam contains an "invisible image" of the internal structures. The role of the detectors is to collect this information, which is then fed into a computer. The computer reconstructs the image from the information collected by the detectors. In order to obtain enough information to calculate one image, the newer scanners can take as many as 90,000 readings (300 pulses and 300 detectors). CT scanning devices are widely available throughout the world. The above description of the CT scanning device 4300 is simply for demonstrative purposes.

For use with CT scanning system 4300, the positioning stem 400 of FIG. 40 is modified by doping with a dopant that is detectable with x-radiation. The dopant can be a liquid carrying barium which is housed with a tubular cavity of the position stem. The dopant can also be made within the material of the positioning stem. Since it is detectable, the positioning stem 400 is viewable as a result of the CT scan. One dopant which could be used is barium. The entire positioning stem 400 or selected portions of the positioning stem may be doped so as to produce a detectable image on the display 4380 of the CT scanning device 4300. For example, rather than dope the entire positioning stem 400, the ends 420 and 430 of the positioning stem may be doped. The two ends of the positioning stem could be detected by the CT scanning device 4300 and used to define a line corresponding to the current trajectory through the opening 222 in the movable member 220.

Now turning to FIG. 44, the further modification of the device shown in FIG. 40 will be discussed. The modifications provide for an alignment instrument which can be used where only CT scanners are available. In the alternative, if CT scanning equipment is available, it can be used as an alternative to more expensive methods, such as MR scanning. The positioning stem 400 is doped as discussed above. A ring 4450 is attached to the cylindrical portion 3812 of the base 3810. The ring 4450 moves with respect to the cylindrical portion 3812. Attached to the ring 4450 is a first arched bail 4410 and a second arched bail 4420. The arched bails 4410 have physical markings 4412 thereon. The arched bail 4420 has physical markings 4422 thereon. At least one of the bails 4410 or 4420 is also doped at least three points so that the three points determine a plane viewable on a CT scan. The arched bails 4410 and 4420 are secured to the flange 3814 with a fastener which can be securely tightened to prevent movement of the bail 4410 and 4420. The bails 4410 and 4420 are also made so that they extend a distance above the movable member 220 to allow clearance for the locking member 230.

Also for use with a CT scanning system 100, the positioning stem 400' of the trajectory guide 200', shown in FIG. 42 is doped with a dopant that is detectable with x-radiation. Since it is detectable, the positioning stem 400' is viewable as a result of the CT scan. One dopant which could be used is barium. The entire positioning stem 400' or selected portions of the positioning stem may be doped so as to produce a detectable image on the display 4380 of the CT scanning device 4300. For example, rather than dope the entire positioning stem 400', the ends 420' and 430' of the positioning stem may be doped. The two ends of the positioning stem could be detected by the CT scanning device 4300 and used to define a line corresponding to the current trajectory through the opening guide member end 4230 and the opening 4222 in the ball end 4210.

The first end 420' and the second end 430' of the positioning stem 400' do not need to be doped with the same material. This may enable the computer 4302 associated with the CT scanning device to more easily discern end 420' from end 430'. In this embodiment, the positioning stem 400' is inserted into the guide stem end 4230. The movable member 4220 and more specifically the opening 4222 in the movable member 4220 is moved until it is aligned to the desired trajectory 260 to the target 270. Once aligned, a locking member 230 (not shown in FIG. 42 to more clearly illustrate this embodiment) locks the ball end 4210 in place. The positioning stem 400' is removed and the surgical instrument is passed into the guide member end.

In still another embodiment, portions of the movable member 4220 are doped with a dopant that makes it x-radiation readable and viewable. Movable member 4220 includes a ball as well as an extended guide stem end 4230. All or part of the guide stem end 4230 may be doped. The ends of the opening 4222 in the movable member 4220 may also be doped. The ends could then be used in locating the line or trajectory 260 defined by the opening 4222. In this embodiment, there would be no real need for positioning stem 400'. When the movable member 4220 is determined to be properly aligned, the movable member 4220 would be locked into place and the surgical instrument or tool would be passed directly into the opening 4222.

FIG. 45 shows the trajectory guide 200' having a base 3810 that has a ring 4450. The arched bail 4410 and the arched bail 4420 are attached to the ring 4450. The arched bails are attached to the ring 4450 so that they can be rotatably moved with respect to the base 3810. The bails 4410 and 4420 can then be rotated with respect to the ring 4450. The attachment also allows them to be tightened so the bails 4410 and 4420 stay in one position. The bails 4410 and 4420 are positioned so that there is clearance so the locking member 230 can be loosened to adjust the position of the at least one of the bails 4410 or 4420. At least one of the bails 4410 or 4420 includes a CT readable portion that defines a plane. Preferably, one edge of the bail, 4410 or 4420, will be readable via CT scan. The edge of the bail 4410 or 4420 will be an arcuate line which defines a plane. The bail 4410 will have markings 4412 and the bail 4420 will have markings 4422. The bails 4410 and 4412 would enable a person to reposition the movable member 4220 to make adjustments to the trajectory guide so that the opening 4222 in the movable member aligns with the trajectory 260.

Method for Using CT Scans and Trajectory Guide

In operation, a patient undergoes a CT scan with a CT scanning device 4300 to locate a particular organ within a patient or to locate lesions or any other target 270 within the patient. It should be noted that targets are not necessarily limited to being within the head of a patient. There can also be other areas of a patient where it would be critical to accurately place a surgical or observational tool. In addition, it should also be noted that the patient need not necessarily be human. A patient may include any living animal.

Once the target 270 is found and located using the CT scanning system 4300, the base 3810 of the trajectory guide 3800 can be attached to the patient. The base is affixed to the patient in an area near the target 270. The computer 4302 of the scanning device 4300 is used to determine the exact location of the target 270. The exact location can be found in any type of coordinate system, although normally a Cartesian coordinate system is used. Once the base 3810 is attached to the patient, the remaining portions of the trajectory guide 3800 are attached to the base 3810. In other words, the movable member 3820, the locking guide, the locking member 3830 and a positioning stem 400 are added to form a complete trajectory guide 3800.

Figure 46:
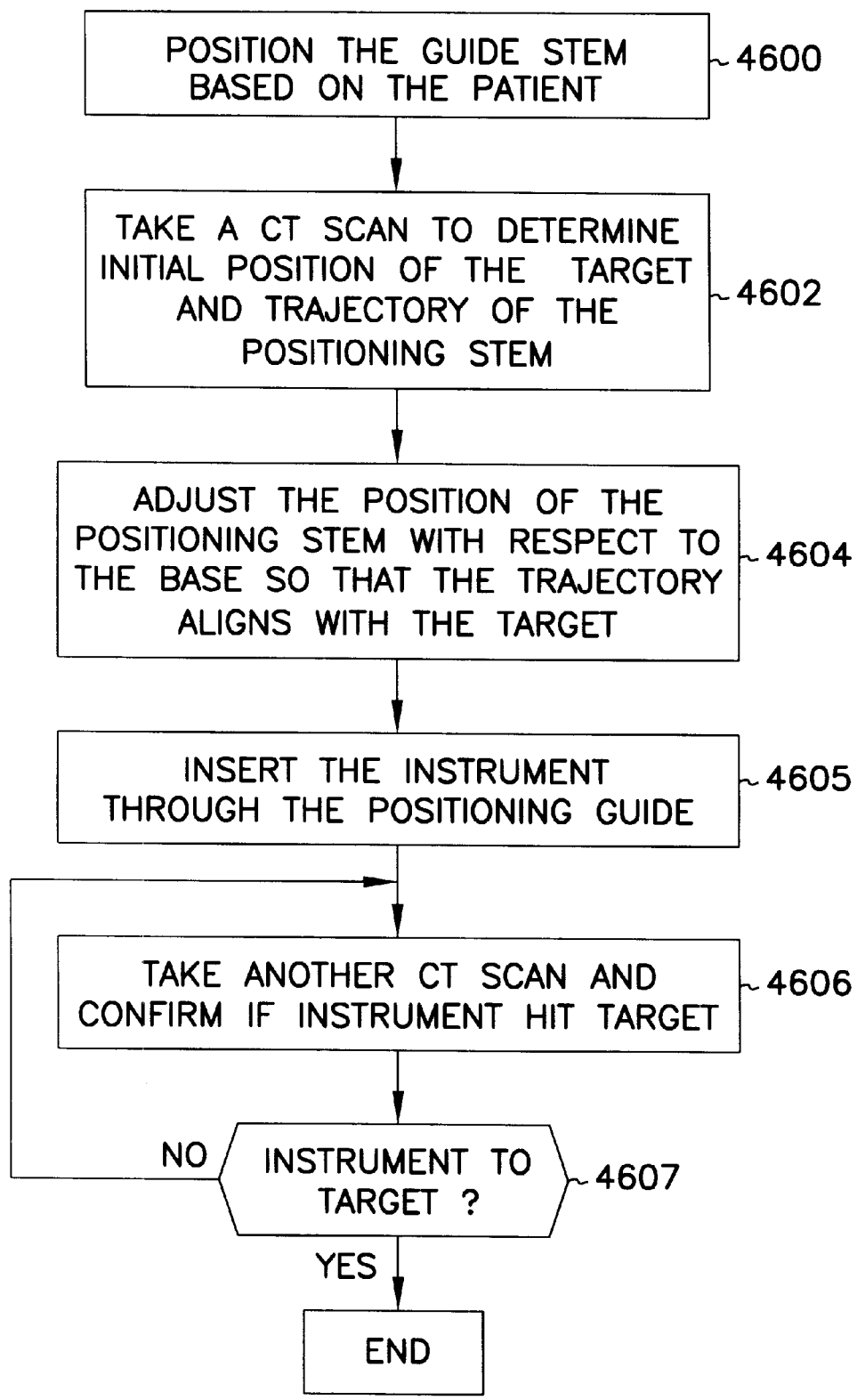
FIG. 46 is a flow chart indicating the steps in using the trajectory guide in a CT scanning environment.

Now turning to FIG. 46, as shown by step 4600, the positioning stem 400 or 400' is initially positioned. As depicted by step 4602, a CT scan is performed to initially locate the positioning stem 400 or 400' and the target 270. The line or trajectory formed by the positioning stem 400 or 400' is read by the CT scanning system 4300. The trajectory 260 is determined by determining a line between the end 430 or 430' of the positioning stem 400 or 400' nearest the patient and the target 270. The computer 4302 determines the difference between the trajectory 260 and the line formed by the doped positioning stem 400, 400'. The computer 4302 determines the adjustment that the surgeon must make to reposition the positioning stem 400 or 400' so that it corresponds to the trajectory 260. The adjustment corresponds to the increments 4412, 4422 on the arched bails 4410, 4420 attached to the base 3810.

The computer 4302 also determines the plane corresponding to the edge of one of the bails 4410 or 4420. The computer can then output an adjustment that can be made by the surgeon or person doing the procedure. Given the plane defined by the edge of one of the arched bails 4410 or 4420, the position of the other bail 4420 or 4410 can be determined.

The physician is instructed to leave one bail 4410 in a fixed position. In fact, one bail 4410 could remain in a fixed position. The edge of the other bail 4410 is moved to a mark 4412 on the fixed bail 4410. The edge with the markings 4422 is moved to a mark 4412. The bail 4420 is then secured into position. The surgeon then moves the positioning stem 400 or 400' to a mark 4422 on the second bail 4420 to reposition the positioning stem 400 or 400' so that it corresponds to the trajectory 260. This series of steps corresponds to the step of adjusting the position of the positioning stem so the trajectory aligns with the target 4604.

The instrument is then inserted using the guide stem. In the instance of the trajectory guide 3800, the positioning stem is replaced by the guide stem. In the instance of the trajectory guide 3800', the positioning stem 400' is removed and then the instrument is placed in the movable member. The instrument is inserted to a selected distance into the patient, as depicted by step 4607. The selected distance is the distance to the target 270 along the trajectory 260.

Another CT scan is then done, as depicted by step 4606, to confirm that the instrument is at the target 270. If the instrument has not reached the target 270, the needle is inserted another selected distance (step 4605).

The procedure for repositioning the positioning stem 400 or 400' may be modified slightly depending on the size of the target 270 and whether a burr hole opening will be made. The trajectory guides 3800 and 3800' do not need a burr hole, but they can be used with burr holes. If a burr hole is formed, the contents within the cranium shift may shift slightly as a result of fluid loss through the burr hole. If the target 270 is large, such as a tumor, it may not be necessary to recheck the trajectory 260. If the target is small, it may require a recheck of the trajectory even if only a twist drill opening is made in the skull.

Frameless Stereotaxy Environment

Figure 47:
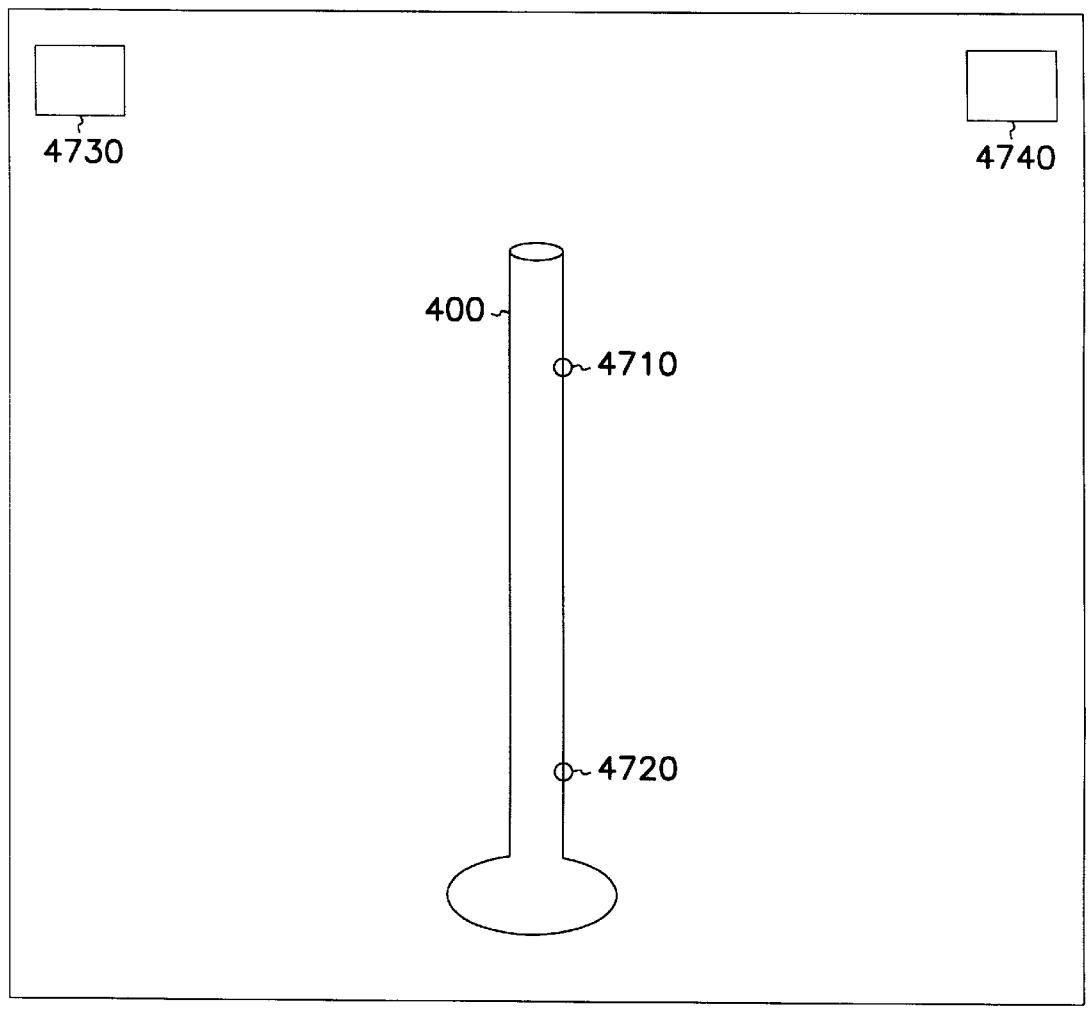
FIG. 47 is a side view of the positioning stem of the trajectory guide which includes light-emitting diodes.

In an environment where there are detectors for light-emitting diodes ("LEDs"), the trajectory guide 3800 as shown in FIG. 40 or the trajectory guide 200' as shown in FIG. 42 can be used to accomplish this procedure. FIG. 47 shows the positioning guide 400 of the trajectory guide 3800 provided with two or more LEDs 4710 and 4720 which are located along the length of the positioning stem 400. Rather than use the arched bails 4410 and 4420 to reposition the positioning stem 400, one or more LED detectors 4730 and 4740 are used to locate the LEDs 4710 and 4720. The step of adjusting the position of the positioning stem 4604 so that it aligns with the trajectory 260 to the target 270 is accomplished by moving the positioning stem 400 manually until the LEDs 4710 and 4720 form a line which is collinear with the trajectory 260. The computer 4302 determines the trajectory 260 by determining the formula for a line between the target 270 and the end of the positioning stem 400 closest to the patient. The positioning stem 400 is moved until the LEDs 4710 and 4720 are aligned with the trajectory 260. The positioning stem can be moved manually (directly or remotely) or by automated control, such as under control of a computer. The LED's position can be determined by the detectors 4730 and 4740 at a relatively high frequency rate such that movement of the positioning stem 400 can be monitored in real time. Once the LEDs 4710 and 4720 are aligned with the trajectory 260, the computer 4302 will output a signal indicating that the positioning stem 400 is correctly positioned. The same procedure would be followed for a trajectory guide 200'. The positioning stem 400' would be provided with the LEDs 4710 and 4720. Once the positioning stem 400' is correctly positioned, a signal from computer 4302 indicates the correctly positioned positioning stem 400'. The movable member 4220 is then locked into position. The positioning stem 400' is removed and the instrument is passed into the opening 4222 in the movable member 4220.

Of course, this procedure may be modified slightly depending upon the particulars of the procedure. The trajectory guides 200 and 200' do not need a burr hole, but can be used with burr holes. If a burr hole is formed during the procedure, the contents of the cranium shift slightly as a result of fluid loss through the burr hole. If the target 270 is large, such as a tumor, it may be unnecessary to recheck the trajectory 260. If the target is small, such as when the target is the globus pallidus interna, it may be necessary to recheck the trajectory before inserting a tool or an instrument to the target 270. Once the trajectory 260 is determined, the instrument or tool is inserted a selected distance into the trajectory guide 200 or 200'. The selected distance is equal to the distance between the trajectory guide and the target 270. The position of the instrument or tool can then be checked using x-radiation to determine if the tool or instrument has reached the target 270.

Magnetic Resonance Imaging Procedure

The trajectory guide 3800 or 3800' can also be used in an MR imaging environment. In such an environment, the positioning stem 400 or 400' is provided with a dopant that can be read by an MR imaging device. The procedure set forth above for the frameless stereotaxy environment is similar to the procedure used here. The MR imaging device is used to determine the position of the positioning stem 400 and to determine the trajectory between the portion of the positioning stem nearest the patient and the actual target 270. The positioning stem 400 is moved either manually or with the aid of a remote device. The positioning stem 400 is moved until it is positioned so that it is collinear with the trajectory 260 between target 270 and the end of the positioning stem 400 nearest the patient.

Figure 48:
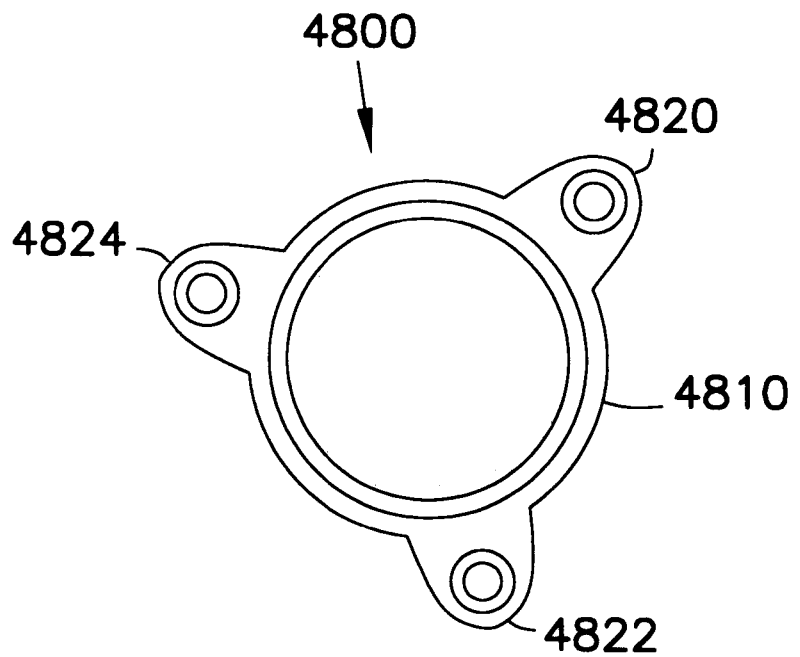
FIG. 48 is a top view of a burr hole extension apparatus.

The basic procedure set forth in FIG. 48 varies at a step 4604, which is to adjust the position of the positioning stem. When using CT scanning equipment only, the positioning stem 400 is adjusted using the arched bails 4410 and 4420. When the trajectory guide is used in an MR environment, the MR scanning device is used to locate the position of the positioning stem 400. In either environment, the positioning stem 400 may be used in association with frameless stereotaxy, in which case LED detectors are used to find the position of the positioning stem. Once the positioning stem is properly located collinearly with the trajectory 260, the instrument is inserted through the trajectory guide 200 or 200' toward the target 270 to a specific distance. Another scan is then taken to confirm that the instrument is at the target. These are the steps as shown and described previously and correspond to steps 4606 and 4608 in FIG. 46.

FIGS. 10–14, 19–22 and 30–37 show and describe remote controlled versions of trajectory guides 200' that could be used under MR guidance.

Burr Hole Externalizer Adapter for Other Tools

Figure 49:
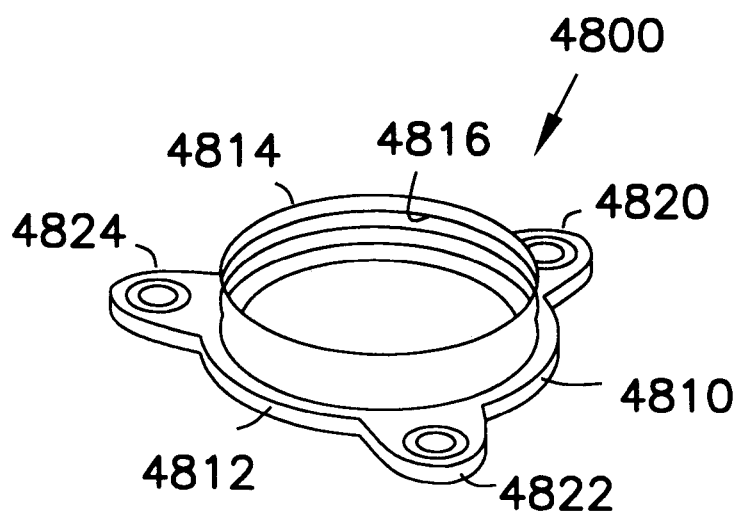
FIG. 49 is a side view of the burr hole extension apparatus shown in FIG. 10.
Figure 50:
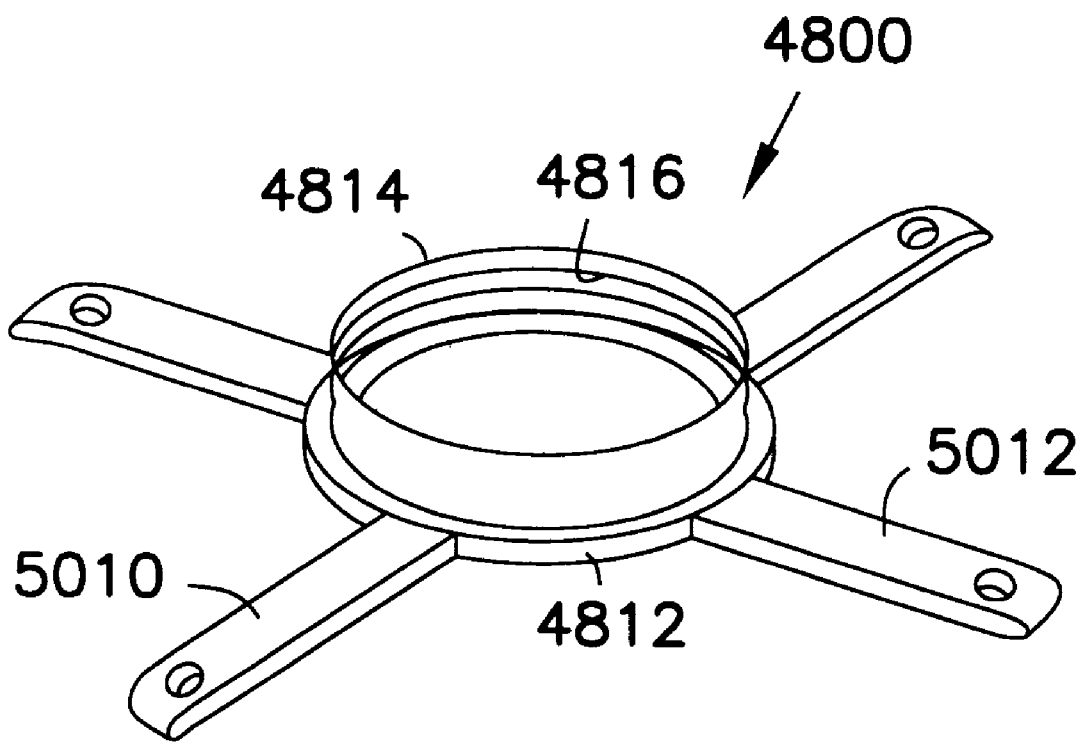
FIG. 50 is a top view of another embodiment of the burr hole extension apparatus.

Turning now to FIGS. 48–50, the burr hole externalizer will be detailed. FIG. 48 is a top view of a burr hole extension apparatus 4800. FIG. 49 is a side view of the burr hole externalizer 4800. The burr hole externalizer 4800 is made of a tubular body 4810 with a set of flanges 4820, 4822, and 4824 attached thereto. The tubular body 4810 is approximately 1 cm in height. The tubular body 4810 has a height that allows clearance between the tubular body and the tool to allow insertion of the tool into the patient's body. The tubular body 4810 has a flange end 4812 and a burr hole end 4814. The flanges 4820, 4822, and 4824 are used to attach the burr hole externalizer 4800 to the patient. The flanged end 4812 is the end of the burr hole externalizer 4800 that contacts the patient. The burr hole end 4814 is positioned a distance from the patient's body. The burr hole externalizer 4800 basically provides a substitute opening for a burr hole that used to have to be made in the patient. The burr hole end 4814 of the tubular body is dimensioned so that it replicates a burr hole. The inner diameter of the burr hole end 4814 is the same as a standard burr hole. It should be pointed out that the Europeans have one standard diameter and the rest of the world has another standard diameter. The burr hole end 4814 may also include an inside thread 4816 so that tools which thread into a burr hole can also thread into the burr hole end 4814 of the externalizer 4800. It should be noted that an inside thread is not necessary. Thus the externalizer 4800 can also be thought of as a universal adapter for tools that normally are attached to a burr hole.

In operation, a physician/surgeon will initially position the burr hole externalizer 4500 onto the patient's body. For the sake of example, the physician surgeon will initially position the externalizer on the patient's head. The burr hole externalizer is held in place using several bone screws. The bone screws pass through openings in each of the flanges 4820, 4822, and 4824. A selected tool is then attached to the burr hole end 4514 of the burr hole externalizer 4800. The tool attached can be a trajectory guide such as described above or such as described in U.S. patent application Ser. No. 08/919649 filed Aug. 28, 1997 and entitled "Surgical Instrument Trajectory Guide Method and Apparatus". The tool can be any tool that previously required attachment to a burr hole in the body of the patient. The advantages associated with using the burr hole externalizer 4800 stem from the fact that the surgeon no longer has to make a burr hole in the patient. Not having to make a burr hole means that the procedure takes less time. It also results in less fluid loss from the spine and the cranium which results in less shifting of the target or contents of the head. In addition to several small bone screws, the only opening made in the patient's body is a small twist drill hole. A twist drill hole has a diameter of approximately 2 mm. This is much smaller than the 12–15 mm burr hole previously discussed above. A drill hole of this small size can be made with a minor incision or scalp or upper body area and with minimal trauma. Thus, there is less trauma and less discomfort for the patient when the burr hole externalizer is used.

FIG. 50 is a top view of another embodiment of the burr hole externalizer 4800. Most of the components are the same and are numbered the same as the externalizer 4800 shown in FIG. 48. The difference is that the flanges are replaced with a first headband 5010 and a second headband 5012. This produces four long legs when compared to the externalizer 4800 shown in FIG. 48. Three elongated legs could also be used to provide adequate attachment of the externalizer to the patient's body. In the ends of each head band are openings for body screws. The body screws may not have to be used to secure the burr hole externalizer 4800 to the patient. It should be noted that the embodiments shown are just two examples of ways of attaching the burr hole externalizer 4800 to the patient. There are many ways of stably attaching the burr hole externalizer 4800. In addition, although a burr hole is normally used for entering the cranial cavity, this externalizer 4800 could easily be used for similar operations on other portions of the patient's body. Procedures that formerly required many hours can now be performed in substantially less amounts of time with the burr hole externalizer and the trajectory guide 3800.

Many uses are contemplated for this new trajectory guide 3800. For example, a surgical instrument can be used to access certain portions of the body of the patient. Using the head of a human patient as an example, the trajectory guide 3800 can be used to deliver an instrument to an area of the brain for biopsy. An instrument can also be used to access the ventricular area of the brain and cerebrospinal fluid for placement of a ventricular shunt or drain. The trajectory guide can also be used to enable a neurosurgeon to perform ventricular endoscopy. The instrument in such endoscopy typically includes a fiber optic for viewing a portion of the brain. The instrument can be rigid or flexible. The trajectory guide 3800 can also be used in treating or researching various other disorders or diseases of the brain, such as Alzheimer's disease, multiple sclerosis, Huntington's chorea, Parkinson's disease and other neurodegenerative diseases. The globus pallidus is one key to controlling the tremors that patients with Parkinson's disease have. In some treatments, electrodes are used to deliver electrical signals to this organ to reduce or eliminate the effect of Parkinson's disease. In addition, a surgical instrument can be used to perform a pallidotomy (i.e., lesion the globus pallidus). Similarly, other targets include the thalamus and subthalamic nucleus. Depending on the surgeon, additional targets could be considered, including nuclear and nonnuclear regions of the brain stem. Another surgical procedure is the removal of tumor material in the brain. The tumor can be located and eliminated using an instrument delivered with the help of the trajectory guide 3800. Still other procedures are removal of lesions which are formed in the brain due to strokes or other medical conditions.

Other Uses of the Trajectory Guide

Described above are procedures associated with the head and brain. There are numerous other surgical procedures that can also be performed on other than the brain that would benefit from accurate placement of a surgical tool. In particular, it is anticipated that cardiac and pulmonary conditions will be ameliorated by minimally invasive therapies that can be made possible with the trajectory guide. In such-procedures, the trajectory guide is more of a body portal and may or may not be used to lock into a specific trajectory toward a target. Moreover, such procedures may require use of more than one trajectory guide or may require a multiple body portal configuration in which each of the portals include one or more trajectory guides. In such therapies, surgical instruments or observational tools may be inserted to enable the surgeon in performing surgical procedures. Similarly, probes may be delivered to specific targets or general targets by the trajectory guide for the performance of cryotherapy, laser therapy, radio frequency ablation, microwave interstitial therapy, focussed ultrasound therapy and other therapies. These therapies are all currently done on various parts of the body in conjunction with an imaging device, such as the CT scanning device 4300. The trajectory guide 3800 makes delivery of the instruments to the various targets easier in all of these therapies. In addition, the use of the burr hole externalizer 4500 further speeds procedures that require the entry of tools into the patient's body.

Figure 51:
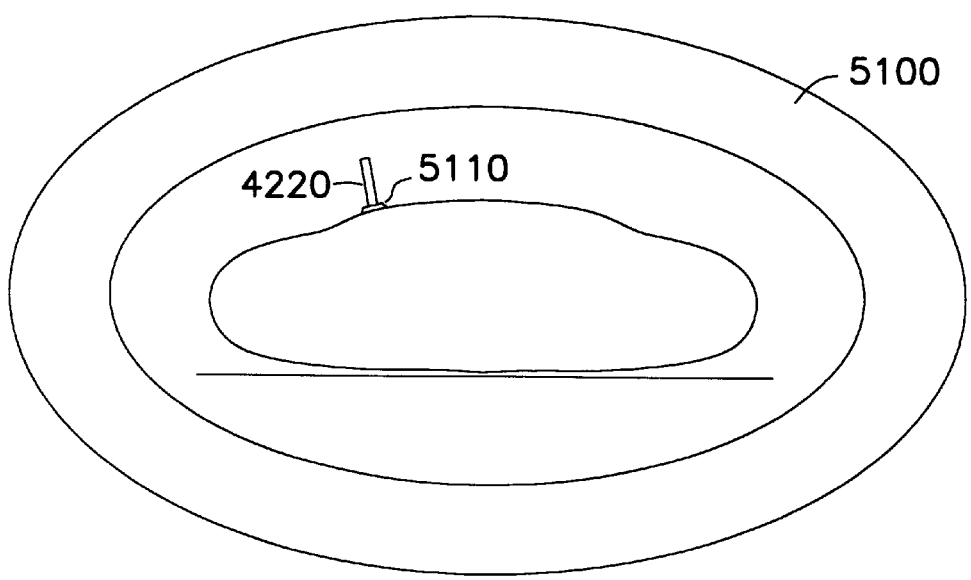
FIG. 51 is an end view of a patient positioned within a magnet having a body type trajectory guide attached thereto.
Figure 52:
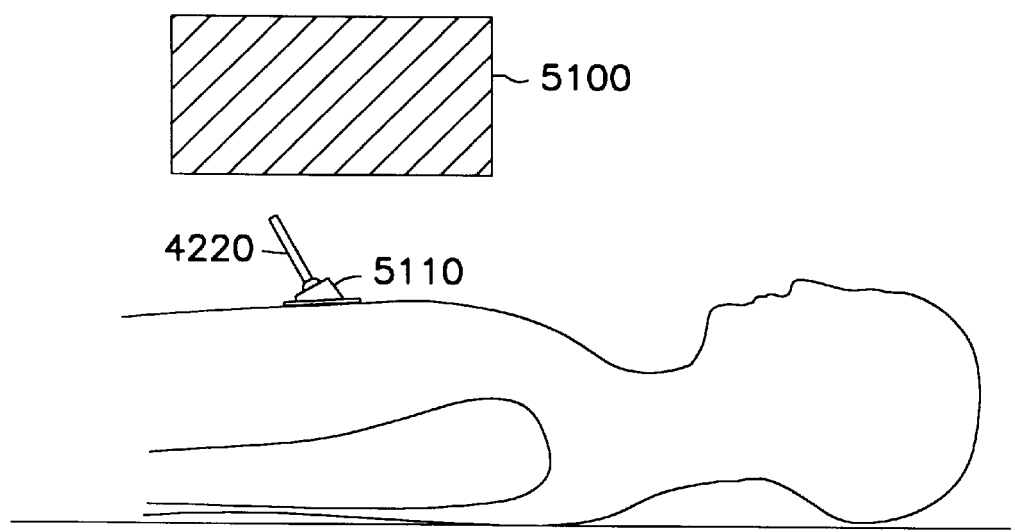
FIG. 52 is a side view of a patient positioned within a magnet having a body type trajectory guide attached thereto.

FIGS. 51–55 show a trajectory guide 5100 which can be used as a body portal. FIG. 51 is an end view of a patient positioned within a MR scanner 5100. The patient has a body portal type trajectory guide 5110 attached and positioned on their body. FIG. 52 is a side view of a patient positioned within a conventional MR scanner 5100. As shown in FIG. 52, the body portal type trajectory guide is positioned at an angle with respect to the body of the patient so that the total overall height of the body portal type trajectory guide 5110 will fit within the conventional MR scanner 5100. The movable element 4220, if positioned perpendicular with respect to the body, may interfere with the MR scanner 5100. Most certainly if the movable element 4220 is positioned perpendicular with respect to the body, a surgical instrument could not be placed within the movable element 4220. A surgical instrument such as a catheter extends through a longitudinal opening or passageway 4222 in the movable element 4220. When perpendicular to the patient, there would not be enough room between the MR scanner 5100 and the surgical instrument being placed within the passageway 4222 of the movable element 4220. It should be noted that the body portal type trajectory guide 5110 may be equipped with a movable element 4220 or a guide member 240 or a positioning member 400. The movable member 4220 is rotatable with respect to the patient so that a surgical instrument may be placed within the movable member 4220 from any position the surgeon may take with respect to the patient. In a scanning environment that has an open magnet, an angled base is not necessary. The base for the body portal type positioner could be made with a vertical surface or a surface substantially parallel to the patient's body.

Figure 53:
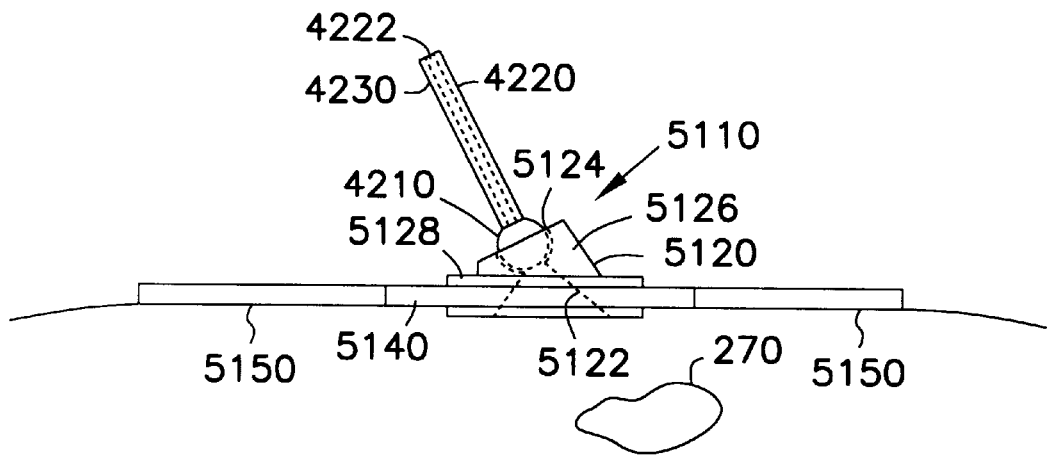
FIG. 53 is a side view of a body type trajectory guide.
Figure 54:
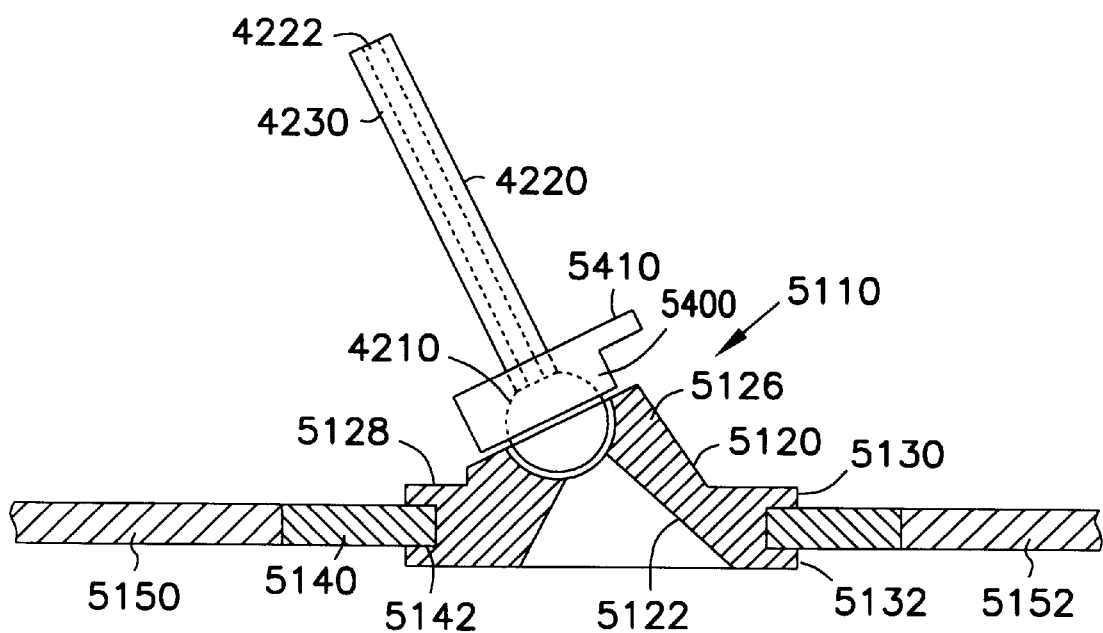
FIG. 54 is a cutaway side view of the body type trajectory guide.
Figure 55:
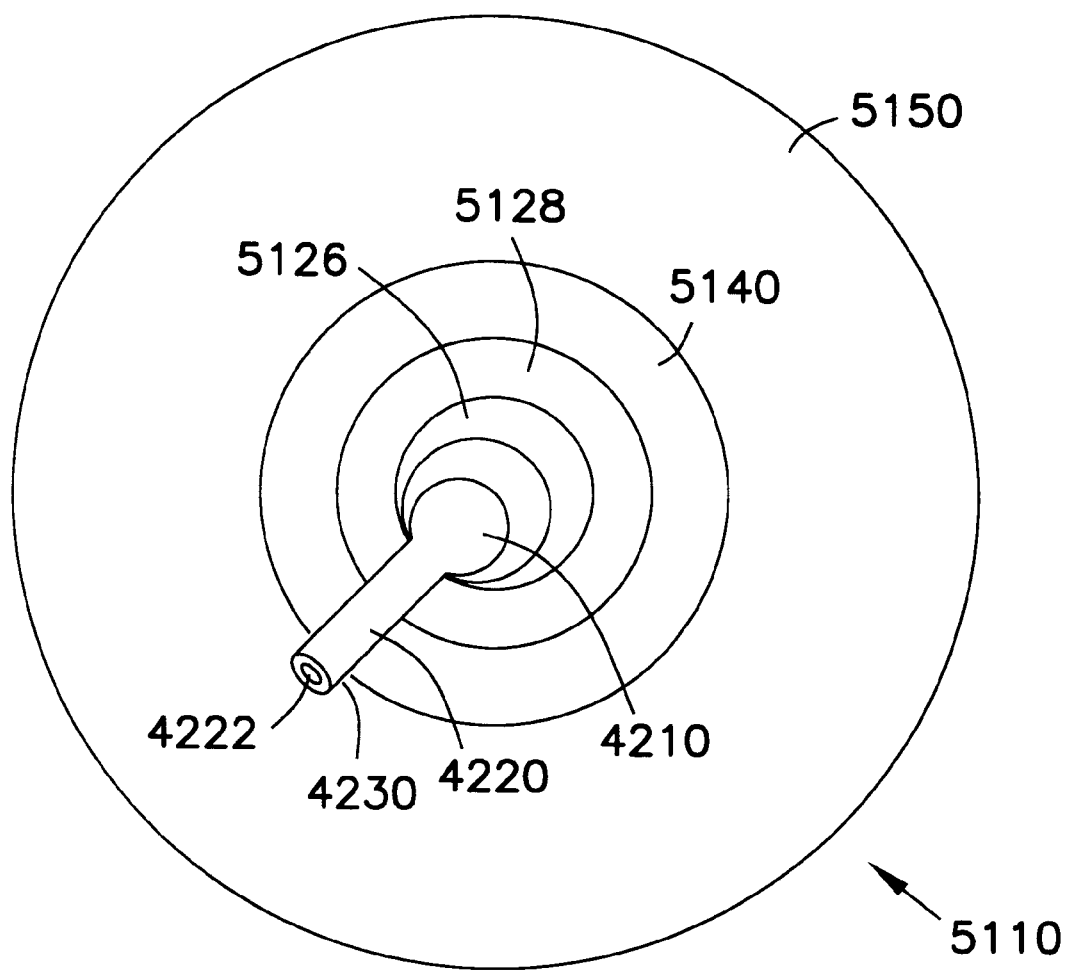
FIG. 55 is a top view of the body type trajectory guide.

FIGS. 53–55 show the body portal type trajectory guide 5110 in more detail. FIG. 53 is a side view of the body portal type trajectory guide 5110 and FIG. 54 is a cutaway side view of the body portal type trajectory guide 5110. The movable element 4220 includes passageway 4222. The movable element 4220 also has a guide stem end 4230 and a base end 4210. The base end 4210 is ball shaped. The body portal type trajectory guide 5110 includes a base 5120 which has an opening or passageway 5122 therein. The passageway 5122 allows the surgical instrument to pass into the body of the patient and to a target 270 within the patient. At one end of the passageway 5122 is a cup 5124. The cup 5124 is dimensioned such that the cup grips the ball end 4210 of the positioning member 4220. The cup 5124 may also include portions which extend beyond the largest diameter of the ball end 4210 to further grip the ball end 4210 of the movable member 4220. The base 5120 also includes an angled portion 5126 and a flat base portion 5128. The flat base portion 5128 is circular and includes a first flange 5130 and a second flange 5132. A plastic ring 5140 includes a finger 5142 which engages the slot between the first flange 5130 and the second flange 5132 of the flat base. The plastic finger 5142 engages the slot between the first flange 5130 and the second flange 5132 so that the base 5120 can rotate or swivel with respect to the plastic ring 5140. The plastic ring 5140 is merged or attached to a flexible adhesive patch 5150. The flexible adhesive patch is made from a flexible material which can conform to various body portions or parts of a patient. An adhesive material is placed on one side of the flexible adhesive patch. The adhesive is placed on surface 5152 which is opposite the side of the flexible adhesive patch 5150 closest to the angled base portion 5126. The flexible adhesive patch 5150 is made of a biocompatible material such as might be used to affix a colostomy bag to a patient or a similar material. FIG. 55 shows an embodiment that includes a quick locking mechanism 5400. The base is provided with a high pitch thread. The locking mechanism 5400 is provided with a matching high pitch thread. The locking mechanism 5400 is also provided with a single arm or knob 5410 for turning the locking mechanism 5400 with respect to the threaded base portion. The knob 5410 is positioned away from the patient so that the surgeon has easy access to the knob 5410. Because a high pitch thread length is used, the knob needs to be turned only slightly to lock the movable element 4220 into position with respect to the base.

FIG. 55 is a top view of the body portal-type trajectory guide 5110. The movable member 4220 includes the guide stem end 4230 and the ball end 4210 which is positioned within the cup 5124. The base is angled through the angled base portion 5126 and is attached to the flat base portion 5128. The flat base portion is attached to the plastic ring portion 5140 which in turn is merged with a flexible body patch 5150.

In operation, the body portal type trajectory guide 5110 is used as follows. Initially, the surgeon determines the approximate location of the target 270 within the body of the patient. An incision is made in the patient near the target 270. The body portal type trajectory guide 5110 is then placed over the incision so that the passageway 5122 in the base 5120 is positioned over the incision that is made in the patient. The passageway 5122 is roughly aligned with a line between the target and the incision within the patient. The flexible adhesive patch 5150 is attached to the patient to seal the incision as well as to provide a stable attachment point for the body portal type trajectory guide 5110. The movable member 4220 can be repositioned with respect to the cup 5124 within the base 5120 of the trajectory guide 5110. The entire base 5120 can be moved with respect to the plastic ring 5140 and the flexible adhesive patch 5150. By moving the base with respect to the flexible adhesive patch, a surgeon is afforded the flexibility to work from a variety of positions with respect to the patient and with respect to the MR scanner which is positioned around the patient. Initially, the physician will roughly position the base 5120 with respect to the target. The base 5120 can be rotated with respect to the plastic ring and flexible adhesive patch to enable the surgeon to take any position with respect to the incision and the patient. The movable member 4222 can then be moved to assure that the surgical instrument that will be placed within the opening or passageway 4222 in the movable member 4220 will intersect with the target 270. The movable member can be equipped with RF micro coils to aid in positioning the movable member, similar to those described in U.S. patent application Ser. No. 08/919,649 filed Aug. 8, 1997 and entitled "Surgical Instrument Trajectory Guide Method and Apparatus".

It should be noted that the body portal type trajectory guide 5110 will be used when the targets 270 are relatively large. In other words, a trajectory guide 5110 can be used to take a biopsy of a liver, which is a relatively large organ. Thus, if the guide member 4220 is slightly out of position, the sample will come from just a slightly different portion of the liver but will still be valid. Although a locking member could be provided, the body portal type trajectory guide 5110 shown does not feature a locking member for the movable member 4222. The cup 5124 holds the ball end 4210 of the movable member 4220 tightly such that it will not move under most conditions. As stated before, the body portal type trajectory guide 5110 is used on relatively large targets 270 and, therefore, slight movement of the movable member due to respiratory excursion will not affect the placement of the surgical instrument within the large target 270. Once the surgical instrument has been inserted through the passageway 4222 and the passageway 5122 and to the target 270 and the operation has been performed, the surgical instrument is removed. The body patch 5150 can then also be removed. By removing the body patch 5150, the entire trajectory guide 5110 is also removed. The incision is then sewn or bandaged by the surgeon to end the operation. The main advantages of the body portal type trajectory guide 5110 is that the operation can be done relatively quickly in either a CT or MR environment. The body patch 5150 also keeps the area clear and clean. Operations that used to be difficult or impossible or used to take large amounts of time can now be performed easily and efficiently.

There are many other uses contemplated for the body portal type trajectory guide 5110. The trajectory guide 5110 can be used to biopsy or provide therapy to organs in or near the abdomen or pelvis. Among the uses are liver biopsies, renal biopsies, pancreatic biopsies, adrenal biopsies. In addition, some procedures require both a biopsy as well as a therapy. The biopsy needle is used first and then an instrument used in therapy is substituted for the biopsy needle. The instrument for applying therapy includes instruments for thermal ablation, and instruments for providing shunts to various organs such as TIPS (transjugular interhepatic portal systemic shunts). The trajectory guide 5110 can also be used to conduct biliary drainages, and used to conduct other biopsies and treatments at or near the abdomen of the pelvis. The trajectory guide 5110 can also be used for procedures on the back and near the spine of a patient. Nerve blocks, epidural injections, facet injections, sacroiliac joint injections, and spinal cordotomy are just a few of the procedures possible with the trajectory guide 5110. Non-brain treatments and biopsies in the head and neck can also be accomplished using the trajectory guide 5110. Trigeminal neuralgia can be treated using the trajectory guide 5110. Biopsies of the pleura, the lung, and the mediastinum and removal of emphysematous to reduce the volume of the lung can be done percutaneously using the trajectory guide. The trajectory guide 5110 can also be used for fetal surgery such as for diversion of fetal hydrocephalus, and for treatment of fetal hydronephrosis. These are just a sampling of the possible procedures that can be done using the body portal type trajectory guide 5110. Numerous other procedures will be accomplished using this device. In addition, the device will give rise to other future surgical procedures.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A surgical device comprising:

a base unit;

a ball having a passage therein, said ball fitting within the base unit, said ball capable of rotating with respect to the base unit;

a positioning stem connected to said ball, said positioning stem having proximal and distal ends and having a locator attached to said positioning stem, said locator having two portions in spaced relation with respect to each other, each said locator portion comprising a component which provides a distinctly readable reference point when read using a scanning device;

whereby both said reference points are provided for use as inputs to a computer device functionally attached to said scanning device, said inputs used to calculate a trajectory for guiding a surgical instrument to a target site in a patient;

a platform; and a locking member which engages the ball and fixes the position of the ball and positioning stem upon tightening the locking member when the ball is properly positioned.

2. The surgical device of claim 1, wherein said locator on said positioning stem includes light emitting diodes.

3. The surgical device of claim 1, wherein said locator on said positioning stem includes a cavity which carries a liquid which is visible to a nuclear magnetic resonance imaging system.

4. The surgical device of claim 1, wherein said locator on said positioning stem includes at least one radiofrequency coil.

5. The surgical device of claim 1, wherein said platform further comprises a stage which is movable in a plane of the platform.

6. The surgical device of claim 1 further comprising a guide stem, said guide stem having an opening therein and attached to said surgical device such that the opening in the guide stem substantially aligns with the passage in the ball.

7. The surgical device of claim 6 wherein the positioning stem fits within the opening of the guide stem.

8. The surgical device of claim 7 wherein the locator is readable by an imaging apparatus.

9. The surgical device of claim 7 further comprising an actuator attached to said guide stem, said actuator used to move the guide stem and ball having a passage therein.

10. The surgical device of claim 6 further comprising;
a suspension tube attached to said base unit; and
a stage attached to said suspension tube, said stage moving the ball with the opening therein in a plane transverse to the opening in the guide stem and the passage in the ball.

11. The surgical device of claim 6 further comprising an actuating system for positioning the guide stem and ball.

12. The surgical device of claim 6 further comprising an actuating system for moving an instrument through the opening in the guide stem and through the passage in the ball.

13. The surgical device of claim 1, wherein said scanning device detects infrared energy.

14. The surgical device of claim 1, wherein said locator on said positioning stem includes an energy emitting device.

15. An apparatus comprising:
a base;
a movable member movably attached to said base and having a passage therein;
a locking member for fixing the position of the movable member; and
a positioning stem further comprising:
a first locator; and
a second locator, said first locator associated with a first position of said positioning stem and said second locator associated with a second portion of said positioning stem, said positioning stem removably attached to said movable member and used to position the movable member and the passage therein, wherein each of the first and second locators comprise a component which provides a distinctly readable reference point when read using a scanning device;
whereby both said reference points are provided for use as inputs to a computer device functionally attached to said scanning device, said inputs used to calculate a trajectory for guiding a surgical instrument to a target site in a patient.

16. The apparatus of claim 15 wherein said first and second locators are readable by a body scanning mechanism.

17. The apparatus of claim 16 wherein said first and second locators are readable by a magnetic resonance imaging apparatus.

18. The apparatus of claim 17 wherein at least one of said first locator and said second locator includes a fluid readable by a magnetic resonance imaging apparatus.

19. The apparatus of claim 17 wherein at least one of said first locator and said second locator includes a radio frequency coil which is readable by a magnetic resonance imaging apparatus.

20. The apparatus of claim 19 wherein said source of radio frequency which is readable by a magnetic resonance imaging apparatus includes at least one or more radiofrequency coils.

21. The apparatus of claim 19 wherein said first and second locators are offset with respect to a centerline of the passage in said movable member.

22. The apparatus of claim 15 wherein said first and second locators are substantially aligned with the centerline of the passage in said movable member.

23. The apparatus of claim 15 wherein said first and second locators are offset with respect to the centerline of passage in said movable member.

24. The apparatus of claim 15 further comprising a guide stem, said guide stem having an opening therein and attached to said movable member such that the opening in the guide stem substantially aligns with the passage in the movable member.

25. The apparatus of claim 24 wherein said positioning stem is interchangeable with said guide stem.

26. The apparatus of claim 24 wherein said positioning stem fits within the opening in said guide stem.

27. The apparatus of claim 26 further comprising a first actuator system for positioning the guide stem.

28. The apparatus of claim 27 wherein said passage in said movable member and said opening in said guide stem form a trajectory, said first actuator system moving the positioning (and/or guide) stem to a position where the trajectory is substantially aligned with a target area within the patient.

29. The apparatus of claim 27 wherein said passage in said movable member and said opening in said guide stem form a trajectory, said first actuator system moving the guide stem to a position where the trajectory is substantially aligned with a target area within the patient.

30. The apparatus of claim 27 further comprising a second actuator system for moving an instrument throught the opening in the guide stem.

31. The apparatus of claim 15 wherein the base, the movable member, the positioning stem, and the locking member are made out of materials useable within a magnetic resonance imaging environment.

32. The apparatus of claim 15 wherein at least one of said first second-locators includes a light emitting diode.

33. The apparatus of claim 15 further comprising a stage attached to the base, said stage defining a plane which intersects a centerline of the passage in the movable member.

34. The apparatus of claim 15 further comprising a cap and plug for sealing an opening in the base.

35. A method for determining a trajectory for an instrument through a guiding device for use with a scanning device, said scanning device including a central processing unit and a memory, said method comprising the steps of:
selecting a target within a patient;
attaching a positioning stem to a movable member carried by the guiding device, the movable member having a passage therein, said positioning stem having a first portion readable by the scanning device and a second portion readable by the scanning device;
determining the position of the first and second portions of the positioning stem;
determining if the passage in the movable member is substantially aligned with the target within the patient based on the position of the first and second portions of the positioning stem.

36. The method for determining a trajectory for an instrument of claim 35 further comprising the step of locking the movable member when the passage within the movable member is substantially aligned with the target within the patient.

37. The method for determining a trajectory for an instrument of claim 35 further comprising the steps of:
removing the positioning stem from the movable member; and
attaching a guide stem to the movable member, said guide stem having an opening therein, said opening in the guide stem substantially aligned with the passage in the movable member when the guide stem is attached to the movable member.

38. The method for determining a trajectory for an instrument of claim 35 further comprising the steps of:

removing the positioning stem from the movable member, said movable member including a guide stem attached to the movable member, said guide stem having an opening therein, said opening in the guide stem substantially aligned with the passage in the movable member, said step of removing the positioning stem including removing the positioning stem from the guide stem.

39. The method for determining a trajectory for an instrument of claim 35 wherein the step of determining the position of the first and second portions of the positioning stem is performed at least in part by the central processing unit and the memory of the scanning device.

40. The method for determining a trajectory for an instrument of claim 35 wherein the step of determining if the passage in the movable member is substantially aligned with the target within the patient is performed at least in part by the central processing unit and the memory of the scanning device.

41. The method for determining a trajectory for an instrument of claim 35 further comprising the steps of:

providing a stage which defines a plane which intersects the centerline of the opening in the movable member; and moving the stage in the plane to define a trajectory which is substantially parallel to the initially determined trajectory.

42. The method for determining a trajectory for an instrument of claim 35 further comprising the steps of:

providing a stage which defines a plane which intersects a centerline of the opening in the movable member, said stage including the movable member; and moving the stage in the plane to define a trajectory which is substantially parallel to the initially determined trajectory.

43. The method for determining a trajectory for an instrument of claim 35 further comprising the step of repositioning the first and second locators on the positioning stem using an actuator system.

* * * * *

UNITED STATES PATENT AND TRADEMARK OFFICE
CERTIFICATE OF CORRECTION

PATENT NO. : 6,206,890 B1
DATED : March 27, 2001
INVENTOR(S) : Charles L. Truwit It is certified that error appears in the above-identified patent and that said Letters Patent is hereby corrected as shown below:

Column 1,
Line 27, delete "of" after "diseases".

Column 7,
Line 36, delete "an" before "side" and insert -- a --, therefor.

Column 10,
Line 55, delete "withing" and insert -- within --, therefor.

Column 12,
Line 33, delete "rectangles" and insert -- rectangle's --, therefor.

Column 16,
Line 21, insert -- . -- after "patient".
Line 26, delete "an" before "surgeon" and insert -- a --, therefor.

Column 19,
Line 11, delete "1000 and 1000" and insert -- 1000 and 1000' --, therefor.
Line 12, delete "one" after "1000'" and insert -- are --, therefor.

Column 20,
Line 51, delete "on the" after "fluid".

Column 21,
Line 24, delete "in are" after "device".
Line 40, insert -- . -- after "240".

Column 22,
Line 43, delete "can" after "assembly" and insert -- to --, therefor.

Column 26,
Lines 40-41, delete "to require" after "procedures" and insert -- required --, therefor.

UNITED STATES PATENT AND TRADEMARK OFFICE
CERTIFICATE OF CORRECTION

PATENT NO. : 6,206,890 B1
DATED : March 27, 2001
INVENTOR(S) : Charles L. Truwit Page 2 of 3

It is certified that error appears in the above-identified patent and that said Letters Patent is hereby corrected as shown below:

Columns 26-27, lines 29-67 and lines 1-2, the following paragraph should be deleted after "Still other procedures" in column 27, line 29 and inserted between "The" and "element 2340," in column 28, line 39:

"second arm 2320 has a handle 2322 on one end and a cup 2324 on the other end. A movable member 220 with a passage or opening 222 therein is held between the cups 2314 and 2324. The movable member 220 is a ball or is substantially spherical in shape. The cups 2314 and 2324 have a radius that is close to the radius of the substantially spherically shaped movable member 220. The cups 2314 and 2324 may also be lined with an elastomeric or other material to enhance the gripping of the cups on the movable member 220. It should be noted that the size of the movable member 220 is not limited to one size and that larger and smaller spherically shaped movable members may require specialized surgical instruments 2300 having cups 2314 and 2324 with radii that are near the radius of the movable member 220. Located between the handles 2312 and 2322 is a bias or spring element 2340. The spring element 2340 is held in compression between the handle 2312 and the handle 2322. The spring element 2340 therefore biases the arm 2312 away from the arm 2322 which in turn biases cup 2314 toward cup 2324. The surgical instrument 2300 is designed so that in the absence of a force which counteracts the spring or bias element 2340, the cups 2314 and 2324 will engage the movable member 220 to fix it in one position so that surgical instruments may be passed through the opening 222 in the movable member 220. The spring element or bias element 2340 can be mounted on an arcuate portion which is attached to one of either the first arm 2312 or the second arm 2322. The spring or bias element 2340 can be placed over the arcuate member. A mating or receiving member can be attached to the opposite arm. The opposite arm also may include an opening for allowing the arcuate member to pass through the opening. A stop is typically provided on the surgical instrument 2300. The stop 2350 limits the amount of motion that can take place between the movable member 220 and the cups 2314 and 2324. By limiting the amount of motion between the cups 2314 and 2324, the spherical movable member 220 cannot be removed from the surgical instrument 2300. This would prevent an inadvertent drop of the movable member 220 during a critical portion of an operation. The stop 2350 can be incorporated within the bias"

Column 29,
Line 27, insert -- with -- between "used" and "other".

Column 30,
Line 7, delete "abase" and insert -- a base -- therefor.

Column 32,
Line 40, delete "FIGS. 142" and insert -- FIGS. 1-42 --, therefor.

Column 39,
Line 22, delete "such-procedures" and insert -- such procedures -- therefor.

UNITED STATES PATENT AND TRADEMARK OFFICE
CERTIFICATE OF CORRECTION

PATENT NO.    : 6,206,890 B1
DATED         : March 27, 2001
INVENTOR(S)   : Charles L. Truwit It is certified that error appears in the above-identified patent and that said Letters Patent is hereby corrected as shown below:

Column 40,
Line 14, delete "abase" and insert -- a base -- therefor.

Column 43,
Line 48, delete referenced claim "16" and insert -- 15 --, therefor.
Line 66, delete "the" before "centerline" and insert -- a --, therefor.

Column 44,
Line 2, delete "the" before "centerline" and insert -- a --, therefor.
Line 18, delete "(and/or guide)".
Line 26, delete "throught" and insert -- through --, therefor.

Column 46,
Line 5, delete "the" before "centerline" and insert -- a --, therefor.

Signed and Sealed this

Twenty-fourth Day of June, 2003

JAMES E. ROGAN
*Director of the United States Patent and Trademark Office*